United States Patent
Choi et al.

(10) Patent No.: US 10,933,051 B2
(45) Date of Patent: Mar. 2, 2021

(54) CARBAPENEM COMPOUNDS AND COMPOSITIONS FOR THE TREATMENT OF BACTERIAL INFECTIONS

(71) Applicant: FOB Synthesis, Inc., Kennesaw, GA (US)

(72) Inventors: Woo-Baeg Choi, Sandy Springs, GA (US); Takashi Tomioka, Kennesaw, GA (US); Hyung-Yeul Joo, Marietta, GA (US); Phong Truong, Norcross, GA (US); Brian Min, Marietta, GA (US)

(73) Assignee: FOB Synthesis, Inc., Kennesaw, GA (US)

( * ) Notice: Subject to any disclaimer, the term of this patent is extended or adjusted under 35 U.S.C. 154(b) by 0 days.

(21) Appl. No.: 16/619,495

(22) PCT Filed: Jun. 11, 2018

(86) PCT No.: PCT/US2018/036872
§ 371 (c)(1),
(2) Date: Dec. 5, 2019

(87) PCT Pub. No.: WO2018/227178
PCT Pub. Date: Dec. 13, 2018

(65) Prior Publication Data
US 2020/0155508 A1    May 21, 2020

Related U.S. Application Data

(60) Provisional application No. 62/517,422, filed on Jun. 9, 2017.

(51) Int. Cl.
| | | |
|---|---|---|
| *C07D 477/14* | (2006.01) | |
| *A61K 31/407* | (2006.01) | |
| *A61P 31/04* | (2006.01) | |
| *A61K 45/06* | (2006.01) | |

(52) U.S. Cl.
CPC ............ *A61K 31/407* (2013.01); *A61K 45/06* (2013.01); *A61P 31/04* (2018.01); *C07D 477/14* (2013.01)

(58) Field of Classification Search
CPC .................................................... C07D 477/14
See application file for complete search history.

(56) References Cited

U.S. PATENT DOCUMENTS

| | | |
|---|---|---|
| 5,541,178 A | 7/1996 | Betts et al. |
| 7,205,291 B2 | 4/2007 | Sunagawa et al. |
| 8,557,979 B2 | 10/2013 | Choi et al. |

OTHER PUBLICATIONS

International Search Report from PCT/US2018/036872, dated Oct. 19, 2018.

*Primary Examiner* — Shawquia Jackson
(74) *Attorney, Agent, or Firm* — King & Spalding

(57) ABSTRACT

The present invention provides carbapenem compounds and pharmaceutical compositions useful in the treatment of bacterial infections, including drug resistant or multiple-drug resistant bacterial infections, and methods for treating such infections using such compounds and/or compositions. The invention includes administering an effective amount of a carbapenem compound or salt and/or prodrug thereof to a host in need of such a treatment.

17 Claims, No Drawings

CARBAPENEM COMPOUNDS AND COMPOSITIONS FOR THE TREATMENT OF BACTERIAL INFECTIONS

CROSS-REFERENCE TO RELATED APPLICATION

The application is a national stage application under 35 U.S.C. § 371 of International Application No. PCT/US2018/036872, filed Jun. 11, 2018, which claims priority to U.S. Provisional Application No. 62/517,422, filed Jun. 9, 2017. The complete disclosure of each of the above-identified applications is fully incorporated herein by reference.

FIELD OF THE INVENTION

The present invention provides novel carbapenem compounds, compositions comprising the compounds, and methods for the treatment or prevention of bacterial infections with the compounds and compositions.

BACKGROUND

The worldwide exploitation of antibiotics to treat infectious diseases has grown dramatically over the last forty years. In 1954, two million pounds of antibiotics were produced in the United States. Today, the figure exceeds 50 million pounds. According to the Centers Disease Control (CDC), humans consume 235 million doses of antibiotics annually.

Widespread misuse or overuse of antibiotics has fostered the spread of antibiotic resistance and has contributed to the development of a serious public health problem. Antibiotic resistance occurs when bacteria that cause infection are not killed by the antibiotics taken to stop the infection. The bacteria survive and continue to multiply, causing more harm. For example, multi-drug resistant (MDR) *Acinetobacter baumannii* (*A. baumannii*) is a rapidly emerging pathogen in healthcare settings, where it causes infections that include bacteremia, pneumonia, meningitis, and urinary tract and wound infections.

Antibiotics are used therapeutically to treat bacterial infections. Several types of antibiotics, classified according to their mechanism of action, are currently employed. The known types of antibiotics include, e.g. cell wall synthesis inhibitors, cell membrane inhibitors, protein synthesis inhibitors and inhibitors that bind to or affect the synthesis of DNA or RNA.

Cell wall synthesis inhibitors, such as beta lactam antibiotics, generally inhibit some step in the synthesis of bacterial peptidoglycan. Penicillin is generally effective against non-resistant *streptococcus*, gonococcus and *staphylococcus*. Amoxycillin and Ampicillin have broadened spectra against Gram-negative bacteria. Cephalosporins are generally used as penicillin substitutes, against Gram-negative bacteria and in surgical prophylaxis. Monobactams are generally useful for the treatment of allergic individuals.

Numerous antibiotic agents, suitable for use in the treatment of bacteria-related diseases and disorders, are known and disclosed, e.g. in *The Physician's Desk Reference* (PDR), Medical Economics Company (Montvale, N.J.), (53rd Ed.), 1999; *Mayo Medical Center Formulary*, Unabridged Version, Mayo Clinic (Rochester, Minn.), January 1998; *Merck Index: An Encyclopedia of Chemicals, Drugs and Biologicals*, (11th Ed.), Merck & Co., Inc. (Rahway, N.J.), 1989; University of Wisconsin Antimicrobial Use Guide, http://WWW.medsch.Wisc.edu/clinsci/5amcg/amcg.html; *Introduction on the Use of the Antibiotics Guideline, of Specific Antibiotic Classes*, Thomas Jefferson University, http://jeffline.tju.edu/CWIS/OAC/antibiotics_guide/intro.html; and references cited therein.

The first carbapenem to be isolated was thienamycin, shown below, which was isolated from *Streptomyces cattleya* (U.S. Pat. No. 3,950,357) and shown to have strong antibacterial activity, including potency against *Pseudomonas* spp. and ß-lactamase stability (Kahan, J. S., et al., *J. Antibiot*, 32, pp. 1-12 (1979); Bodey, G. P., et al., *Antimicrob. Agents Chemother.*, 15, pp. 518-521 (1979). The racemic synthesis of thienamycin was reported shortly thereafter by Merck (Johnston, D. B. R., et al., *J. Am. Chem. Soc.*, 100, pp. 313-315 (1978); Bouffard, F. A., et al., *J. Org. Chem.*, 45, 1130-1142 (1980)), as well as an asymmetric total synthesis (SalZmann, T. N., et al., *J. Am. Chem. Soc.* 102, pp. 6161-6163 (1980)). The nucleus and amino-containing side chain of this molecule,

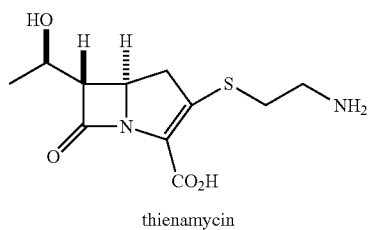 [SMILES: C[C@@H](O)[C@H]1C(=O)N2C(C(=O)O)=C(SCCN)C[C@H]12]

thienamycin however, contributed to its chemical instability. In addition to its potential to be hydrolyzed by the zinc-activated ß-lactamase that is present in *Bacillus* species, *Xanthomonas*, *Pseudomonas*, and *Bacteroides* species (Saino, Y., et al., *Antimicrob. Agents Chemother*, 22, pp. 564-570 (1982); Yotsujii, A., et al., *Antimicrob. Agents Chemother.*, 24, pp. 925-929 (1983)), chemical stability issues associated with the intermolecular aminolysis of the azetidinone (ß-lactam) ring of one molecule of thienamycin by the primary amine in the cysteamine side chain of another thienamycin molecule, resulted in the use of thienamycin as a drug candidate to be abandoned.

As a result of the problems associated with thienamycin, N-formimidoyl thienamycin, known as imipenem, was synthesized (LeanZa, W. J., et al., *J. Med. Chem.*, 22, pp. 1435-1436 (1979)). This compound bears a more basic amidine functionality on the 2' side chain, which is protonated at physiological pH, preventing the compound from initiating a nucleophilic attack on another imipenem molecule.

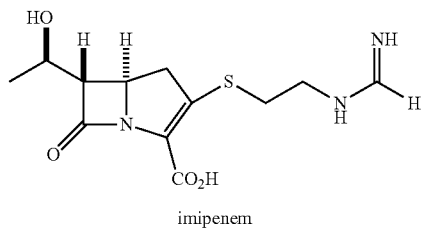 [SMILES: C[C@@H](O)[C@H]1C(=O)N2C(C(=O)O)=C(SCCNC=N)C[C@H]12]

imipenem

However, poor urinary tract recovery from test subjects revealed an instability of this compound to the mammalian ß-lactamase renal dehydropeptidase-I (DHP-I) (Shimada, J., et al., *Drugs Exp Clin Res.*, 20, pp. 241-245 (1994)). Consequently, the compound cilastatin was developed for use in co-administration in order to prevent hydrolysis and degradation by DHP-I; this combination therapy is currently prescribed under the name Primaxin® (Merck Frosst Std).

In response to the problem of carbapenems to destruction by renal dehydropeptidase-1, the carbapenem antibiotic meropenem (SM7338) (shown below), was developed (see, Edwards, J. R., et al., *Antimicrob. Agents Chemother*, 33, pp. 215-222 (1989); Neu, H. C., et al., *Antimicrob. Agents Chemother*, 33, pp. 1009-1018 (1989)).

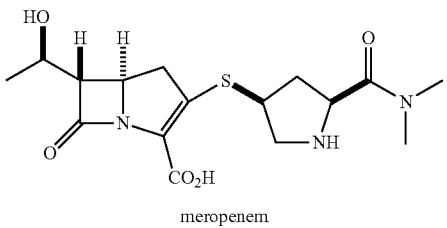 [SMILES: C[C@@H](O)[C@H]1C(=O)N2C(C(=O)O)=C(S[C@@H]3CN[C@H](C(=O)N(C)C)C3)C[C@H]12]

meropenem

This compound was shown to be active against a large number of Gram-negative bacteria. The drug is currently prescribed for intravenous use (Merrem® IV; AstraZeneca) in the treatment of intra-abdominal infections and bacterial meningitis.

The carbapenem ertapenem (formerly MK-0826; Cunha, B. A., *Drugs of Today*, 38, pp. 195-213 (2002)) was the first of a group of carbapenems with potential against methicillin-resistant staphylococci (MRS) shown to be useful as a long-acting, parenteral carbapenem (Shah, P. M., et al., *J. Antimicrob. Chemother*, 52, pp. 538-542 (2003); Aldridge, K. E., *Diagn. Microbiol. Infect. Dis*, 44(2), pp. 181-6 (2002)). It is suitable for administration either as a single-agent (e.g., co-administration with a compound such as cilastatin is not required), or by the intravenous or intra-muscular route (Legua, P., et al., *Clin. Therapeut*, 24, pp. 434-444 (2002); Majumdar, A. K., et al., *Antimicrob. Agents Chemother*, 46, pp. 3506-3511 (2002)). Ertapenem has received regulatory approval in both the United States (November, 2001) and the European Union (April, 2002).

One carbapenem having a fused pyrazole ring system (L-627; Biapenem) was developed by Lederle Ltd. (Japan), and introduced a methyl radical at the 1-ßposition of the carbapenem skeleton (see, U.S. Pat. No. 4,866,171). This structural modification reportedly gave Biapenem stability against hydrolysis by kidney dehydropeptidase, making coadministration of a dehydropeptidase inhibitor unnecessary.

More recently, an injectable 1-ß-methyl carbapenem antibiotic having an (R)-1-hydroxymethyl-methylaminopropyl group exhibiting both broad spectrum, potent antibacterial activity (BO-2727) and having antipseudomonal activity has been reported (Nakagawa, S., et al., *Antimicrob. Agents Chemother*, 37, pp. 2756-2759 (1993); Hazumi, N., et al., *Antimicrob. Agents Chemother*, 39, pp. 702-706 (1995).

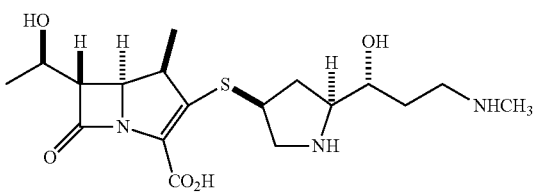

BO-2727

Since the discovery of thienamycin having a potential antimicrobial activity against Gram-negative and Gram-positive bacteria, studies on the syntheses of carbapenem derivatives which are analogous to thienamycin have been widely developed. As a result, it was found that carbapenem derivatives having, as their 2-side chain, a substituent derived from 4-hydroxy-proline exhibit a potential antimicrobial activity and are useful as medicines or as intermediates for compounds possessing antimicrobial activity.

1-ß-methyl carbapenem antibiotics, are particularly well known for treating a broad spectrum of Gram-negative and Gram-positive bacterial infections. See for example U.S. Pat. Nos. 4,962,103; 4,933,333; 4,943,569; 5,122,604; 5,034,384 and 5,011,832.

U.S. Pat. No. 6,255,300 to Merck & Co. describes certain carbapenem antibacterial agents in which the carbapenem nucleus is substituted with an iodo-phenyl linked through a methyl-oxygen linkage. The patent states that these compounds are useful against Gram-positive bacterial infections. Similarly, U.S. Pat. No. 6,310,055 provides carbapenem compounds with aromatic side chains that are halogen substituted, linked thorough an alkoxy unsaturated group.

European Publication No. 0 292 191 to Merck & Co. describes certain 2-(substituted methyl)-1-alkylcarbapenem compounds useful as antibiotic agents.

U.S. Pat. No. 6,399,597, also to Merck & Co. describes certain napthosultam compounds that are allegedly useful in the treatment of certain drug resistant bacterial infections.

U.S. Pat. No. 7,683,049 to FOB Synthesis, Inc. describes certain ß-methyl carbapenem compounds for the treatment of Gram-negative bacterial infections.

Because of the drug-resistance challenges associated with treating bacterial infections, there remains a need for new antimicrobial agents.

Therefore, it is one object of the present invention to provide novel ß-methyl compounds carbapenems that are effective antimicrobial agents.

It is another object of the present invention to provide methods for the treatment of Gram-negative bacteria, which optionally can be drug-resistant and/or multi-drug resistant.

SUMMARY OF THE INVENTION

Disclosed herein are carbapenem compounds of formula (I):

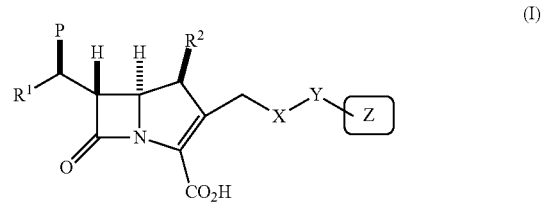

(I)

or a pharmaceutically acceptable salt or prodrug thereof, wherein:
$R^1$ and $R^2$ are each independently selected from H or alkyl;
P is H, OH, halogen, or hydroxyl protected by a hydroxyl protecting group;
X is (1) an acylic or cyclic alkyl amino based linker, optionally substituted by one or more substituents selected from the group consisting of alkyl, haloalkyl, OR, CN, CONRR', SR, or NRR' or (2) a quaternary ammonium cation based linker, optionally substituted by one or more substituents selected from the group consisting of alkyl, haloalkyl, OR, CN, CONR$_2$, SR, or NRR';

Y is a divalent —NR(C=O)—(CR$_2$)$_n$— or —(C=O) NR—(CR$_2$)$_n$— group, wherein n is 0, 1, or 2;

R and R' are each independently selected from H or alkyl;

Z is an aromatic or heteroaromatic ring, substituted by one or more substituents selected from the group consisting of alkyl, haloalkyl, OH, halogen, or hydroxyl protected by a hydroxyl protecting group.

Also disclosed herein are carbapenem compounds of Formula IIa, IIb, IIIa and IIIb

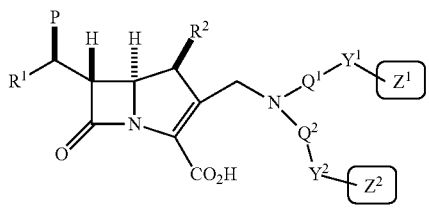

Formula (IIa)

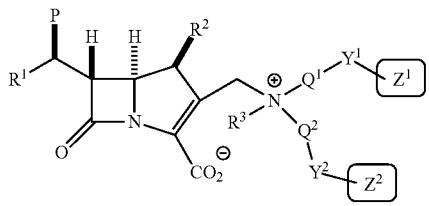

Formula (IIb)

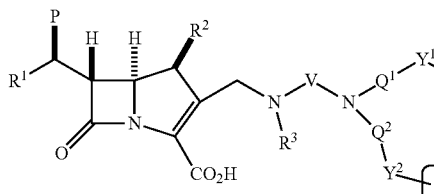

Formula (IIIa)

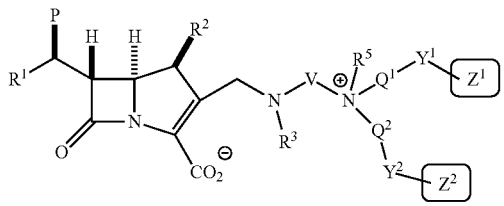

Formula (IIIb)

or a pharmaceutically acceptable salt or prodrug thereof, wherein:

R$^1$, R$^2$ and R$^3$ are each independently selected from H or alkyl;

P is H, OH, halogen, or hydroxyl protected by a hydroxyl protecting group;

V is a divalent —(CR$_2$)$_n$—(C=O)— or —(CR$_2$)$_n$— group, wherein n is 1, 2 or 3;

Q$^1$ and Q$^2$ are each independently selected from a divalent —(CR$_2$)$_p$—W—(CR$_2$)$_q$—, optionally substituted by one or more substituents selected from the group consisting of alkyl, haloalkyl, OR, CN, CONRR', SR, or NRR';

p and q are each independently 0, 1, or 2, and at least one of p or q is not 0;

W is absent, —CONR—, or —NRCO—;

Y$^1$ and Y$^2$ are each independently selected from a divalent —NR(C=O)—(CR$_2$)$_n$— or —(C=O)NR—(CR$_2$)$_n$— group, wherein n is 0, 1, or 2;

Z$^1$ and Z$^2$ are each independently selected from an aromatic or heteroaromatic ring, substituted by one or more substituents selected from the group consisting of alkyl, haloalkyl, OH, halogen, or hydroxyl protected by a hydroxyl protecting group; and R$^5$ is H or alkyl.

In one embodiment, the invention also provides a pharmaceutical composition comprising a compound of the invention, or a pharmaceutically acceptable salt and/or prodrug thereof, optionally with a pharmaceutically acceptable carrier or diluent.

In another embodiment, the invention provides a pharmaceutical composition comprising a compound of the invention, or a pharmaceutically acceptable salt and/or prodrug therein, in combination with one or more other antimicrobial agents, optionally with a pharmaceutically acceptable carrier or diluent.

In another embodiment, the invention provides a method of preventing or treating a bacterial infection in a host, typically an animal, and most typically a human, including administering to the host a therapeutic amount of a compound of the present invention, or a pharmaceutically acceptable salt and/or prodrug therein, optionally in a pharmaceutically acceptable carrier or diluent.

In a separate embodiment, the invention provides a method of preventing or treating a bacterial infection in a host that includes administering a therapeutic amount of a compound of the present invention, or a pharmaceutically acceptable salt and/or prodrug therein, in combination or alternation with one or more other antimicrobial agents, optionally in a pharmaceutically acceptable carrier or diluent.

In one principal embodiment, the bacterial infection is due to an *Acinetobacter baumannii* bacterium. In another embodiment, the bacterial infection is from a drug resistant *Acinetobacter baumannii* bacterium. In a particular embodiment, the bacterial infection is from a multi-drug resistant (MDR) *Acinetobacter baumannii* bacterium, an extensive drug resistant (XDR) *Acinetobacter baumannii* bacterium or a pandrug resistant (PDR) *Acinetobacter baumannii* bacterium.

The method of the present invention may be used to treat any suitable *Acinetobacter baumannii* infection. In one embodiment, the infection is selected from primary blood stream infections, pneumonia, central nervous system infections (e.g., meningitis, ventriculitis) tracheobronchitis, urinary tract infections, peritonitis, otitis media, abdominal infections, infections of the skin, infections of the soft tissues or a combination thereof.

In one embodiment, the method of the present invention may be used to treat a ventilator-associated *Acinetobacter baumannii* infection.

In certain embodiments, the method of the present invention results in a reduction of (i) one or more symptoms of the *Acinetobacter baumannnsii* infection, (ii) the course of infection (measured in days or weeks), (iii) the duration of the host's hospital stay (measured in days or weeks), or a combination thereof.

The invention also provides a compound of the present invention for use in medical therapy, and the use in the preparation of a medicament for the treatment of bacterial infections, particularly Gram-negative bacterial infections, alone or in combination with at least one additional agent, such as an antibacterial agent.

DETAILED DESCRIPTION

The carbapenem compounds disclosed herein, their pharmaceutically acceptable salts or prodrugs, and pharmaceutical compositions containing these compounds, can be used in the treatment or prevention of Gram-negative bacterial infections. The carbapenem compounds and compositions disclosed herein are particularly useful in the treatment or prevention of *Acinetobacter baumannii* infections, including drug-resistant and/or multi-drug resistant infections.

Definitions

The numbering system for the carbapenem compounds used in this specification is set out below, wherein the numbering of the carbapenem nucleus is in accordance with standards in the art (see, Tiraby, G., et al., Biochem J, 276 (pt. 1), pp. 269-270 (1991)).

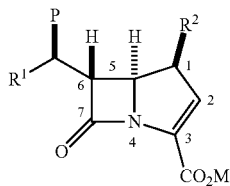

Whenever a range is presented herein it should be understood to include each element of the range. For example, the range "C1 to C4" alkyl independently includes C1, C2, C3 and C4 alkyl groups. When such a range is stated, each element has been contemplated and the range is used merely for convenience.

Generally, while the compounds, compositions and methods are described in terms of "comprising" various components or steps, the compounds, compositions and methods can also "consist essentially of" or "consist of" the various components and steps.

The term "alkyl", as used herein, unless otherwise specified, includes a saturated straight, branched, primary, secondary, or tertiary hydrocarbon of C1 to C10. The term includes both substituted and unsubstituted alkyl groups. Moieties with which the alkyl group can be substituted are selected from the group consisting of hydroxyl, halo (F, Cl, Br, I), amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference. When the alkyl group is said to be substituted with an alkyl group, this is used interchangeably with "branched alkyl group". Specific examples of alkyls and/or substituted alkyls includes, but are not limited to, methyl, trifluoromethyl, ethyl, propyl, isopropyl, butyl, isobutyl, t-butyl, pentyl, isopentyl, neopentyl, hexyl, isohexyl, 3-methylpentyl, 2,2-dimethylbutyl, and 2,3-dimethylbutyl.

The term "cycloalkyl" or "cyclic alkyl" refers to a species of alkyl containing from 3 to 15 carbon atoms including one or more rings, without alternating or resonating double bonds between carbon atoms. The term includes both substituted and unsubstituted cycloalkyl groups. Moieties with which the cycloalkyl group can be substituted are selected from the group consisting of hydroxyl, halo (F, Cl, Br, I), amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference. For example, cycloalkyls include but are not limited to cyclopropyl, cyclobutyl, cyclopentyl, and cyclohexyl. In certain embodiments, the cycloalkyl contains from 1 to 4 rings, which can be fused. In certain embodiments, the cycloalkyl group may contain one or more double bonds or triple bonds in one or more rings.

The term "alkenyl" includes a hydrocarbon radical straight, branched or cyclic containing from 2 to 10 carbon atoms and at least one carbon to carbon double bond. Examples of alkenyl groups include ethenyl, propenyl, butenyl and cyclohexenyl.

The term "alkynyl" refers to a hydrocarbon radical straight or branched, containing from 2 to 10 carbon atoms and at least one carbon to carbon triple bond. Examples of alkynyl groups include ethynyl, propynyl and butynyl.

"Alkoxy" includes $C_1$-$C_4$ alkyl-O—, with the alkyl group optionally substituted as described herein.

The term "alkylamino" or "arylamino" refers to an amino group that has one or two alkyl or aryl substituents, respectively.

"Aryl" refers to aromatic rings e.g., phenyl, substituted phenyl, biphenyl, and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The typical aryl groups are phenyl, naphthyl and phenanthrenyl. The term includes both substituted and unsubstituted moieties. The aryl group can be substituted with one or more moieties selected from the group consisting of bromo, chloro, fluoro, iodo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991. Typical substituted aryls include phenyl and naphthyl.

The term "alkaryl" or "alkylaryl" refers to an alkyl group with an aryl substituent. The term "aralkyl" or "arylalkyl" refers to an aryl group with an alkyl substituent.

The term "heteroaryl" or "heteroaromatic", as used herein, refers to an aromatic group that includes at least one sulfur, oxygen, nitrogen or phosphorus in the aromatic ring. Heteroaryl or heteroaromatic compounds include monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one, two or three additional carbon atoms are optionally replaced by a heteroatom selected from oxygen, sulfur or nitrogen heteroatom. Examples of this type are pyrrole, pyridine, oxazole, thiazole and oxazine. Additional nitrogen atoms may be present together with the first nitrogen and oxygen or sulfur, giving, e.g., thiadiazole. Examples include the following.

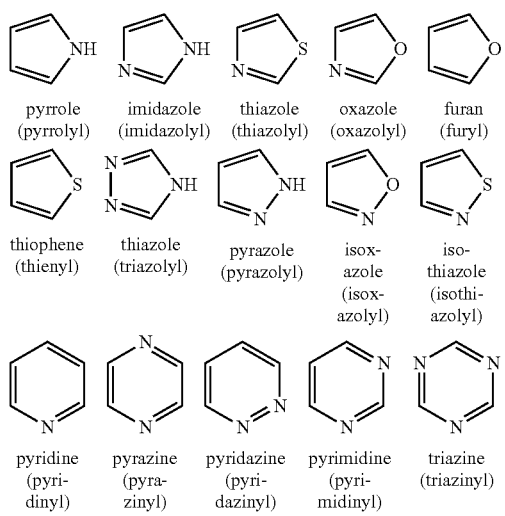

pyrrole (pyrrolyl), imidazole (imidazolyl), thiazole (thiazolyl), oxazole (oxazolyl), furan (furyl)

thiophene (thienyl), thiazole (triazolyl), pyrazole (pyrazolyl), isoxazole (isoxazolyl), isothiazole (isothiazolyl)

pyridine (pyridinyl), pyrazine (pyrazinyl), pyridazine (pyridazinyl), pyrimidine (pyrimidinyl), triazine (triazinyl)

The heteroaryl or heteroaromatic group can be optionally substituted with one or more substituent selected from halogen, haloalkyl, alkyl, alkoxy, hydroxy, carboxyl derivatives, amido, amino, alkylamino, dialkylamino. Functional oxygen and nitrogen groups on the heterocyclic or heteroaryl group can be protected as necessary or desired. Suitable protecting groups are well known to those skilled in the art, and include trimethylsilyl, dimethylhexylsilyl, t-butyldimethylsilyl, and t-butyl-diphenylsilyl, trityl or substituted trityl, alkyl groups, acyl groups such as acetyl and propionyl, methanesulfonyl, and p-toluenylsulfonyl.

"Heteroarylium" refers to heteroaryl groups bearing a quaternary nitrogen atom and thus a positive charge. Examples include the following.

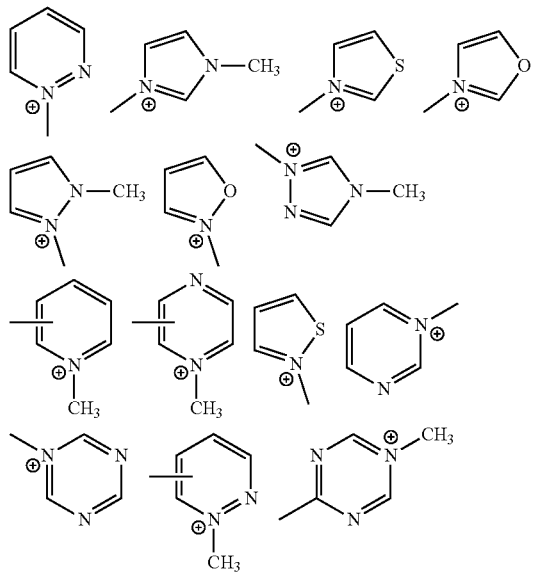

When a charge is shown on a particular nitrogen atom in a ring which contains one or more additional nitrogen atoms, it is understood that the charge may reside on a different nitrogen atom in the ring by virtue of charge resonance that occurs.

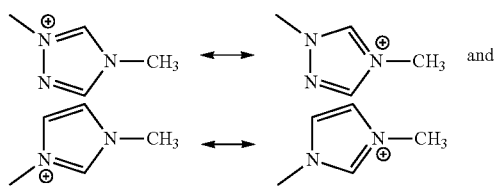

The term "heterocycloalkyl" refers to a cycloalkyl group (nonaromatic) in which one of the carbon atoms in the ring is replaced by a heteroatom selected from O, S or N, and in which up to three additional carbon atoms may be replaced by heteroatoms.

The terms "quaternary nitrogen" and "positive charge" refer to tetravalent, positively charged nitrogen atoms including, e.g., the positively charged nitrogen in a tetraalkylammonium group (e.g. tetramethylammonium), heteroarylium, (e.g., N-methyl-pyridinium), basic nitrogens which are protonated at physiological pH, and the like. Cationic groups thus encompass positively charged nitrogen-containing groups, as well as basic nitrogens which are protonated at physiologic pH.

The term "heteroatom" refers to oxygen, sulfur, nitrogen, phosphorus, and selenium, selected on an independent basis.

Halogen and "halo", as used herein, includes bromine, chlorine, fluorine and iodine.

The term acyl refers to a carboxylic acid ester in which the non-carbonyl moiety of the ester group is selected from straight, branched, or cyclic alkyl, alkoxyalkyl including methoxymethyl, aralkyl including benzyl, aryloxyalkyl such as phenoxymethyl, aryl including phenyl optionally substituted with halogen, C1 to C4 alkyl or C1 to C4 alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters typically include a phenyl group.

"Carboxylate anion" refers to a negatively charged group —COO.

"Guanidinyl" refers to the group: $H_2NC(NH)NH$—.
"Carbamimidoyl" refers to the group: $H_2NC(NH)$—.
"Ureido" refers to the group: $H_2NC(O)NH$—.

When a group is termed "substituted", unless otherwise indicated, this means that the group contains from 1 to 4 substituents thereon. When a functional group is termed "protected", this means that the group is in modified form to preclude undesired side reactions at the protected site, and unless otherwise defined refers to a group that is added to an oxygen, nitrogen, or phosphorus atom to prevent its further reaction or for other purposes.

In some of the carbapenem compounds of the present invention, M is a readily removable carboxyl protecting group, and/or P represents a hydroxyl which is protected by a hydroxyl-protecting group. Such protecting groups are used to protectively block the hydroxyl or carboxyl group during the synthesis procedures and are readily removable by procedures that will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation.

A wide variety of oxygen and nitrogen protecting groups are known to those skilled in the art of organic synthesis. Suitable protecting groups for the compounds of the present invention will be recognized from the present application taking into account the level of skill in the art, and with reference to standard textbooks, such as Greene, T. W. and Wuts, P. M., Protective Groups in Organic Synthesis, 3$^{rd}$ Ed., Wiley, New York (1991). Examples of carboxyl protecting groups include allyl, benzhydryl, 2-naphthylmethyl, benzyl (Bn), silyl such as t-butyldimethylsilyl (TBDMS), phenacyl, p-methoxybenzyl, o-nitrobenzyl, p-methoxyphenyl, p-nitrobenzyl, 4-pyridylmethyl and t-butyl. Examples of suitable C-6 hydroxyethyl protecting groups include triethylsilyl (TES), t-butyldimethylsilyl (TBDMS), o-nitrobenzyloxycarbonyl (ONB), p-nitrobenzyloxycarbonyl (PNB), benzyloxycarbonyl (CBz), allyloxycarbonyl (Alloc), t-butyloxycarbonyl (Boc), 2,2,2-trichloroethyloxycarbonyl (Troc), and the like.

As referred to herein, the term "pharmaceutically acceptable salts" include salts that retain the desired biological activity of the parent compound and do not impart undesired toxicological effects. In certain embodiments, the salt form is such that the group —COOH of the parent compound is replaced with —COOM, where M is a cation. In certain embodiments, the cation is a metal cation or ammonium cation. Exemplary cations include sodium; potassium; magnesium; zinc; calcium; ammonium or alkylammonium cations such as tetramethylammonium, tetrabutylammonium, choline, triethylhydroammonium, meglumine, and triethanolhydroammonium; and calcium polyamines such as spermine and spermidine.

In certain embodiments, the salts are formed from reactions with compounds which comprise elemental anions such as chloride, bromide, and iodide. In certain embodiments, the salts can also include acid addition salts, for example, salts derived from inorganic or organic acids.

Included among such salts are the following: acetate, adipate, alginate, ascorbic acid, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, gluconic acid, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitric acid, oxalate, palmitic acid, pamoate, pectinate, persulfate, 3-phenylpropionate, phosphoric acid, picrate, pivalate, polygalacturonic acid; polyglutamic acid, propionate, p-toluenesulfonic acid, succinate, sulfuric acid, tannic acid, tartrate, thiocyanate, tosylate and undecanoate.

The term "prodrug" includes a compound that, when administered to an animal, is converted under physiological conditions to a compound of the invention, for example a pharmaceutically acceptable ester.

The pharmaceutically acceptable esters are such as would be readily apparent to a medicinal chemist, and include, for example, those described in detail in U.S. Pat. No. 4,309,438. Included within such pharmaceutically acceptable esters are those, which are hydrolyzed under physiological conditions, such as pivaloyloxymethyl, acetoxymethyl, phthalidyl, indanyl and methoxymethyl. These are also referred to as "biolabile esters", which are biologically hydrolysable. In certain embodiments, the ester form is such that the group —COOH of the parent compound is replaced with —COOM, where M is, for example, an alkoxyalkyl, alkylcarbonyloxyalkyl, alkoxycarbonyloxyalkyl, cycloalkoxyalkyl, alkenyloxyalkyl, aryloxyalkyl, alkoxyaryl, alkylthioalkyl, cycloalkylthioalkyl, alkenylthioalkyl, arylthioalkyl or alkylthioaryl group. These groups can be substituted in the alkyl or aryl portions thereof with acyl or halo groups. The following M species are examples of biolabile ester forming moieties: acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl and (2-oxo methyl-1,3-dioxolenyl)methyl.

The term "host", as used herein, refers to a unicellular or multicellular organism in which the bacteria can replicate, including cell lines and animals. Alternatively, the host can be carrying a part of the bacterial particles, whose replication and/or function can be altered by the compounds of the present invention. The term host refers to infected cells, cells transfected with all or part of the bacteria and animals, such as, primates (including chimpanzees) and, in one embodiment, the host is a human. Veterinary applications are also encompassed by the present invention.

The term "treatment" as used herein, includes an approach for obtaining beneficial or desired results including clinical results, including alleviation of symptoms, diminishment of extent of disease, stabilization (i.e., not worsening) state of disease, preventing spread of disease, preventing or reducing occurrence or recurrence of disease, delay or slowing of disease progression, and reduction of incidence of disease or symptoms. As used herein, the phrase "anti-bacterially effective amount" means an amount effective for treating the bacterial infection.

Compounds

In embodiments, the compound has the structure of Formula (I):

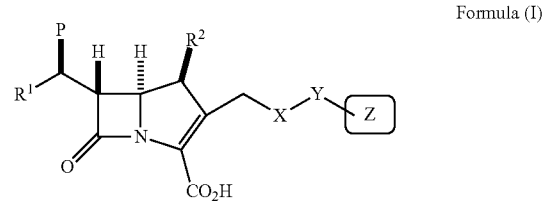

Formula (I)

or a pharmaceutically acceptable salt or prodrug thereof, wherein:
  $R^1$ and $R^2$ are each independently selected from H or alkyl;
  P is H, OH, halogen, or hydroxyl protected by a hydroxyl protecting group;
  X is (1) an acylic or cyclic alkyl amino based linker, optionally substituted by one or more substituents selected from the group consisting of alkyl, haloalkyl, OR, CN, CONRR', SR, or NRR' or (2) a quaternary ammonium cation based linker, optionally substituted by one or more substituents selected from the group consisting of alkyl, haloalkyl, OR, CN, CONR$_2$, SR, or NRR';
  Y is a divalent —NR(C=O)—(CR$_2$)$_n$— or —(C=O) NR—(CR$_2$)$_n$— group, wherein n is 0, 1, or 2;
  R and R' are each independently selected from H or alkyl; and
  Z is an aromatic or heteroaromatic ring, substituted by one or more substituents selected from the group consisting of alkyl, haloalkyl, OH, halogen, or hydroxyl protected by a hydroxyl protecting group.

In certain embodiments of any of the Formulas herein, $R^1$, $R^2$ and $R^3$ are each H. In certain embodiments of any of the Formulas herein, $R^1$, $R^2$ and $R^3$ are not H. In certain embodiments of any of the Formulas herein, $R^1$, $R^2$ and $R^3$ are each alkyl, for example methyl, ethyl or propyl. In certain embodiments of any of the Formulas herein, $R^1$, $R^2$ and $R^3$ are each methyl.

In certain embodiments of any of the Formulas herein, —COOH is replaced with —COOM, wherein M is a cation.

In certain embodiments, X is the bivalent group —N($R^3$)-Q-, wherein N is bonded to the carbapenem methylene group; $R^3$ is H or alkyl; Q is —$(CR_2)_p$—W—$(CR_2)_q$—, optionally substituted by one or more substituents selected from the group consisting of alkyl, haloalkyl, OR, CN, CONRR', SR, or NRR'; p and q are each independently 0, 1, or 2; and W is absent, —CONR—, or —NRCO—.

In certain embodiments of any of the Formulas herein, Y is —NR(C=O)—$(CR_2)_n$—, for example —NH(C=O)—$(CH_2)_n$—. In certain embodiments of any of the Formulas herein, Y is —(C=O)NR—$(CR_2)_n$—, for example —(C=O)NH—$(CH_2)_n$—. In certain embodiments of any of the Formulas herein, Y is a divalent —NH(C=O)—$(CH_2)_n$— or —(C=O)NH—$(CH_2)_n$— group. In certain embodiments, n is 0. In certain embodiments, n is 1. In certain embodiments, n is 2.

In certain embodiments of any of the Formulas herein, Z is a substituted aromatic ring, for example a substituted phenyl. In certain embodiments of any of the Formulas herein, Z is a substituted heteroaromatic ring, for example a substituted N-containing heterocycle or a substituted O-containing heterocycle, such as a substituted N-hydroxy-4-pyridonyl or substituted 4-pyranonyl. In certain embodiments, the phenyl is substituted with one or more substituents selected from the group consisting of hydroxy; halo, such as fluoro, chloro, bromo, iodo; alkoxy, such as methoxy or ethoxy; alkylcarbonyloxy, such as acetoxy or pivaloyloxy. In embodiments, the phenyl is substituted with one to three substituents selected from the group consisting of hydroxyl, fluoro, chloro, or methoxy.

In certain embodiments of any of the Formulas herein, R is H. In certain embodiments of any of the Formulas herein, R is alkyl, for example methyl, ethyl, or propyl.

In embodiments, the compound has the structure of Formula (Ia):

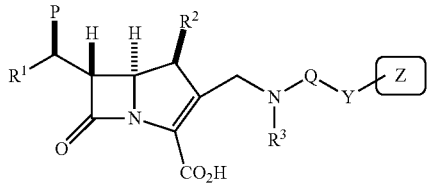

Formula (Ia)

or a pharmaceutically acceptable salt or prodrug thereof, wherein:
$R^1$, $R^2$ and $R^3$ are each independently selected from H or alkyl;
P is H, OH, halogen, or hydroxyl protected by a hydroxyl protecting group;
Q is —$(CR_2)_p$—W—$(CR_2)_q$—, optionally substituted by one or more substituents selected from the group consisting of alkyl, haloalkyl, OR, CN, CONRR', SR, or NRR', p and q are each independently 0, 1, or 2;
W is absent, —CONR—, or —NRCO—;
Y is a divalent —NR(C=O)—$(CR_2)_n$— or —(C=O)NR—$(CR_2)_n$— group, n is 0, 1, or 2;
R and R' are each independently selected from H or alkyl; and Z is an aromatic or heteroaromatic ring, substituted by one or more substituents selected from the group consisting of alkyl, haloalkyl, OH, halogen, or hydroxyl protected by a hydroxyl protecting group.

In certain embodiments, $R^3$ is alkyl, for example methyl, ethyl, propyl, or butyl. In certain embodiments, $R^3$ is H. In a particular embodiment, $R^3$ is methyl.

In certain embodiments, at least one of p or q is not 0.

In certain embodiments, Q is —$(CR_2)_p$—$(CR_2)_q$—, optionally substituted by one or more substituents selected from the group consisting of alkyl, haloalkyl, OR, CN, CONRR', SR, or NRR', p and q are each independently 0, 1, or 2. In certain embodiments, Q is $CR_2$, $CR_2CR_2$, $CR_2CR_2CR_2$, or $CR_2CR_2CR_2CR_2$; wherein each R is independently selected from H or alkyl.

In certain embodiments, Q is $CH_2$, $CH_2CH_2$, $CH_2CH_2CH_2$, or $CH_2CH_2CH_2CH_2$. In certain embodiments, Q is a methyl, ethyl, propyl, or butyl group.

In certain embodiments, Q is —$(CR_2)_p$—$CONR_2$—$(CR_2)_q$—, optionally substituted by one or more substituents selected from the group consisting of alkyl, haloalkyl, OR, CN, CONRR', SR, or NRR', p and q are each independently 0, 1, or 2. In certain embodiments, Q $CR_2$—$CONR_2$—$CR_2$, $CR_2$—$CONR_2$—$CR_2CR_2$, or $CR_2CR_2$—$CONR_2$—$CR_2CR_2$; wherein each R is independently selected from H or alkyl. In certain embodiments, Q is $CH_2$—$CONH_2$—$CH_2$, $CH_2$—$CONH_2$—$CH_2CH_2$, or $CH_2CH_2$—$CONH_2$—$CH_2CH_2$.

In one embodiment, the compound of Formula (Ia) is selected from the group consisting of:

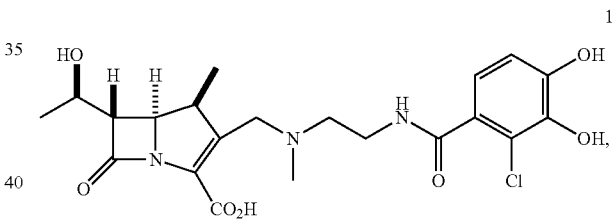

1

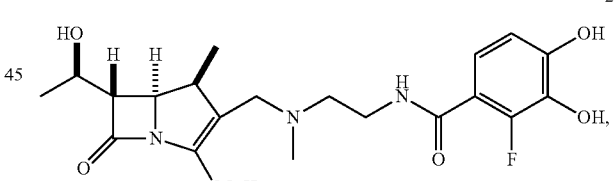

2

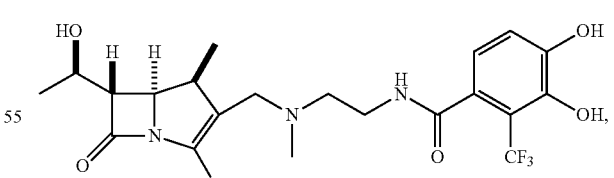

3

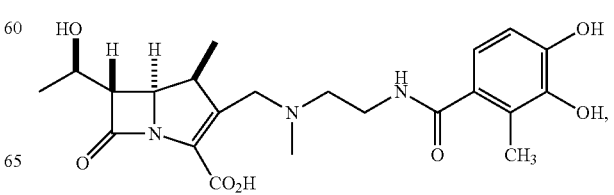

4

5
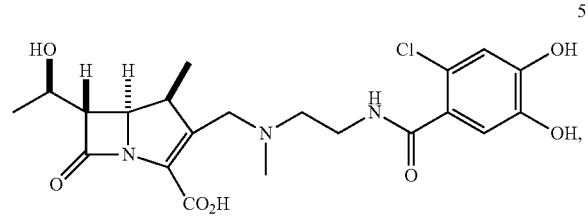
6
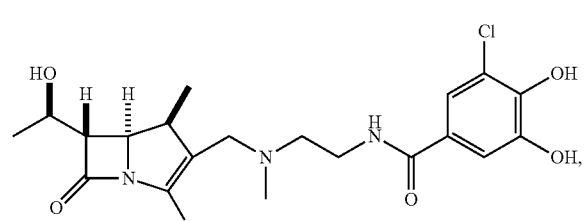
7
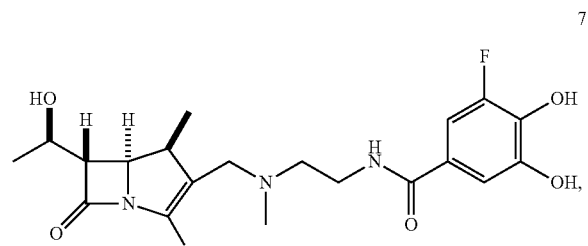
8
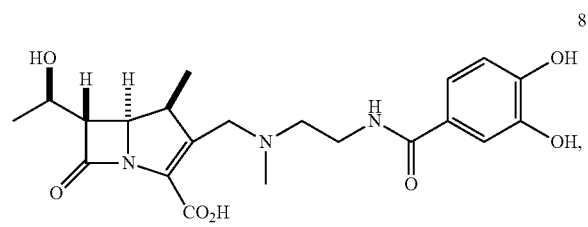
9
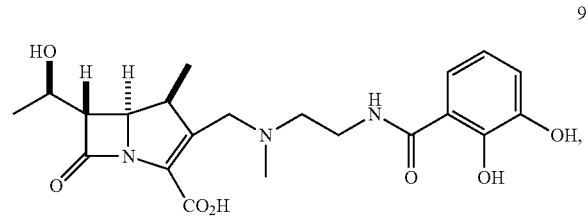
10
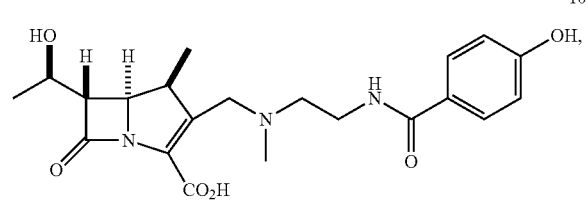
11
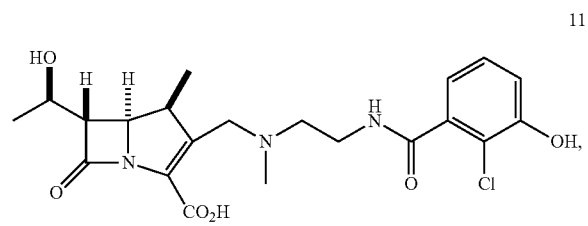
12
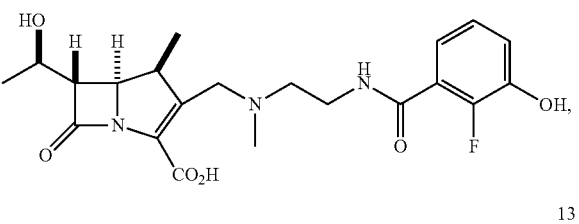
13
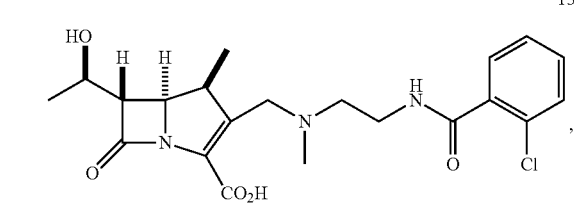
14
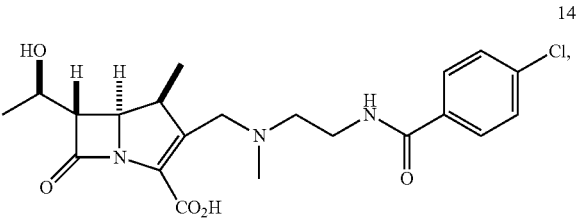
15
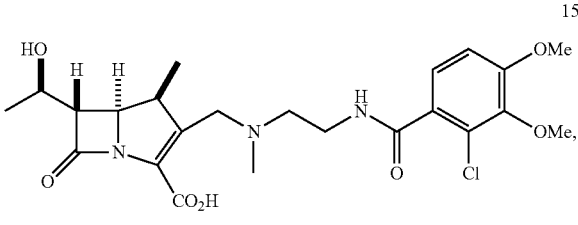
16
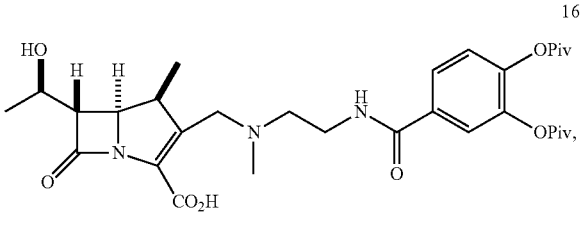
17
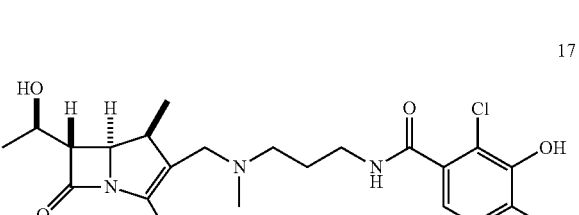
18
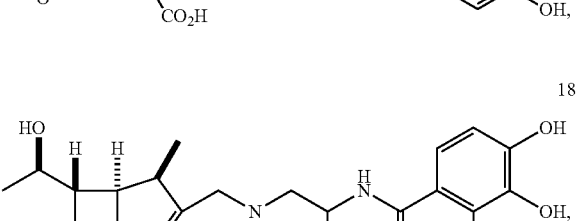

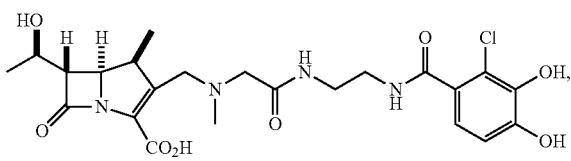

19

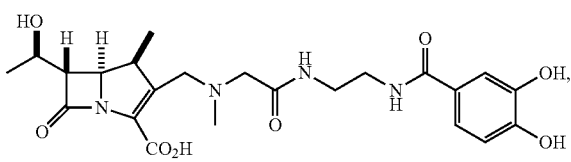

20

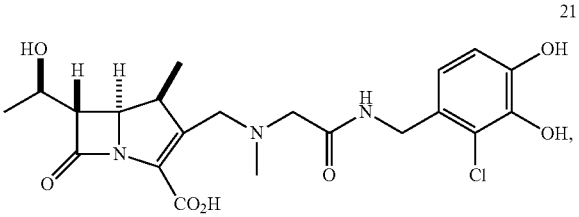

21

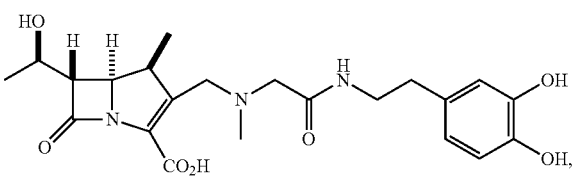

22

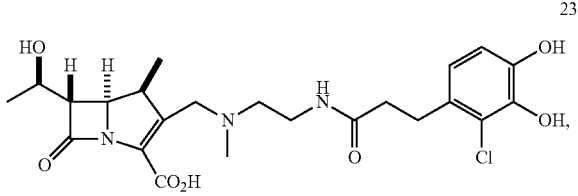

23

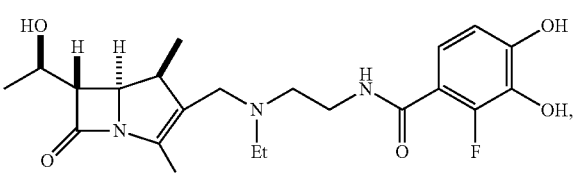

24

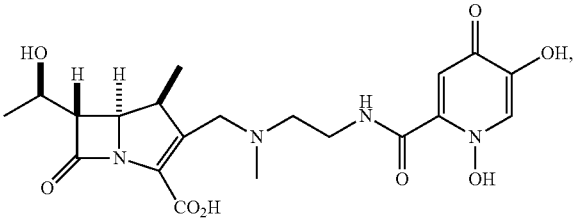

25

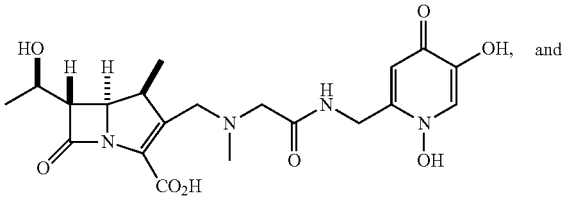

26

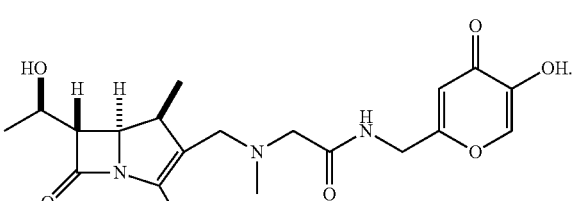

27

In certain embodiments, the compound has the structure of Formula (Ib):

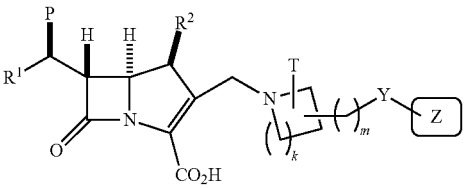

Formula (Ib)

or a pharmaceutically acceptable salt or prodrug thereof, wherein:

$R^1$ and $R^2$ are each independently selected from H or alkyl;

P is H, OH, halogen, or hydroxyl protected by a hydroxyl protecting group;

T is absent, alkyl, haloalkyl, OR, CN, CONRR', SR, or NRR';

Y is a divalent —NR(C=O)—$(CR_2)_n$— or —(C=O)NR—$(CR_2)_n$— group, n is 0, 1, or 2;

k is 1, 2, or 3;

m is 0, 1, or 2;

R and R' are each independently selected from H or alkyl; and

Z is an aromatic or heteroaromatic ring, substituted by one or more substituents selected from the group consisting of alkyl, haloalkyl, OH, halogen, or hydroxyl protected by a hydroxyl protecting group.

In one embodiment, the compound of Formula (Ib) is selected from the group consisting of:

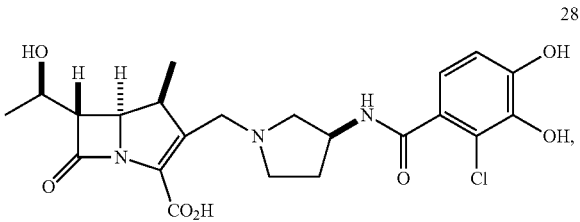

28

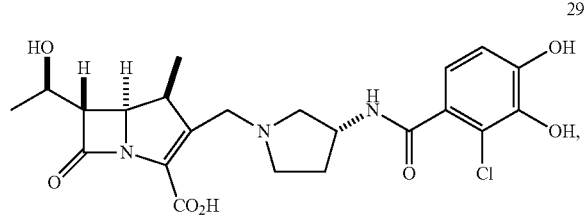

29

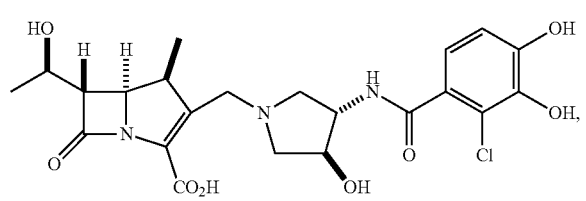

30

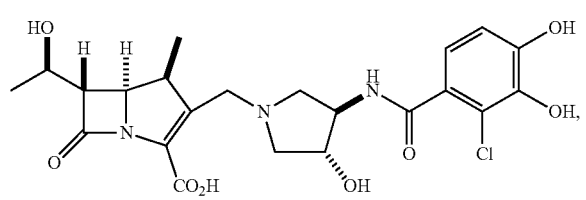

31

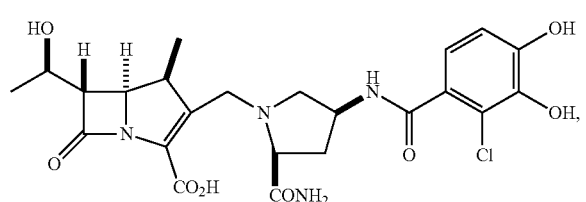

32

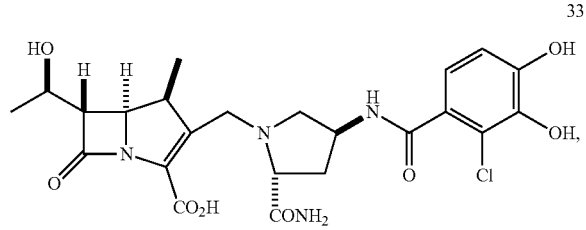

33

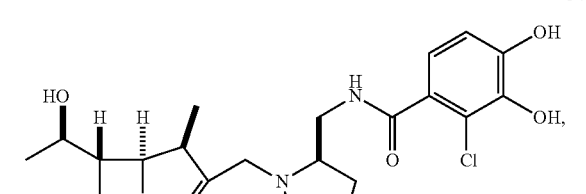

34

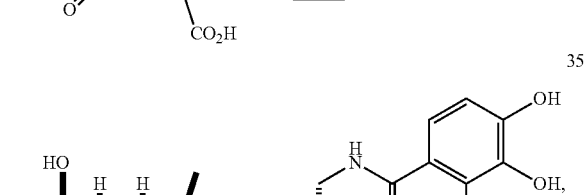

35

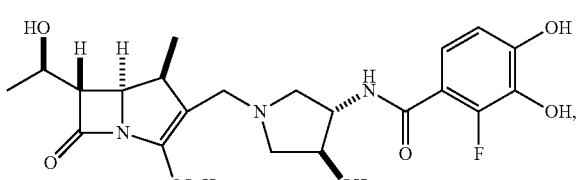

36

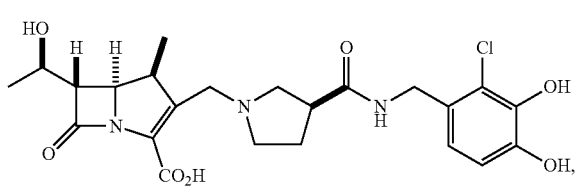

37

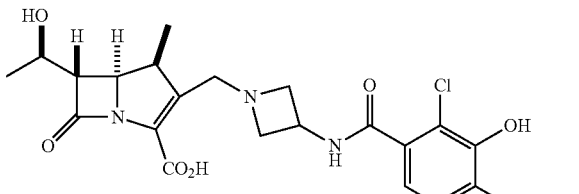

38

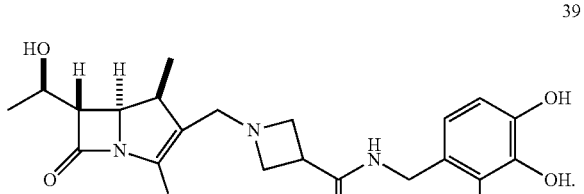

39

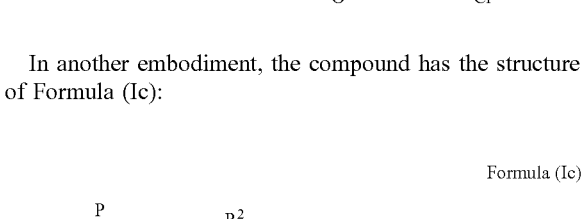

In another embodiment, the compound has the structure of Formula (Ic):

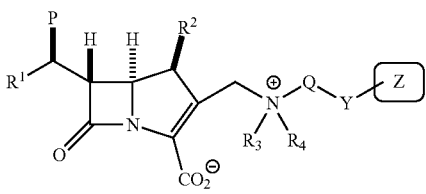

Formula (Ic)

or a pharmaceutically acceptable salt or prodrug thereof, wherein:

$R^1$, $R^2$, $R^3$, and $R^4$ are each independently selected from H or alkyl;

P is H, OH, halogen, or hydroxyl protected by a hydroxyl protecting group;

Q is —(CR$_2$)$_p$—W—(CR$_2$)$_q$—, optionally substituted by one or more substituents selected from the group consisting of alkyl, haloalkyl, OR, CN, CONRR', SR, or NRR', p and q are each independently 0, 1, or 2;

W is absent, —CONR—, or —NRCO—;

Y is a divalent —NR(C═O)—(CR$_2$)$_n$— or —(C═O)NR—(CR$_2$)$_n$— group, n is 0, 1, or 2;

R and R' are each independently selected from H or alkyl; and

Z is an aromatic or heteroaromatic ring, substituted by one or more substituents selected from the group consisting of alkyl, haloalkyl, OH, halogen, or hydroxyl protected by a hydroxyl protecting group.

In one embodiment, the compound of Formula (Ic) is selected from the group consisting of:

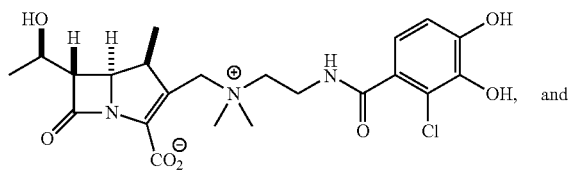
40

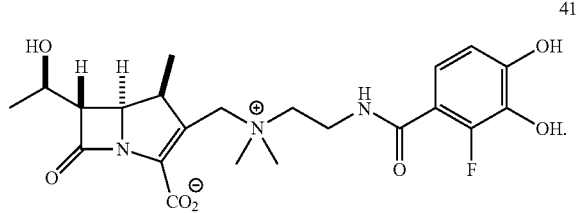
41

In another embodiment, the compound has the structure of Formula (Id):

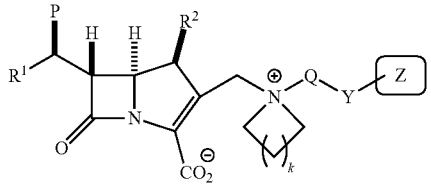

Formula (Id)

or a pharmaceutically acceptable salt or prodrug thereof, wherein:

$R^1$ and $R^2$ are each independently selected from H or alkyl;

P is H, OH, halogen, or hydroxyl protected by a hydroxyl protecting group;

Q is —$(CR_2)_p$—W—$(CR_2)_q$—, optionally substituted by one or more substituents selected from the group consisting of alkyl, haloalkyl, OR, CN, CONRR', SR, or NRR', p and q are each independently 0, 1, or 2;

W is absent, —CONR—, or —NRCO—;

Y is a divalent —NR(C=O)—$(CR_2)_n$— or —(C=O)NR—$(CR_2)_n$— group, n is 0, 1, or 2;

k is 1, 2, or 3;

R and R' are each independently selected from H or alkyl; and

Z is an aromatic or heteroaromatic ring, substituted by one or more substituents selected from the group consisting of alkyl, haloalkyl, OH, halogen, or hydroxyl protected by a hydroxyl protecting group.

In one embodiment, the compound is:

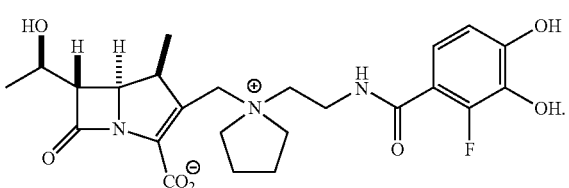
42

In another embodiment, the compound has the structure of Formula Ie:

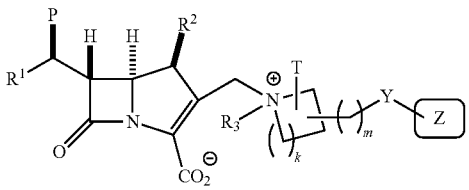

Formula (Ie)

or a pharmaceutically acceptable salt or prodrug thereof, wherein:

$R^1$, $R^2$, and $R^3$ are each independently selected from H or alkyl;

P is H, OH, halogen, or hydroxyl protected by a hydroxyl protecting group;

T is absent, alkyl, haloalkyl, OR, CN, CONRR', SR, or NRR';

Y is a divalent —NR(C=O)—$(CR_2)_n$— or —(C=O)NR—$(CR_2)_n$— group, n is 0, 1, or 2;

k is 1, 2, or 3;

m is 0, 1, or 2;

R and R' are each independently selected from H or alkyl; and

Z is an aromatic or heteroaromatic ring, substituted by one or more substituents selected from the group consisting of alkyl, haloalkyl, OH, halogen, or hydroxyl protected by a hydroxyl protecting group.

In one embodiment, the compound is:

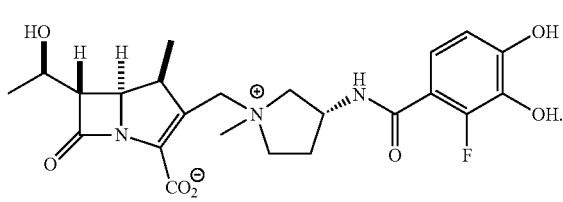
43

In certain embodiments, the compound has the structure of Formula (IIa) or (IIb):

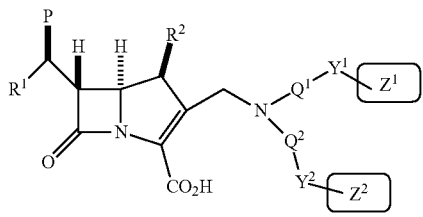

Formula (IIa)

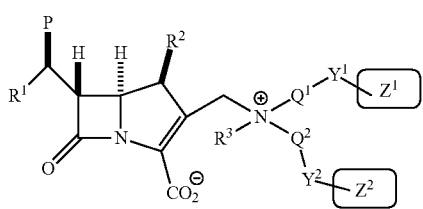

Formula (IIb)

or a pharmaceutically acceptable salt or prodrug thereof, wherein:
- $R^1$ and $R^2$ are each independently selected from H or alkyl;
- P is H, OH, halogen, or hydroxyl protected by a hydroxyl protecting group;
- $Q^1$ and $Q^2$ are each independently selected from a divalent —$(CR_2)_p$—W—$(CR_2)_q$—, optionally substituted by one or more substituents selected from the group consisting of alkyl, haloalkyl, OR, CN, CONRR', SR, or NRR';
- p and q are each independently 0, 1, or 2, and at least one of p or q is not 0;
- W is absent, —CONR—, or —NRCO—;
- $Y^1$ and $Y^2$ are each independently selected from a divalent —NR(C=O)—$(CR_2)_n$— or —(C=O)NR—$(CR_2)_n$— group, wherein n is 0, 1, or 2;
- $Z^1$ and $Z^2$ are each independently selected from an aromatic or heteroaromatic ring, substituted by one or more substituents selected from the group consisting of alkyl, haloalkyl, OH, halogen, or hydroxyl protected by a hydroxyl protecting group; and
- $R^3$ in Formula (IIb) is H or alkyl.

In certain embodiments of any of the Formulas herein, $R^1$ and $R^2$ are each H. In certain embodiments of any of the Formulas herein, $R^1$ and $R^2$ are not H. In certain embodiments of any of the Formulas herein, $R^1$ and $R^2$ are each alkyl, for example methyl, ethyl or propyl. In certain embodiments of any of the Formulas herein, $R^1$ and $R^2$ are each methyl.

In certain embodiments of any of the Formulas herein, $R^3$ is H. In certain embodiments of any of the Formulas herein, $R^3$ is not H. In certain embodiments of any of the Formulas herein, $R^3$ is alkyl, for example methyl, ethyl or propyl. In certain embodiments of any of the Formulas herein, $R^3$ is each methyl.

In certain embodiments of any of the Formulas herein, —COOH is replaced with —COOM, wherein M is a cation.

In certain embodiments of any of the Formulas herein, $Y^1$ is —NR(C=O)—$(CR_2)_n$—, for example —NH(C=O)—$(CH_2)_n$—. In certain embodiments of any of the Formulas herein, $Y^1$ is —(C=O)NR—$(CR_2)_n$—, for example —(C=O)NH—$(CH_2)_n$—. In certain embodiments of any of the Formulas herein, $Y^1$ is a divalent —NH(C=O)—$(CH_2)_n$— or —(C=O)NH—$(CH_2)_n$— group. In certain embodiments, n is 0. In certain embodiments, n is 1. In certain embodiments, n is 2.

In certain embodiments of any of the Formulas herein, $Y^2$ is —NR(C=O)—$(CR_2)_n$—, for example —NH(C=O)—$(CH_2)_n$—. In certain embodiments of any of the Formulas herein, $Y^2$ is —(C=O)NR—$(CR_2)_n$—, for example —(C=O)NH—$(CH_2)_n$—. In certain embodiments of any of the Formulas herein, $Y^2$ is a divalent —NH(C=O)—$(CH_2)_n$— or —(C=O)NH—$(CH_2)_n$— group. In certain embodiments, n is 0. In certain embodiments, n is 1. In certain embodiments, n is 2.

In certain embodiments of any of the Formulas herein, $Z^1$ is a substituted aromatic ring, for example a substituted phenyl. In certain embodiments of any of the Formulas herein, $Z^1$ is a substituted heteroaromatic ring, for example a substituted N-containing heterocycle or a substituted O-containing heterocycle, such as a substituted N-hydroxy-4-pyridonyl or substituted 4-pyranonyl. In certain embodiments, the phenyl is substituted with one or more substituents selected from the group consisting of hydroxy; halo, such as fluoro, chloro, bromo, iodo; alkoxy, such as methoxy or ethoxy; alkylcarbonyloxy, such as acetoxy or pivaloyloxy. In embodiments, the phenyl is substituted with one to three substituents selected from the group consisting of hydroxyl, fluoro, chloro, or methoxy.

In certain embodiments of any of the Formulas herein, $Z^2$ is a substituted aromatic ring, for example a substituted phenyl. In certain embodiments of any of the Formulas herein, $Z^2$ is a substituted heteroaromatic ring, for example a substituted N-containing heterocycle or a substituted O-containing heterocycle, such as a substituted N-hydroxy-4-pyridonyl or substituted 4-pyranonyl. In certain embodiments, the phenyl is substituted with one or more substituents selected from the group consisting of hydroxy; halo, such as fluoro, chloro, bromo, iodo; alkoxy, such as methoxy or ethoxy; alkylcarbonyloxy, such as acetoxy or pivaloyloxy. In embodiments, the phenyl is substituted with one to three substituents selected from the group consisting of hydroxyl, fluoro, chloro, or methoxy.

In certain embodiments of any of the Formulas herein, R is H. In certain embodiments of any of the Formulas herein, R is alkyl, for example methyl, ethyl, or propyl.

In certain embodiments, $Q^1$ is —$(CR_2)_p$—$(CR_2)_q$—, optionally substituted by one or more substituents selected from the group consisting of alkyl, haloalkyl, OR, CN, CONRR', SR, or NRR', p and q are each independently 0, 1, or 2. In certain embodiments, $Q^1$ is $CR_2$, $CR_2CR_2$, $CR_2CR_2CR_2$, or $CR_2CR_2CR_2CR_2$; wherein each R is independently selected from H or alkyl.

In certain embodiments, $Q^1$ is $CH_2$, $CH_2CH_2$, $CH_2CH_2CH_2$, or $CH_2CH_2CH_2CH_2$. In certain embodiments, $Q^1$ is a methyl, ethyl, propyl, or butyl group.

In certain embodiments, $Q^1$ is —$(CR_2)_p$—$CONR_2$—$(CR_2)_q$—, optionally substituted by one or more substituents selected from the group consisting of alkyl, haloalkyl, OR, CN, CONRR', SR, or NRR', p and q are each independently 0, 1, or 2. In certain embodiments, $Q^1$ is $CR_2$—$CONR_2$—$CR_2$, $CR_2$—$CONR_2$—$CR_2CR_2$, or $CR_2CR_2$—$CONR_2$—$CR_2CR_2$; wherein each R is independently selected from H or alkyl. In certain embodiments, $Q^1$ is $CH_2$—$CONH_2$—$CH_2$, $CH_2$—$CONH_2$—$CH_2CH_2$, or $CH_2CH_2$—$CONH_2$—$CH_2CH_2$.

In certain embodiments, $Q^2$ is —$(CR_2)_p$—$(CR_2)_q$—, optionally substituted by one or more substituents selected from the group consisting of alkyl, haloalkyl, OR, CN, CONRR', SR, or NRR', p and q are each independently 0, 1, or 2. In certain embodiments, $Q^2$ is $CR_2$, $CR_2CR_2$, $CR_2CR_2CR_2$, or $CR_2CR_2CR_2CR_2$; wherein each R is independently selected from H or alkyl.

In certain embodiments, $Q^2$ is $CH_2$, $CH_2CH_2$, $CH_2CH_2CH_2$, or $CH_2CH_2CH_2CH_2$. In certain embodiments, $Q^2$ is a methyl, ethyl, propyl, or butyl group.

In certain embodiments, $Q^2$ is —$(CR_2)_p$—$CONR_2$—$(CR_2)_q$—, optionally substituted by one or more substituents selected from the group consisting of alkyl, haloalkyl, OR, CN, CONRR', SR, or NRR', p and q are each independently 0, 1, or 2. In certain embodiments, $Q^2$ is $CR_2$—$CONR_2$—$CR_2$, $CR_2$—$CONR_2$—$CR_2CR_2$, or $CR_2CR_2$—$CONR_2$—$CR_2CR_2$; wherein each R is independently selected from H or alkyl. In certain embodiments, $Q^2$ is $CH_2$—$CONH_2$—$CH_2$, $CH_2$—$CONH_2$—$CH_2CH_2$, or $CH_2CH_2$—$CONH_2$—$CH_2CH_2$.

In certain embodiments, $Q^1$ and $Q^2$ can be the same or different and are each selected methyl, ethyl, propyl, or butyl. In certain embodiments, $Q^1$ and $Q^2$ are the same. In certain embodiments, both $Q^1$ and $Q^2$ are ethyl. In certain embodiments, both $Q^1$ and $Q^2$ are propyl. In certain embodiments, $Q^1$ and $Q^2$ are different. In certain embodiments, $Q^1$ is ethyl and $Q^2$ is propyl. In certain embodiments, $Q^1$ is propyl and $Q^2$ is butyl.

In certain embodiments of any of the Formulas herein, $Q^1$ and $Q^2$ are independently selected from $C_2$ to $C_4$ alkyl groups and W is absent. In certain embodiments, $Q^1$ and $Q^2$ are both ethyl groups and W is absent. In certain embodiments, $Q^1$ and $Q^2$ are both propyl groups and W is absent. In certain embodiments, $Q^1$ and $Q^2$ are both butyl groups and W is absent. In certain embodiments, $Q^1$ is an ethyl group, $Q^2$ is a propyl group and W is absent. In certain embodiments, $Q^1$ is an propyl group, $Q^2$ is a butyl group and W is absent. In certain embodiments, $Q^1$ is an ethyl group, $Q^2$ is a butyl group and W is absent.

In certain embodiments, $Y^1$ and $Y^2$ can be the same or different. In certain embodiments, both $Y^1$ and $Y^2$ are —N(H)-ethyl. In certain embodiments, both $Q^1$ and $Q^2$ are propyl. In certain embodiments, $Q^1$ and $Q^2$ are different. In certain embodiments, $Q^1$ is ethyl and $Q^2$ is propyl. In certain embodiments, $Q^1$ is propyl and $Q^2$ is butyl.

In certain embodiments of any of the Formulas herein, $Y^1$ and $Y^2$ are both —NR(C=O)—$(CR_2)_n$—, for example —NH(C=O)—$(CH_2)_n$—. In certain embodiments of any of the Formulas herein, $Y^1$ and $Y^2$ are both —(C=O)NR—$(CR_2)_n$—, for example —(C=O)NH—$(CH_2)_n$—. In certain embodiments of any of the Formulas herein, $Y^1$ and $Y^2$ are a divalent —NH(C=O)—$(CH_2)_n$— or —(C=O)NH—$(CH_2)_n$— group. In certain embodiments of any of the Formulas herein, $Y^1$ and $Y^2$ are a divalent —NH(C=O)— group. In certain embodiments of any of the Formulas herein, $Y^1$ and $Y^2$ are a divalent —(C=O)NH— group. In certain embodiments, n is 0. In certain embodiments, n is 1. In certain embodiments, n is 2.

In certain embodiments, $Z^1$ and $Z^2$ can be the same or different. In certain embodiments, $Z^1$ and $Z^2$ are the same. In certain embodiments, both $Z^1$ and $Z^2$ are substituted phenyl groups. In certain embodiments, $Z^1$ and $Z^2$ are different. In certain embodiments, the phenyl groups are substituted with the same substituents.

In certain embodiments, the compound is a compound of Formula IIa. In certain embodiments, the compound is a compound of Formula IIb.

In one embodiment, the compound of Formula (IIa) is selected from the group consisting of:

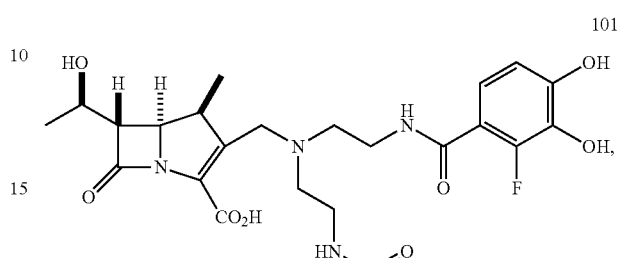

101

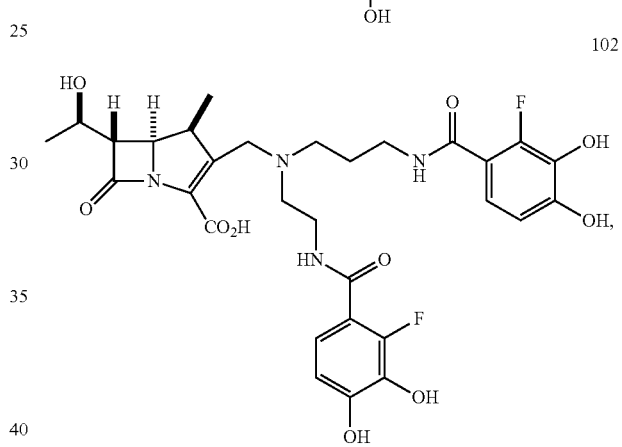

102

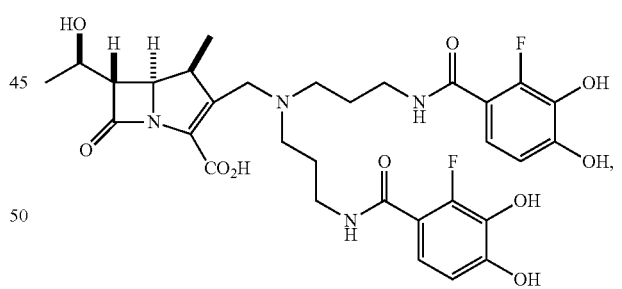

103

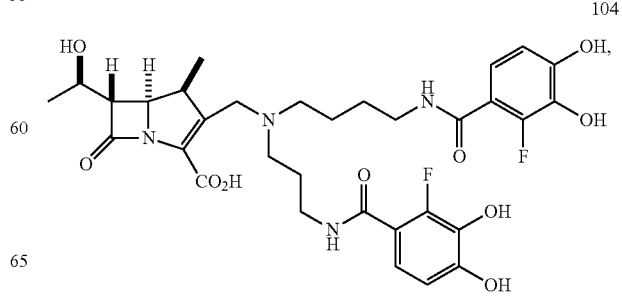

104

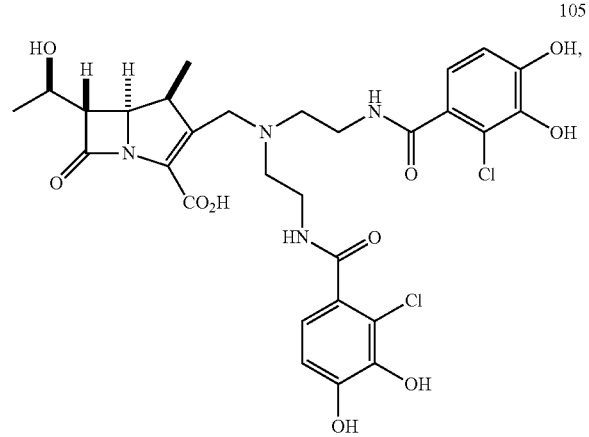
105
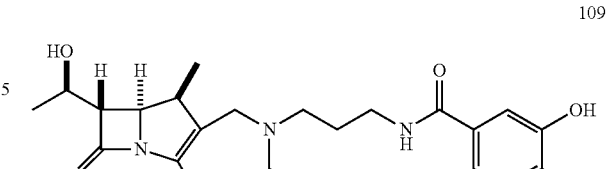
109
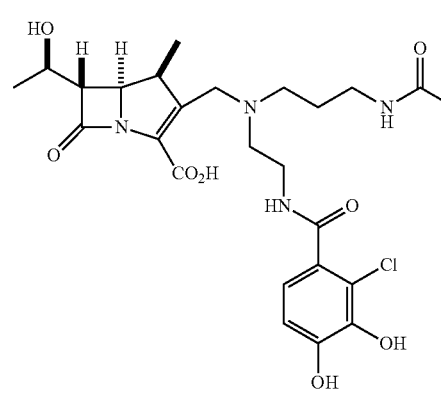
106
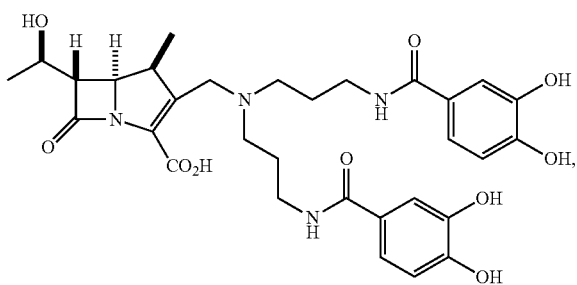
110
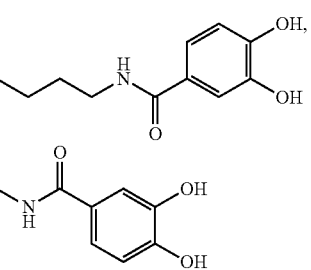
111
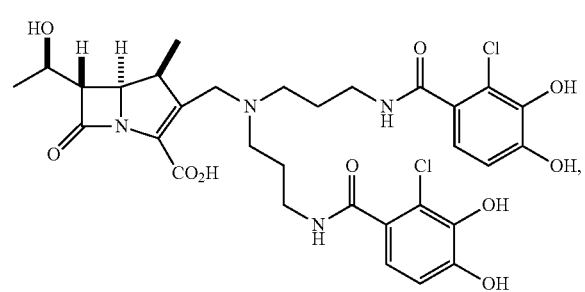
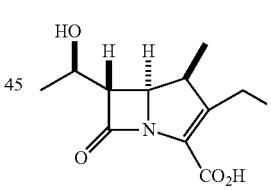
107
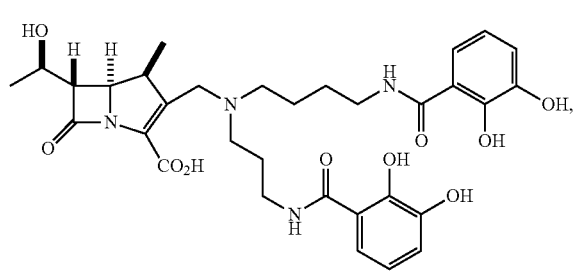
112
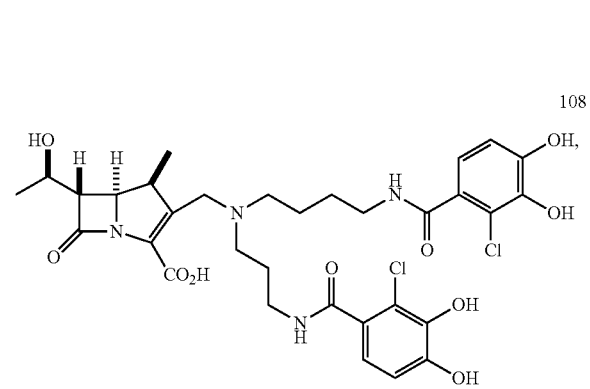
108
113

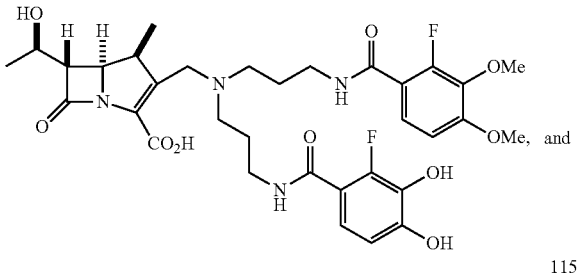

114

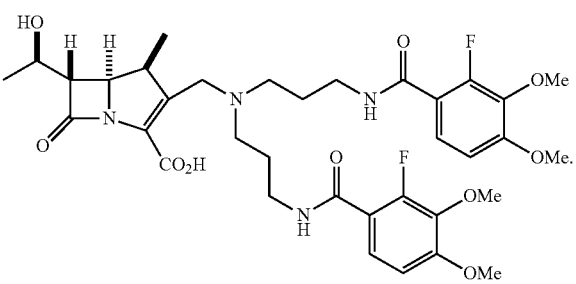

115

In one embodiment, the compound of Formula (IIb) is:

114

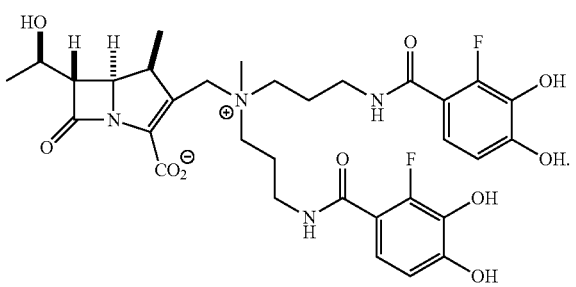

In certain embodiments, the compound has the structure of Formula (IIIa) or (IIIb):

Formula (IIIa)

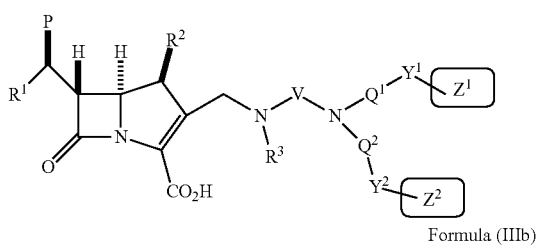

Formula (IIIb)

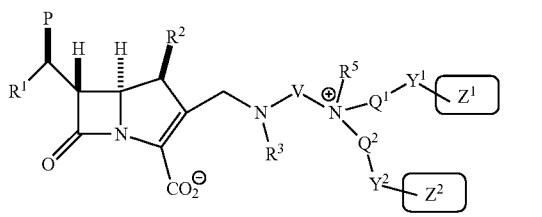

or a pharmaceutically acceptable salt or prodrug thereof, wherein:

$R^1$, $R^2$ and $R^3$ are each independently selected from H or alkyl;

P is H, OH, halogen, or hydroxyl protected by a hydroxyl protecting group;

V is a divalent —$(CR_2)_n$—(C=O)— or —$(CR_2)_n$— group, wherein n is 1, 2 or 3;

$Q^1$ and $Q^2$ are each independently selected from a divalent —$(CR_2)_p$—W—$(CR_2)_q$—, optionally substituted by one or more substituents selected from the group consisting of alkyl, haloalkyl, OR, CN, CONRR', SR, or NRR';

p and q are each independently 0, 1, or 2, and at least one of p or q is not 0;

W is absent, —CONR—, or —NRCO—;

$Y^1$ and $Y^2$ are each independently selected from a divalent —NR(C=O)—$(CR_2)_n$— or —(C=O)NR—$(CR_2)_n$— group, wherein n is 0, 1, or 2;

$Z^1$ and $Z^2$ are each independently selected from an aromatic or heteroaromatic ring, substituted by one or more substituents selected from the group consisting of alkyl, haloalkyl, OH, halogen, or hydroxyl protected by a hydroxyl protecting group; and $R^5$ in Formula (IIIb) is H or alkyl.

In certain embodiments of any of the Formulas herein, $R^1$ and $R^2$ are each H. In certain embodiments of any of the Formulas herein, $R^1$ and $R^2$ are not H. In certain embodiments of any of the Formulas herein, $R^1$ and $R^2$ are each alkyl, for example methyl, ethyl or propyl. In certain embodiments of any of the Formulas herein, $R^1$ and $R^2$ are each methyl.

In certain embodiments of any of the Formulas herein, $R^3$ is H. In certain embodiments of any of the Formulas herein, $R^3$ is not H. In certain embodiments of any of the Formulas herein, $R^3$ is alkyl, for example methyl, ethyl or propyl. In certain embodiments of any of the Formulas herein, $R^3$ is each methyl.

In certain embodiments of any of the Formulas herein, V is a divalent —$(CR_2)_n$— group, wherein n is 1, 2 or 3, for example methyl, ethyl or propyl. In certain embodiments of any of the Formulas herein, V is a divalent —$(CR_2)_n$—(C=O)— group, wherein n is 1, 2 or 3. In certain embodiments of any of the Formulas herein, when V is a divalent —$(CR_2)_n$—(C=O)— group, the —$(CR_2)_n$— is bonded to the N closest to the carbapenem moiety.

In certain embodiments, $R^5$ is H. In certain embodiments, $R^5$ is not H. In certain embodiments, $R^5$ is alkyl, for example methyl, ethyl or propyl. In certain embodiments, $R^5$ is each methyl.

In certain embodiments of any of the Formulas herein, —COOH is replaced with —COOM, wherein M is a cation.

In certain embodiments of any of the Formulas herein, $Y^1$ is —NR(C=O)—$(CR_2)_n$—, for example —NH(C=O)—$(CH_2)_n$—. In certain embodiments of any of the Formulas herein, $Y^1$ is —(C=O)NR—$(CR_2)_n$—, for example —(C=O)NH—$(CH_2)_n$—. In certain embodiments of any of the Formulas herein, $Y^1$ is a divalent —NH(C=O)—$(CH_2)_n$— or —(C=O)NH—$(CH_2)_n$— group. In certain embodiments, n is 0. In certain embodiments, n is 1. In certain embodiments, n is 2.

In certain embodiments of any of the Formulas herein, $Y^2$ is —NR(C=O)—$(CR_2)_n$—, for example —NH(C=O)—$(CH_2)_n$—. In certain embodiments of any of the Formulas herein, $Y^2$ is —(C=O)NR—$(CR_2)_n$—, for example —(C=O)NH—$(CH_2)_n$—. In certain embodiments of any of the Formulas herein, $Y^2$ is a divalent —NH(C=O)

—$(CH_2)_n$— or —$(C=O)NH$—$(CH_2)_n$— group. In certain embodiments, n is 0. In certain embodiments, n is 1. In certain embodiments, n is 2.

In certain embodiments of any of the Formulas herein, $Z^1$ is a substituted aromatic ring, for example a substituted phenyl. In certain embodiments of any of the Formulas herein, $Z^1$ is a substituted heteroaromatic ring, for example a substituted N-containing heterocycle or a substituted O-containing heterocycle, such as a substituted N-hydroxy-4-pyridonyl or substituted 4-pyranonyl. In certain embodiments, the phenyl is substituted with one or more substituents selected from the group consisting of hydroxy; halo, such as fluoro, chloro, bromo, iodo; alkoxy, such as methoxy or ethoxy; alkylcarbonyloxy, such as acetoxy or pivaloyloxy. In embodiments, the phenyl is substituted with one to three substituents selected from the group consisting of hydroxyl, fluoro, chloro, or methoxy.

In certain embodiments of any of the Formulas herein, $Z^2$ is a substituted aromatic ring, for example a substituted phenyl. In certain embodiments of any of the Formulas herein, $Z^2$ is a substituted heteroaromatic ring, for example a substituted N-containing heterocycle or a substituted O-containing heterocycle, such as a substituted N-hydroxy-4-pyridonyl or substituted 4-pyranonyl. In certain embodiments, the phenyl is substituted with one or more substituents selected from the group consisting of hydroxy; halo, such as fluoro, chloro, bromo, iodo; alkoxy, such as methoxy or ethoxy; alkylcarbonyloxy, such as acetoxy or pivaloyloxy. In embodiments, the phenyl is substituted with one to three substituents selected from the group consisting of hydroxyl, fluoro, chloro, or methoxy.

In certain embodiments of any of the Formulas herein, R is H. In certain embodiments of any of the Formulas herein, R is alkyl, for example methyl, ethyl, or propyl.

In certain embodiments, $Q^1$ is —$(CR_2)_p$—$(CR_2)_q$—, optionally substituted by one or more substituents selected from the group consisting of alkyl, haloalkyl, OR, CN, CONRR', SR, or NRR', p and q are each independently 0, 1, or 2. In certain embodiments, $Q^1$ is $CR_2$, $CR_2CR_2$, $CR_2CR_2CR_2$, or $CR_2CR_2CR_2CR_2$; wherein each R is independently selected from H or alkyl.

In certain embodiments, $Q^1$ is $CH_2$, $CH_2CH_2$, $CH_2CH_2CH_2$, or $CH_2CH_2CH_2CH_2$. In certain embodiments, $Q^1$ is a methyl, ethyl, propyl, or butyl group.

In certain embodiments, $Q^1$ is —$(CR_2)_p$—$CONR_2$—$(CR_2)_q$—, optionally substituted by one or more substituents selected from the group consisting of alkyl, haloalkyl, OR, CN, CONRR', SR, or NRR', p and q are each independently 0, 1, or 2. In certain embodiments, $Q^1$ is $CR_2$—$CONR_2$—$CR_2$, $CR_2$—$CONR_2$—$CR_2CR_2$, or $CR_2CR_2$—$CONR_2$—$CR_2CR_2$; wherein each R is independently selected from H or alkyl. In certain embodiments, $Q^1$ is $CH_2$—$CONH_2$—$CH_2$, $CH_2$—$CONH_2$—$CH_2CH_2$, or $CH_2CH_2$—$CONH_2$—$CH_2CH_2$.

In certain embodiments, $Q^2$ is —$(CR_2)_p$—$(CR_2)_q$—, optionally substituted by one or more substituents selected from the group consisting of alkyl, haloalkyl, OR, CN, CONRR', SR, or NRR', p and q are each independently 0, 1, or 2. In certain embodiments, $Q^2$ is $CR_2$, $CR_2CR_2$, $CR_2CR_2CR_2$, or $CR_2CR_2CR_2CR_2$; wherein each R is independently selected from H or alkyl.

In certain embodiments, $Q^2$ is $CH_2$, $CH_2CH_2$, $CH_2CH_2CH_2$, or $CH_2CH_2CH_2CH_2$. In certain embodiments, $Q^2$ is a methyl, ethyl, propyl, or butyl group.

In certain embodiments, $Q^2$ is —$(CR_2)_p$—$CONR_2$—$(CR_2)_q$—, optionally substituted by one or more substituents selected from the group consisting of alkyl, haloalkyl, OR, CN, CONRR', SR, or NRR', p and q are each independently 0, 1, or 2. In certain embodiments, $Q^2$ is $CR_2$—$CONR_2$—$CR_2$, $CR_2$—$CONR_2$—$CR_2CR_2$, or $CR_2CR_2$—$CONR_2$—$CR_2CR_2$; wherein each R is independently selected from H or alkyl. In certain embodiments, $Q^2$ is $CH_2$—$CONH_2$—$CH_2$, $CH_2$—$CONH_2$—$CH_2CH_2$, or $CH_2CH_2$—$CONH_2$—$CH_2CH_2$.

In certain embodiments, $Q^1$ and $Q^2$ can be the same or different and are each selected methyl, ethyl, propyl, or butyl. In certain embodiments, $Q^1$ and $Q^2$ are the same. In certain embodiments, both $Q^1$ and $Q^2$ are ethyl. In certain embodiments, both $Q^1$ and $Q^2$ are propyl.

In certain embodiments, $Q^1$ and $Q^2$ are different. In certain embodiments, $Q^1$ is ethyl and $Q^2$ is propyl. In certain embodiments, $Q^1$ is propyl and $Q^2$ is butyl.

In certain embodiments, $Q^1$ and $Q^2$ can be the same or different and are each selected methyl, ethyl, propyl, or butyl. In certain embodiments, $Q^1$ and $Q^2$ are the same. In certain embodiments, both $Q^1$ and $Q^2$ are ethyl. In certain embodiments, both $Q^1$ and $Q^2$ are propyl.

In certain embodiments, $Q^1$ and $Q^2$ are different. In certain embodiments, $Q^1$ is ethyl and $Q^2$ is propyl. In certain embodiments, $Q^1$ is propyl and $Q^2$ is butyl.

In certain embodiments of any of the Formulas herein, $Q^1$ and $Q^2$ are independently selected from $C_2$ to $C_4$ alkyl groups and W is absent. In certain embodiments, $Q^1$ and $Q^2$ are both ethyl groups and W is absent. In certain embodiments, $Q^1$ and $Q^2$ are both propyl groups and W is absent. In certain embodiments, $Q^1$ and $Q^2$ are both butyl groups and W is absent. In certain embodiments, $Q^1$ is an ethyl group, $Q^2$ is a propyl group and W is absent. In certain embodiments, $Q^1$ is an propyl group, $Q^2$ is a butyl group and W is absent. In certain embodiments, $Q^1$ is an ethyl group, $Q^2$ is a butyl group and W is absent.

In certain embodiments, $Y^1$ and $Y^2$ can be the same or different. In certain embodiments, both $Y^1$ and $Y^2$ are —N(H)-ethyl. In certain embodiments, both $Q^1$ and $Q^2$ are propyl. In certain embodiments, $Q^1$ and $Q^2$ are different. In certain embodiments, $Q^1$ is ethyl and $Q^2$ is propyl. In certain embodiments, $Q^1$ is propyl and $Q^2$ is butyl.

In certain embodiments of any of the Formulas herein, $Y^1$ and $Y^2$ are both —$NR(C=O)$—$(CR_2)_n$—, for example —$NH(C=O)$—$(CH_2)_n$—. In certain embodiments of any of the Formulas herein, $Y^1$ and $Y^2$ are both —$(C=O)NR$—$(CR_2)_n$—, for example —$(C=O)NH$—$(CH_2)_n$—. In certain embodiments of any of the Formulas herein, $Y^1$ and $Y^2$ are a divalent —$NH(C=O)$—$(CH_2)_n$— or —$(C=O)NH$—$(CH_2)_n$— group. In certain embodiments of any of the Formulas herein, $Y^1$ and $Y^2$ are a divalent —$NH(C=O)$— group. In certain embodiments of any of the Formulas herein, $Y^1$ and $Y^2$ are a divalent —$(C=O)NH$— group. In certain embodiments, n is 0. In certain embodiments, n is 1. In certain embodiments, n is 2.

In certain embodiments, $Z^1$ and $Z^2$ can be the same or different. In certain embodiments, $Z^1$ and $Z^2$ are the same. In certain embodiments, both $Z^1$ and $Z^2$ are substituted phenyl groups. In certain embodiments, $Z^1$ and $Z^2$ are different. In certain embodiments, the phenyl groups are substituted with the same substituents.

In certain embodiments, the compound is a compound of Formula IIIa. In certain embodiments, the compound is a compound of Formula IIIb.

In one embodiment, the compound of Formula (IIIa) is selected from the group consisting of:
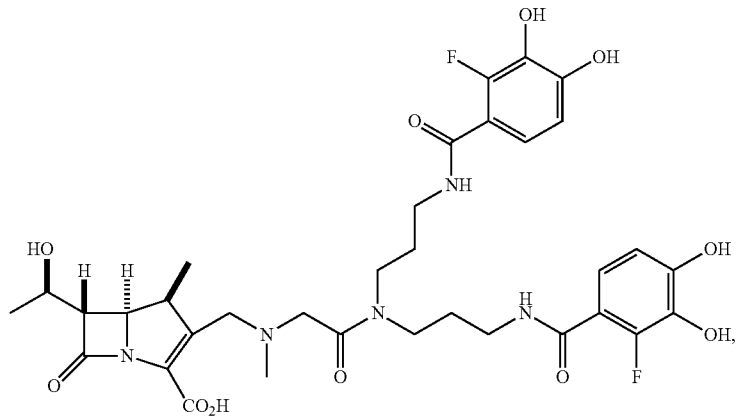
115
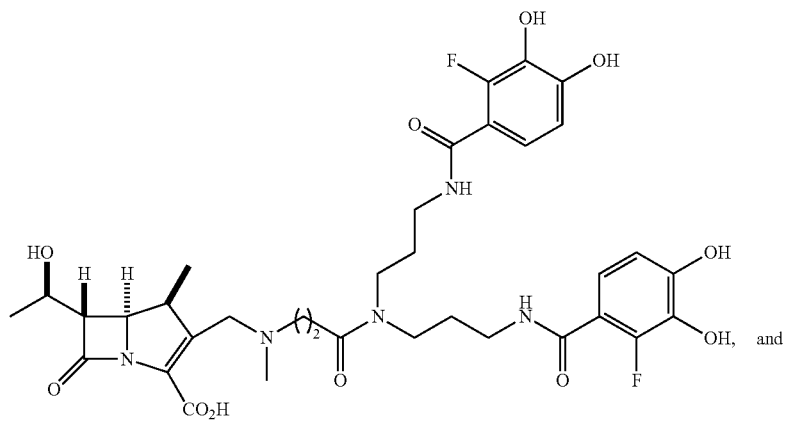
116
and
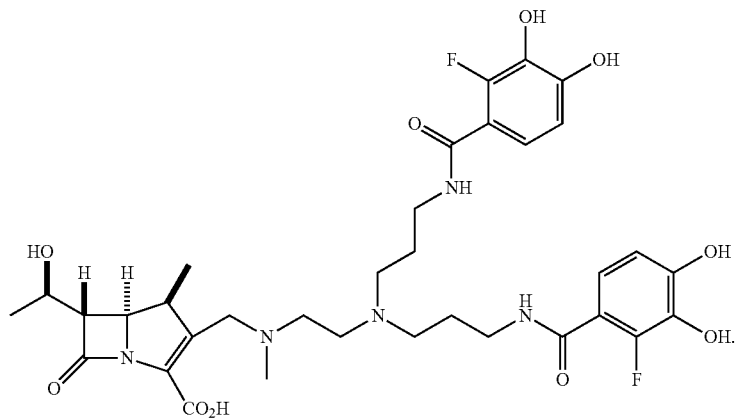
117

In one embodiment, the compound of Formula (IIIb) is:

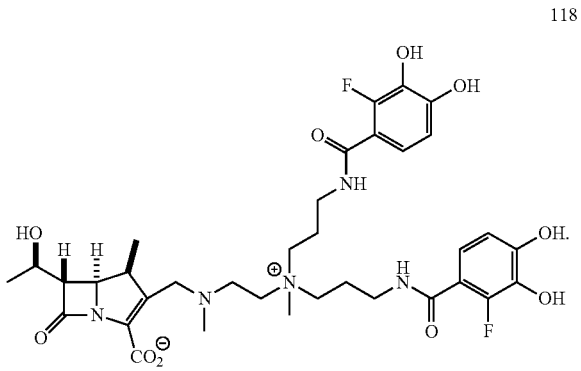

118

Method of Treatment

The present invention also provides a method of preventing or treating a bacterial infection, in a host, for example an animal, and typically a human, including administering a therapeutic amount of a compound of the present invention, or a pharmaceutically acceptable salt and/or prodrug therein, optionally in a pharmaceutically acceptable carrier or diluent, to patient in need thereof. In one embodiment, the bacterial infection is a drug resistant and/or multiple-drug resistant bacterial infection. The term "administrating" refers or "administration" refers to the act of providing a compound or pharmaceutical composition of the invention to a subject in need of treatment.

The invention also provides a compound of the present invention for use in medical therapy.

The present invention also provides a use of a therapeutic amount of a compound of the present invention, or a pharmaceutically acceptable salt and/or prodrug therein, optionally in a pharmaceutically acceptable carrier or diluent, for preventing or treating a Gram-negative bacterial infection, in a host, such as an animal, and typically a human.

The distinctive feature of Gram-negative bacteria is the presence of a double membrane surrounding each bacterial cell. Although all bacteria have an inner cell membrane, Gram-negative bacteria have a unique outer membrane. This outer membrane excludes certain drugs and antibiotics from penetrating the cell, partially accounting for why Gram-negative bacteria are generally more resistant to antibiotics than are Gram-positive bacteria. The pathogenic capability of Gram-negative bacteria is usually associated with certain components of their cell walls, particularly the lipopolysaccharide (endotoxin) layer. The outer membrane of Gram-negative bacteria is rich in lipopolysaccharide. If Gram-negative bacteria enter the bloodstream, lipopolysaccharide can trigger a cascade of events, including high fever and a drop in blood pressure. Unlike Gram-positive bacteria, which assume a violet color in Gram staining, Gram-negative bacteria incorporate the counterstain rather than the primary stain. Because the cell wall of Gram (−) bacteria is high in lipid content and low in peptidoglycan content, the primary crystal-violet escapes from the cell when the decolorizer is added. Most enteric (bowel related) illnesses can also be attributed to this group of bacteria.

Examples of Gram-negative bacteria include *Aeromonas* sp., *Acinetobacter* sp. such as *Acinetobacter baumannii* (or *A. calcoaceticus*), *Actinobacillus actinomycetemcomitans*, *Bacteroides* sp. such as *Bacteroides fragilis*, *Bartonella*, *Bdellovibrio* spp., *Bordetella pertussis*, *Brucella* sp., *Burkholderia cepacia*, *Burkholderia*, *pseudomallei*, *Campylobacter* sp., *Capnocytophaga* sp., *Cardiobacterium hominis*, *Chlamydia trachomatis*, *Citrobacter* sp., *Eikenella corrodens*, *Enterobacter* sp., *Escherichia coli*, *Francisella tularensis*, *Flavobacterium* sp., *Fusobacterium* sp., *Helicobacter pylori*, *Haemophilus influenzae*, *Haemophilus ducreyi*, *Klebsiella* spp. such as *Klebsiella pneumoniae*, *Kingella kingae*, *Legionella* spp. such as *Legionella pneumophila*, *Moraxella catarrhalis*, *Morganella*, *Neisseria gonorrhoeae*, *Neisseria meningitidis*, *Pasteurella pestis*, *Pasteurella multocida*, *Plesiomonas shigelloides*, *Prevotella* sp., *Proteus* spp., *Providencia*, *Pseudomonas* spp. such as *Pseudomonas aeruginosa*, *Salmonella* spp. such as *Salmonella enteriditis* and *Salmonella typhi*, *Serratia marcescens*, *Shigella* spp., *Vibrio cholerae*, *Vibrio parahaemolyticus*, *Vibrio vulnificus*, *Veillonella* sp., *Xanthomonas maltophilia* or *Stenotrophomonas maltophila*, *Yersinia pestis*, *Yersinia enterocolitica*. Additionally, some organisms simply tend not to be well differentiated by gram staining, despite any known phylogenetic affiliation with the Gram-negatives or Gram-positives. *Rickettsia prowazekii*, *Rickettsia rickettsii* and *Treponema pallidum*. Chlamydias are small, Gram-negative, peptidoglycan-less cocci that are obligate intracellular parasites of animals. Spirochetes are chemoheterotrophic bacteria whose cells are tightly coiled or resemble a stretched spring with Gram-negative-like cell envelopes. Spirochetes include *Spirillum minus*, *Borrelia burgdorferi* (Lyme disease), *Leptospira* spp. (leptospirosis) and *Treponema pallidum* (syphilis). Rickettsias and actinomycetes are also Gram-negative pleomorphic bacilli and coccobacilli that are obligate intracellular parasites of eucaryotes transmitted generally by insects and ticks.

*Acinetobacter* spp. are important pathogens associated with an increased frequency of infections over the past 2 decades. The majority (about 80%) of *Acinetobacter* infections are caused by *A. baumannii*. *A. baumannii* is capable of causing both community and health care-associated infections (HAIs), although HAIs are the most common form. The organism frequently causes infections associated with medical devices, e.g., vascular catheters, cerebrospinal fluid shunts or Foley catheters. Biofilm formation is a pathogenic mechanism in such infections.

Both desiccation tolerance and drug resistance may contribute to the persistance of *A. baumannii* in the hospital setting and may explain in part their propensity to cause prolonged outbreaks. *Acinetobacter* spp. (and *A. baumannii* in particular) have become resistant to many classes of antibiotics. Firstly, *Acinetobacter* spp. appear to be well suited for genetic exchange and are among a unique class of Gram-negative bacteria that are described as "naturally transformable". Lorenz M G et al. Microbiol. Rev. 58:563-602, 1994.

Moreover this resistance is multiple, causing serious therapeutic problems. Imipenem-resistant *A. baumannii* (IRAB) strains have been rising steadily during the past few years, and these isolates are often multidrug-resistant. This emergence of IRAB has become a worldwide problem and a troublesome development that threatens the continued successful treatment of *Acinetobacter* infections.

In one embodiment, the present invention provides a method of preventing or treating an *A. baumannii* infection in a host, for example an animal, and typically a human, including administering a therapeutic amount of a compound of the present invention, or a pharmaceutically acceptable salt and/or prodrug therein, optionally in a pharmaceutically acceptable carrier or diluent. In one embodiment, the infection is drug resistant *A. baumannii* infection, such as a multiple-drug resistant (MDR), extensively drug-resistant (XDR) or pandrug-resistant (PDR) *A. baumannii* infection. In a particular embodiment, the *A. baumannii* infection is resistant to cefotaxime, ceftriaxone, ceftazidime, ureidopenicillins, ciprofloxacin, gentamicin, imipenem or combinations thereof. In one embodiment, the method of the present invention further comprises a analyzing drug resistance via an antimicrobial susceptibility assay.

The *A. baumannii* infection may be any infection associated with *A. baumannii*. *A. braumanni* causes a variety of different diseases with different symptoms, many of which are often clinically indistinguishable from those of infections caused by other opportunistic bacteria, such as *Streptococcus pneumoniae*. Factors that increase the risk of *A. baumannii* infection include immunocompromised states, chronic lung disease, diabetes, lengthy hospital stays, illnesses that require the use of a hospital ventilator, having an open wound treated in a hospital, and treatments requiring invasive devices (e.g., urinary catheters).

In a particular embodiment, the *A. baumannii* infection is a primary blood stream infection (bacteremia). In certain embodiments, the bacteremia may be associated with symptom of sepsis, severe sepsis or septic shock. Bloodstream infections often initially cause symptoms like fever and chills, rash, and confusion or other altered mental states, and are often associated with an elevated lactic acid level associated with severe sepsis.

In another particular embodiment, the *A. baumannii* infection is pneumonia. The pneumonia may be hospital-acquired or community acquired. The hospital-acquired pneumonia may be ventilator-associated pneumonia (VAP). Pneumonia may cause of range of symptoms, including but not limited to, chills, fever, headache, breathing problems, muscle pain, chest pain and cough.

In another embodiment, the *A. baumannii* infection is meningitis. The meningitis may be hospital-acquired or community acquired. The hospital-acquired meningitis occurs following neurosurgery or head injury. Meningitis may cause a number of flu-like symptoms, including fever, headache, confusion, sensitivity to bright light, and nausea (with or without vomiting).

In a further embodiment, the *A. baumannii* infection is a wound or surgical site infection.

In embodiments, the method of the present invention results in a reduction in symptoms, course of infection or days of hospitalization. In a particular embodiment, the method of the present invention results in a reduction in symptoms of about 100%, about 20%, about 30%, about 40%, about 50%, about 60% or about 70% or more. In another particular embodiment, the method of the present invention results in a reduction in course of infection of about 10%, about 20%, about 30%, about 40%, about 50%, about 60% or about 70% or more. In yet another particular embodiment, the method of the present invention results in a reduction in course of infection of at least one, at least two, at least three, at least four, at least five, at least six or at least seven or more days. In yet another particular embodiment, the method of the present invention results in a reduction days of hospitalization of at least one, at least two, at least three, at least four, at least five, at least six or at least seven or more days. The present invention also provides a use of a therapeutic amount of a compound of the present invention, or a pharmaceutically acceptable salt and/or prodrug therein, optionally in a pharmaceutically acceptable carrier or diluent, in the manufacture of a medicament for preventing or treating a Gram-negative bacterial infection, in a host, such as an animal, and typically a human.

In one embodiment, provides a use of a therapeutic amount of a compound of the present invention, or a pharmaceutically acceptable salt and/or prodrug therein, optionally in a pharmaceutically acceptable carrier or diluent, in the manufacture of a medicament for preventing or treating a *A. baumannii* infection, in a host, such as an animal, and typically a human.

The invention also includes methods of inhibiting bacterial infection in a host. Inhibition of bacterial replication or treatment of an infection in a cell can be measured by showing a reduction in bacterial replication in a cell to a level lower than the level in an otherwise identical cell, which was not administered the compound of the invention. The reduction can be by about 80%, 85%, 90%, 95%, about 99.9% or more. The level of bacterial replication in a cell can be assessed by any known methods. For example, the level of bacterial replication in a cell can be assessed by evaluating the number of bacterial particles or amount of a bacterial component, such as a bacterial protein, a bacterial enzyme, or bacterial nucleic acid, in the cell or in fluid or debris associated with the cell. The number of infectious bacteria in a cell can be evaluated, for example, in a plaque assay. The level of a bacterial component such as a bacterial protein or enzyme in a cell can be evaluated using standard analytical techniques of protein biochemistry, such as, for example, using an activity assay for a bacterial enzyme, or using Western blotting or quantitative gel electrophoresis for a bacterial protein. Bacterial nucleic acid levels in a cell can be evaluated using standard analytical techniques such as Northern blotting and Southern Blotting or quantitation by polymerase chain reaction (PCR).

In a particular embodiment, the present invention provides a method of inhibiting *A. baumannii* replication.

Combination and Alternation Therapies

In one embodiment of the invention, one or more therapeutic agents, including particularly antimicrobial agents such as antibiotic agents that are effective against Gram-negative bacteria, can be used in combination and/or alternation with the compound/composition of the present invention to achieve an additive and/or synergistic therapeutic effect.

The active compounds can be administered in combination, alternation or sequential steps with another anti-bacterial agent. In combination therapy, effective dosages of two or more agents are administered together, whereas in alternation or sequential-step therapy, an effective dosage of each agent is administered serially or sequentially. The dosages given will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. In some embodiments, an antibacterial agent that exhibits an EC50 of 10-15 µM or less, or typically less than 1-5 µM.

In one particular embodiment, the combination includes a β-lactamase inhibitor, such as clavulanic acid, which has been used as in the delivery of prophylactic amounts of antibiotics in patients. Although Clavulanic acid does have some degree of bacterial activity, its principal role is as a beta-lactamase inhibitor. Clavulanic acid has a similar structure to the beta-lactam antibiotics but binds irreversibly to the beta-lactamase enzymes. Used in combination with the beta-lactam antibiotics, it has become one of the most prescribed antibiotics in the western world prolonging the effective life of antibiotics such as Ampicillin (as in GSK's Augmentin®).

It is possible that drug-resistant variants of bacteria can emerge after prolonged treatment with an anti-bacterial agent. The efficacy of a drug against the bacterial infection can be prolonged, augmented, or restored by administering the compound in combination or alternation with a second, and perhaps third, anti-bacterial agent, for example with a different site of activity than the principle drug. Alternatively, the pharmacokinetics, biodistribution or other parameter of the drug can be altered by such combination or alternation therapy.

Suitable antibiotic agents are disclosed, e.g. in Physician's Desk 30 Reference (PDR), Medical Economics Company (Montvale, N.J.), (53rd Ed.), 1999; Mayo Medical Center Formulary, Unabridged Version, Mayo Clinic (Rochester, Minn.), January 1998; Merck Index An Encyclopedia of Chemicals, Drugs and Biologicals, (11th Ed.), Merck & Co., Inc. (Rahway, N.J.), 1989; University of Wisconsin Antimicrobial Use Guide, http://www.medsch.wisc.edu/clinsci/5amcg/amcg.html; Introduction on the Use of the Antibiotics Guideline, of Specific Antibiotic Classes, Thomas Jefferson University, http://jeffiine.tju.edu/CWIS/OAC/antibiotics_guide/intro.html; and references cited therein.

Nonlimiting examples of agents that can be used in combination or alternation with the compounds of the invention include: aminoglycosides, β-lactam antibiotics, cephalosporius, macrolides, miscellaneous antibiotics, penicillins, tetracyclines, antifungals, antimalarial agents, antituberculosis agents, antibacterials, leprostatics, miscellaneous anti-infectives, quinolones, sulfonamides, urinary anti-infectives, nasal antibiotics, opthalmic antibiotics, opthalmic antibacterials, opthalmicquinalones, opthalmic sulfonamides, skin and mucous membrane antibiotics, skin and mucous membrane antifungals, skin and mucous membrane antibacterials, skin and mucous membrane miscellaneous anti-infectives, skin and mucous membranescabicides and pedulicides, skin and mucous membrane antineoplasts, nitrofurans and oxazolidinones.

Specific compounds include, for example, Amikacin (amikacin sulfate); Craramyein (gentamicin sulfate); Nebcin (tobramycin sulfate); Netromycin (netilmicin sulfate); Streptomycin Sulfate; and TOBI (tobramycin), Azactam (aztreonam); Cefotan (cefotetan); Lorabid (loracarbef); Mefoxin (cefoxitin); Merrem (meropenem); and Primaxin (imipenem and cilastatin for injectable suspension); Ancef (cefazolin); Ceclor (cefaclor); Cedax (ceflibuten); Cefizox (ceffizoxime sodium); Cefobid (cefoperazone sodium); Ceftin (cefuroxime axetil); Cefzil (cefprozil); Ceptaz (ceftazidime); Claforan (cefotaxime); Duricef (cefadroxil monohydrate); Fortaz (ceftazidime); Keflex (cephalexin); Keftab (cephalexin HCl); Kefurox (cefuroxime); Kefzol (cefazolin); Mandol (cefamandole nafate); Maxipime (cefepime HCl); Monocid (cefonicidsodium); Omnicef (cefdinir); Rocephin (ceftriaxone); Suprax (cefixime); Tazicef (ceftazidime); Tazidime (ceftazidime); Vantin (cefpodoxime proxetil); and Zinacef5(cefuroxime); Biaxin (clarithromycin); Dynabac (dirithromycin); E.E.S. 200 (Erythromycin Ethylsuccinate); E.E.S. 400 (Erythromycin Ethylsuccinate); EryPed 200 (Erythromycin Ethylsuccinate); EryPed 400 (Erythromycin Ethylsuccinate); EryTab (Erythromycin delayed-release tablets); Erythrocin Stearate (Erythromycin stearate); Ilosone (erythromycinestolate); PCE Dispertab (erythromycin particles in tablets); Pediazole (erythromycin ethylsuccinate and sulfisoxazole acetyl for oral suspension); Tao (troleandomycin); Zithromax (azithromycin); and Erythromycin; Cleocin HCl (clindamycin hydrochloride); Cleotin Phosphate (elindamycin phosphate); Coly-Mycin M (colistimethate sodium); and Vancocin HCl (vancomycin hydrochloride); Amoxil (amoxicillin); Augmentin (amoxicillin/clavulanate potassium); Bicillin C-R 900/300 (Penicillin G benzathine and Penicillin G procaine suspension); Bicillin C-R (Penicillin G benzathine and Penicillin G procaine suspension); Bicillin L-A (Penicillin G benzathine suspension); Geoeillin (carbencillin indanyl sodium); Mezlin (sterile mezlocillinsodium); Omnipen (ampicillin); Pen-Vee K (penicillin V potassium); Pfizerpen (penicillin G potassium); Pipracil (piperacillin sodium); Speetrobid (bacampicillin-HCl); Ticar (tiearcillin disodium); Timentin (ticarcillin disodium and clavulanate potassium); Unasyn (ampicillin sodium/sulbactam sodium); Zosyn (piperacillin sodium and tazobactam sodium); and Dicloxacillin Sodium; Achromycin V (tetracycline HCl); Declomycin (demeclocycline HCl); Dynacin (minocylcine HCl); Minocin (minocycline hydrochloride); Monodox (Doxycycline monohydrate capsules); Terramycin (oxytetracyline); Vectrin (minocycline hydrochloride); Vibramycin Calcium (doxycycline sodium); Vibramycin Hyclate (doxycycline hyclate); Vibramycin Monohydrate (doxycycline monohydrate); Vibra-Tabs (doxycyclinehydrate); Declomycin (demeclocycline HCl); Vibramycin (doxycycline); Dynacin (Minocyline HCl); Terramycin (oxytetracyline HCl); Achromycin V capsules5 (tetracycline HCl); Linco-mycins; and Cleotin HCl (clindamycin HCl); Abelcet (amphotericin B lipid complex); AmBisome (amphotericin B); Amphotec (amphotericin B cholesterol sulfatecomplex); Ancobon (flucytosine); Diflucan (fluconazole); Fulvicin P/Gamma (ultramicrosize griseofulvin); Fulvicin P/G 165 and 330 (ultramicrosize griseofulvin); Grifulvin V (griseofulvin); Gals-PEG (gxiseofulvin ultramicrosize); Lamisil (terbinafine hydrochloride); Nizoral (ketoconazole); Amphotericin B; Lotrimin (clotrimazole); Dapsone tablets (dapsone); Diflucan (fluconazole); Monistat-Derm cream (miconazole); Mycostalin Crc .am (nystatin); and Sporanox (itraconazole); Aralen hydrochloride (chloroquine HCl); Aralen phosphate (chloroquine phosphate); Dataprim (pyrimethamine); Ladam (mefloquine HCl); and Plaquenil (hydroxychloroqnine sulfate); Capastat sulfate (capreomycinsulfate); Myambutol (ethambutol hydrochloride); Mycobutin (rifabutin capsules); Nydrazid (isoniazid injection); Paser (aminosalicylic acid); Priflin (rifapentine); Pyrazinamide tablets (pyrazinamide); Rifadin (rifampin capsules); Rifadin IV (rifampin for injection); Rifamate (rifampin and isoniazid); Rifater (rifampin, isoniazid and pyrazinamide); Seromycin (cycloserine capsules); Streptomycin-Sulfate; Tice BCG (BCG vaccine); Cycloserine (seromycin capsules); Urised (Methenamine); and Trecator-SC (ethionamide tablets); Alferon N (interferon alfa-n3); Crixivan (indinavir sulfate); Cytovene (ganciclovir); Cytovene-IV (ganciclovir sodium); Epivir (lamivudine); Famvir (famciclovir); Flumadine (rimantadine HCl); Foscavir (foscamet sodium); Hivid (zalcitabine); Intron A (interferon alfa-2b); Invirase (saquinavir mesylate); Norvir (ritonavir); Rebetron combination therapy, which contains Rebetrol (ribavirin) and Intron A (inteferon alfa-2b); Rescriptor (delavirdine mesylate); Retrovir (ziduvudine); Retrovir IV (ziduvudine); Symmetrel (amantadine HCl); Synagis (palivizumab); Valtrex (valacyclovir HCl); Videx (didanosine); Viracept (nelfinavir mesylate); Viramune (nevirapine); Virazole (ribavirin); Vistide (cidofovir); Zerit (stavudine (d4T)); Symmetrel Syrup (amantadine HCl); Combivir Tablets (lamiduvine); and Zovirax (acyclovir); Dapsone Tablets (dapsone); Daraprim (pyrimethamine); Flagyl 375 (metronidazole); Flagyl ER Tablets (metronidazole); Flagyl I.V. (metronidazole); Furoxone (furazolidone); Mepron (atovaquone); and Neutrexin (tfimetrexate glucuronate); Cipro (ciprofloxacin HCl); Floxin (ofloxacin); Levaquin (levofloxacin); Mazaquin (lomefioxacin HCl); Noroxin (norfloxacin); Penetrex (enoxacin); Raxar (grepafloxacin HCl); Trovan (trovafioxacin mesylate); and Zagam (sparfloxacin); Bactrim. (trimethoprim and sulfamethoxazole); Bactrim DS (Irimethoprim and sulfamethoxazole double strength); Pediazole (erythromycin ethylsuccinate and sulfisoxazole acetyl); Septra (trimethoprim and sulfamethoxazole); Septra DS (trimethoprim and sulfamethoxazole); Co-Trimoxazole, Sulfadiazine, Battrim I.V. Infusion (sulfamethoxazole); Sulfapyridine and Pediazole (erythromycin ethylsuccinate and sulfisoxazole acetyl); Furadantin (nitrofurantoin); Macrobid (nitrofurantoin monohydrate macrocrystals); Macrodantin (nitrofurantoin macrocrystals); Monurol Sachet (fosfomycin tromethamine); NegGram Caplets (nalidixic acid); Septra (trimethoprim and sulfamethoxazole); Septra DS (trimethoprim and sulfamethoxazole); Urised (a combination of the antisepticsmethenamine, methylene blue, phenyl salicylate, benzoic acid and parasympatholytics (atropine sulfate) hyoscyamine); (oxytetracycline HCl, sulfamethizole and phenazopyridine HCl); (methenamine mandelate); Bactroban (mupirocin); Chloromycetin opthalmic (chloramphenical); Cortisporin (neomycin and polymyxin B sulfates and hydrocortisone acetate cream); Ilotycin (erythromycin opthalmic ointment); NeoDecadron (neomycin sulfate-dexamethasone sodium phosphate); Polytrim (tfimethoprim and polythyxin B sulfate opthalmic solution); Terra-Cortril (oxytetracycline HCl and hydrocortisone acetate); Terramycin (oxytetracycline); and TobraDex (tobramycin and dexamethasone opthalmic suspension and ointment); Vita-A opthalmic ointment, (vidatabine); (norfloxacinopthalmic solution; Ciloxan opthalmic solution and ointment (Ciprofloxacin HCl); and Ocuflox opthalmic solution (ofioxacin), Blephamide opthalmicointment (sulfacetamide sodium and prednisolone acetate); and Blephamideopthalmic suspension (sulfacetamide sodium and predrdsolone acetate); A/T/S (erythromycin); Bactroban (mupirocin); Benzamycin (erythromycin-benzoyl peroxide topical gel); Betadine (povidone-odine); Cleotin T (clindamy cinphosphate topical solution); Clindets (clindamycin phosphate pledgets); Cortispofin (neomycin, polymyxin B sulfates and hydrocortisone acetate cream); Emgel (erythromycin); Erycette (erythromycin topical solution); Garamycin (gentamicin sulfate); Klaron (sodium sulfacetamide lotion); Mycostatin (nystatin cream); Theramycin Z (erythromycin topical solution); T-Stat (erythromycin); Chloromycetin (chloramphenicol opthalmic ointment); Cortisporin (neomycin and polymyxin B sulfates, bacitracin zinc and hydrocortisone opthalmic ointment); Ilotycin (erythromycin); NeoDeeadron (neomycin sulfate-dexamethasone sodium phosphate); Polytrim (trimethoprim and polymyxin B sulfate); Terra-Cortril (oxytetracycline HCl and hydrocortisone acetate); Terramycin (oxytetracycline); Exelderm (sulconazole nitrate); Fungizone (amphotericin B oral suspension); Lamisil (terbinafine hydrochloride cream); Loprox (ciclopiroxolamine); Lotrimin (clotrimazole); Lotrisone (clotrimazole and betamethasone diproprionate); Mentax (butenafine HCl); Monistat-Denn (miconazole nitrate); Mycelex (clotrimazole); Mycostatin (nystatin); Naffin (nattifine HCl); Nizoral Ocetoconazole); Nystop (nystatin); Oxistat (oxiconazole nitrate); Selsun Rx (2.5% selenium sulfide lotion); and Spectazole (econazole nitrate); Denavir (penciclovir cream); and Zovirax (acyclovir); Benzashave Coenzoyl peroxide); Betadine (povidone-iodine); Betasept (chlorhexidine gluconate); Cetaphil (soap substitute); Clorpactin WCS-90 (sodium oxychlorosene); Dapsone Tablets (dapsone); Desquam-E Coenzoyl peroxide); Desquam-X (benzoyl peroxide); Hibiclens (chlorhexidine gluconate); Hibistat (ehlorhexidine gluconate); Impregon (tetrachlorosalicylanilide 2%); MetroCream (metronidazole); MetroGel (metronidazole); Noritate (metronidazole); pHisoHex (hexachlorophene detergent cleanser); Sulfacet-R (sodium sulfacetamide 10% and sulfur 5%); Sulfamylon (materfide acetate); Tfiaz Coenzoyl peroxide); and Vanoxide-HC Coenzoyl peroxide hydrocortisone); Acticin (permethrin); Elimite (permethrin); Eurax (crotamiton); Efudex (fluoro-uracil); Fluoroplex.

In a particular embodiment of the invention, one or more therapeutic agents, including particularly antimicrobial agents such as antibiotic agents that are effective against *A. baumanmii* can be used in combination and/or alternation with the compound/composition of the present invention to achieve an additive and/or synergistic therapeutic effect.

In one embodiment, the one or more therapeutic agents are selected from the group consisting of ampicillin-sulbactam, meropenem, imipenem, rifampin polymyxin B, cefepim, colistin, tobramycin and combinations thereof.

In a particular embodiment, colistin can be used in combination and/or alternation with the compound/composition of the present invention to achieve an additive and/or synergistic therapeutic effect.

In a particular embodiment, colistin and one or more therapeutic agents effective against *A. baumannii* can be used in combination and/or alternation with the compound/composition of the present invention to achieve an additive and/or synergistic therapeutic effect. In one embodiment, the one or more additional therapeutic agents is selected from rifampin, meropenem and azithromycin.

Pharmaceutical Compositions

Hosts, including humans can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

An optional dose of the compound for treatment of a bacterial (such as a Gram-negative bacteria, and more particularly, *A. baumannii*) infection is about 1 to 50 mg/kg, or 1 to 20 mg/kg, of body weight per day, more generally 0.1 to about 100 mg per kilogram body weight of the recipient per day. The effective dosage range of the pharmaceutically acceptable salts and prodrugs can be calculated based on the weight of the parent nucleoside to be delivered. If the salt or prodrug exhibits activity in itself, the effective dosage can be estimated as above using the weight of the salt or prodrug, or by other means known to those skilled in the art.

Optionally, the active ingredient should be administered to achieve peak plasma concentrations of the active compound of from about 0.2 to 70 M, e.g., about 1.0 to 10 uM. This may be achieved, for example, by the intravenous injection of a 0.1 to 5% solution of the active ingredient, optionally in saline, or administered as a bolus of the active ingredient. The concentration of active compound in the drug composition will depend on absorption, inactivation and excretion rates of the drug as well as other factors known to those of skill in the art. It is to be further understood that for any particular subject, specific dosage regimens should be adjusted according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

The compound is conveniently administered in unit any suitable dosage form, including but not limited to one containing 7 to 3000 mg, or 70 to 1400 mg of active ingredient per unit dosage form. A dosage of 50-1000 mg is optional.

The active compound can be administered in a pharmaceutically acceptable carrier available in the art, and can be administered by a chosen route of administration. Pharmaceutical compositions can be prepared, packaged, or sold in a variety of formulations which can be suitable for one or more routes of administration such as, for example, oral, intravenous, intramuscular, topical, subcutaneous, rectal, vaginal, parenteral, pulmonary, intranasal, buccal, ophthalmic, or another route of administration. The active materials can be administered in liquid or solid form. Other contemplated formulations include projected nanoparticles, liposomal preparations, resealed erythrocytes containing the active ingredient, and immunologically-based formulations.

The active compound may be administered intravenously or intraperitoneally by infusion or injection. Solutions of the active compound or its salts may be prepared in water or saline, optionally mixed with a non-toxic surfactant. Dispersions may be prepared in glycerol, liquid polyethylene glycols, triacetin, and mixtures thereof, and in oils. Under ordinary conditions of storage and use, these preparations contain a preservative to prevent growth of microorganisms.

Pharmaceutical dosage forms suitable for injection or infusion may include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form is optionally sterile, fluid, and stable under conditions of manufacture and storage. The liquid carrier or vehicle may be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof.

For oral therapeutic administration, the active compound can be combined with one or more excipients and used in the form of ingestible tablets, buccal tablets, troches, capsules, elixirs, suspensions, syrups, wafers, and the like. Such compositions and preparations can contain at least 0.1% (w/w) of active compound. The percentage of the compositions and preparations can, of course, be varied, for example from about 0.1% to nearly 100% of the weight of a given unit dosage form. The amount of active compound in such therapeutically useful compositions is such that an effective dosage level will be obtained upon administration.

The tablets, troches, pills, capsules, and the like may also contain one or more of the following: binders, such as microcrystalline cellulose, gum tragacanth, acacia, corn starch, or gelatin; excipients, such as dicalcium phosphate, starch or lactose; a disintegrating agent, such as corn starch, potato starch, alginic acid, primogel, and the like; a lubricant, such as magnesium stearate or Sterotes; a glidant, such as colloidal silicon dioxide; a sweetening agent, such as sucrose, fructose, lactose, saccharin, or aspartame; a flavoring agent such as peppermint, methylsalicylate, oil of wintergreen, or cherry flavoring; and a peptide antibacterial agent, such as envuvirtide (Fuzeon™). When the unit dosage form is a capsule, it can contain, in addition to materials of the above type, a liquid carrier, such as a vegetable oil or a polyethylene glycol. Various other materials may be present as coatings or to otherwise modify the physical form of the solid unit dosage form.

In one embodiment, the active compounds are prepared with carriers that will protect the compound against rapid elimination from the body, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, and polylacetic acid. Methods for preparation of such formulations will be apparent to those skilled in the art. The materials may also be obtained commercially from Alza Corporation.

Other formulations can also be developed. For example, the compounds can be administered in liposomal suspensions (including liposomes targeted to infected cells with monoclonal antibodies to bacterial antigens). These may be prepared according to methods known to those skilled in the art, for example, as described in U.S. Pat. No. 4,522,811. For example, liposome formulations may be prepared in a variety of lipid(s) (such as stearoyl phosphatidyl ethanolamine, stearoyl phosphatidyl choline, arachadoyl phosphatidyl choline, and cholesterol).

A pharmaceutical composition of the invention may be prepared, packaged, or sold in a formulation suitable for rectal administration. Such a composition may be in the form of, for example, a suppository, a retention enema preparation, and a solution for rectal or colonic irrigation. A pharmaceutical composition of the invention may also be prepared, packaged, or sold in a formulation suitable for vaginal administration. Such a composition may be in the form of, for example, a suppository, an impregnated or coated vaginally insertable material such as a tampon, a douche preparation, or a solution for vaginal irrigation. A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration, which can include particles wherein at least 98% of the particles by weight have a diameter greater than 0.5 nanometers and at least 95% of the particles by number have a diameter less than 7 nanometers. Typically least 95% of the particles by weight have a diameter greater than 1 nanometer and at least 90% of the particles by number have a diameter less than 6 nanometers. The active ingredient can also be in the form of droplets of a solution or suspension, for example those that have an average diameter in the range from about 0.1 to about 200 nanometers.

The formulations described herein as being useful for pulmonary delivery are also useful for intranasal delivery of a pharmaceutical composition of the invention. Another formulation suitable for intranasal administration is a coarse powder comprising the active ingredient and having an average particle from about 0.2 to 500 micrometers.

A pharmaceutical composition of the invention may be prepared, packaged, or sold in a formulation suitable for ophthalmic administration. For topical administration, the present compounds can be applied in pure form, i.e., as a liquid. However, typically, the compounds are administered to the skin as compositions or formulations, in combination with a dermatologically acceptable carrier. Useful solid carriers include finely divided solids such as talc, clay, microcrystalline cellulose, silica, alumina, and the like. Useful liquid carriers include water, alcohols, glycols, and blends of two or more of these, in which the present compounds can be dissolved or dispersed at effective levels, optionally with the aid of non-toxic surfactants. Adjuvants such as fragrances and additional antimicrobial agents can be added to optimize properties for a given use. The resulting liquid compositions can be applied using absorbent pads, used to impregnate bandages or other dressings, or sprayed onto the affected area using pump-type or aerosol sprayers.

The compounds/compositions of the present invention are optionally administered in a controlled release formulation, which can be a degradable or nondegradable polymer, hydrogel or ganogel or other physical construct that modifies the bioabsorption, half-life or biodegradation of the active agent(s). The controlled release formulation can be a material that is painted or otherwise applied onto the afflicted site, either internally or externally. In one embodiment, the invention provides a biodegradable bolus or implant. The controlled release formulation with appropriated selected imaging agent can be used to coat a transplanted organ or tissue to prevent rejection. It can alternatively be implanted or otherwise applied near the site of potential infection. Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user. The compound or a pharmaceutically acceptable prodrug or salts thereof can also be mixed with other active materials that do not impair the desired action, or with materials that supplement the desired action, such as antibiotics, antifungals, anti-inflammatories, or other antibacterials, including other nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic. If administered intravenously, useful carriers are physiological saline or phosphate buffered saline (PS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation.

The concentration of the compound(s) in a liquid composition, such as a lotion, will, for example, range from about 0.1% to about 95% by weight, or from about 0.5% to about 25% by weight. The concentration in a semi-solid or solid composition such as a gel or a powder will, for example, range from about 0.1% to 100% by weight, or about 0.5% to about 5% by weight. Single doses for intravenous injection, subcutaneous, intramuscular or topical administration, infusion, ingestion or suppository will generally be from about 0.001 to about 5000 mg, and be administered from about 1 to about 3 times daily, to yield levels of about 0.01 to about 500 mg/kg, for adults.

The invention also includes one or more compounds disclosed herein, or any combination thereof, or salt thereof, in an amount effective to inhibit bacterial (such as a Gram-negative bacteria, and particularly A. baumannii) replication in a host. The compound can be useful for inhibiting bacterial replication in a cell or neutralization (i.e. inactivation) of extracellular bacteria.

As used herein, to inhibit bacterial replication in a host means to reduce the bacterial load in a host to a level, which is lower than the level of the bacterial load in an otherwise identical host, which was not administered the compound. Bacterial load in a mammal can be reduced by about 1 to 12 log 10 or more relative to an otherwise identical mammal, which was not administered the compound. Bacterial load in a mammal can be assessed by a number of methods known in the art such as, for example, obtaining a tissue or fluid sample from the mammal and assessing the amount of bacterial components in the mammal contained therein using technology which is either immunological, biochemical or molecular biological in nature and which is well known to the skilled artisan and which are described elsewhere herein. Inhibition of bacterial replication in a cell is assessed using similar or identical assays as those used to assess bacterial load in a mammal. The invention also includes a kit for administering a compound of the invention, a pharmaceutically acceptable salt thereof, or a pharmaceutical composition, to a host for treatment of a bacterial (such as Gram-negative bacteria) infection. Typically, the host is a human. The kit comprises one or more compounds of the invention, or a combination thereof, and optionally an instructional material, which describes adventitially administering the composition to the mammal by any of the routes of administration described herein. In another embodiment, this kit comprises a (typically sterile) solvent suitable for dissolving or suspending the composition of the invention prior to administering the compound to the mammal.

EXAMPLES

Nuclear magnetic resonance (NMR) spectra were obtained on a Varian INOVA 400 (400 MHz) spectrometer; chemical shifts (δ) are reported in parts per million (ppm), and the signals are described as s (singlet), d (doublet), t (triplet), q (quartet), br (broad signal), dd (doublet of doublet), dt (triplet of doublet), and m (multiplet). All reactions were monitored using thin layer chromatography (TLC; 200 mm silica gel GF plates) on Analtech or HPLC.

Dry dichloromethane, acetonitrile, DMF, and THF were obtained by drying over 4 Å molecular sieves.

The following abbreviations may have been used:
AcOH: acetic acid
Bn: benzyl
Boc: tert-butyloxycarbonyl
DIEA: diisopropylethylamine
DI water: deionized water
DMF: N,N-dimethylformamide
DMSO: dimethylsulfoxide
dppb: 1,4-bis(diphenylphosphino)butane
EDC: N-(3-dimethylaminopropyl)-N'-ethylcarbodiimide EtOAc: ethyl acetate
Hex: hexanes
HOBt: 1-hydroxybenzotriazole
IPA: isopropanol
LDA: lithium diidopropylamine
Piv: pivaloyl
Pd$_2$(dba)$_3$: tris(dibenzylideneacetone)dipalladium (0)
Pd(OH)$_2$/C: palladium (II) hydroxide on carbon
PNB: para-nitrobenzyl
SPB: sodium phosphate buffer
TBAF: tetra-n-butylammonium fluoride
TBS or TBDMS: tert-butyldimethylsilyl
TEA: triethylamine
TES: triethylsilyl
TFA: trifluoroacetic acid
THF: tetrahydrofuran Preparation of the Carbapenem Intermediate (CPI)

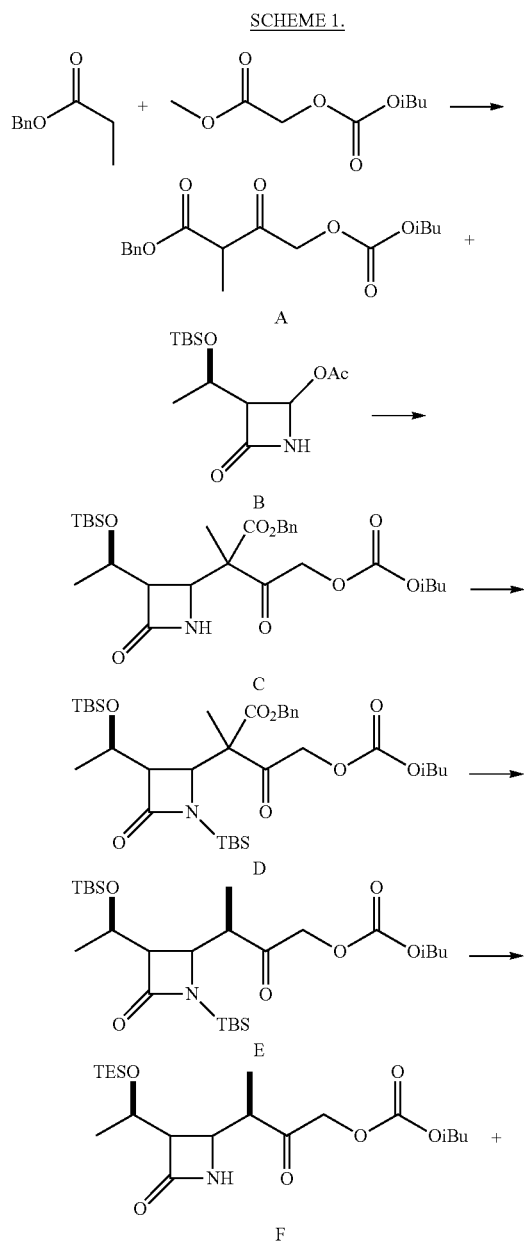

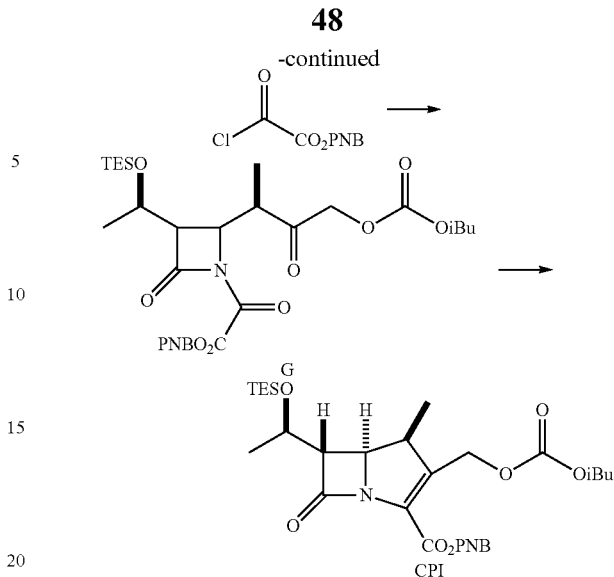

Carbapenem Intermediate (CPI) was prepared according to the synthetic scheme shown in Scheme 1. In the first step of the process, benzyl propionate was reacted with isobutoxycarbonyloxy acetic acid methyl ester in a solvent at low temperature in the presence of LDA to form ketoester A. The ketoester A was then contacted with the acetoxyazetidinone B (prepared by any number of known, synthetic routes) in a solvent, and sodium carbonate was added. The reaction aged for a period of time at a temperature such that the reaction went substantially to completion, generating the target lactam C.

The lactam C was dissolved in a solvent, such as DMF, to which a suitable base (such as DIEA) and TBSOTf were added, and the mixture allowed to age for a period of time at a temperature. Following workup, the bis-TBS-ketoester D was isolated.

The crude ketoester D was dissolved in ethyl acetate in an appropriate reaction vessel. Formic acid and a catalyst, such as Pd/C, were added to the reaction vessel, and the entire mixture was hydrogenated at an appropriate hydrogen pressure (40-50 psi) for a period of time such that the decarboxylation reaction proceeded to completion. The reaction mixture was filtered over a pad of Celite®, and the solvent was removed under vacuum. Product E was isolated following purification by column chromatography.

The bis-TBS ketolactam E was then de-silylated using 2N HCl in acetonitrile and the product was isolated after a standard aqueous workup. The crude product was dissolved in a solvent, such as CH$_2$Cl$_2$, and allowed to react with triethylsilyl chloride and imidazole for several hours (monitored by TLC) at r.t. Following aqueous workup, O-TES ketolactam F was isolated and purified on silica gel.

N-PNB, O-TES ketolactam G was produced by reacting ketolactam F with p-nitrobenzyl oxalylchloride in a suitable solvent (CH$_2$Cl$_2$, for example) in the presence of a base (DIEA, for example). The mixture was allowed to age for a period of time (and at an appropriate temperature) to effect a substantially complete reaction as monitored by an appropriate means (e.g., TLC or HPLC). Following workup in a usual manner, intermediate G was isolated.

To a solution of compound G in a suitable solvent was added triethylphosphite, and the mixture heated to reflux until complete by TLC. Following workup and purification in the appropriate manner, CPI was isolated.

Preparation of Gram-Negative Active Carbapenems
Example 1: Synthesis of 1
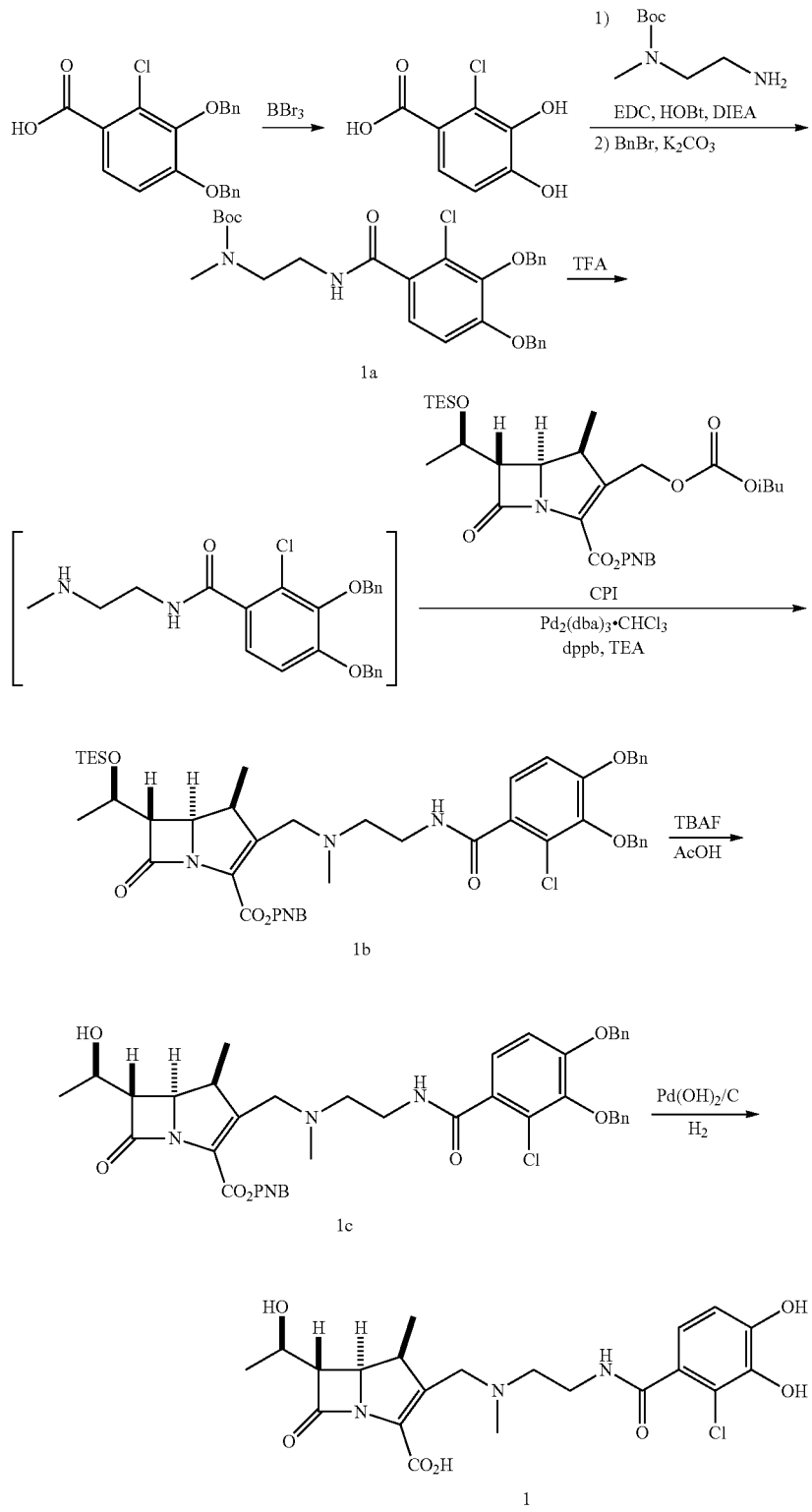
SCHEME 2.

Step 1

Into a mixture of 2-chloro-3,4-dimethoxybenzoic acid (9.8 g, 45 mmol) in $CH_2Cl_2$ (40 mL) was added $BBr_3$ solution (1.0M in $CH_2Cl_2$) (180 mL, 180 mmol) over 10 min at 0° C. under $N_2$. After stirring for 3 h at 0° C. at r.t., the reaction solution was poured into 2M HCl (600 mL) with ice and then extracted with EtOAc (1.2 L). After the phase separation, the organic layer was washed with $H_2O$ (3×150 mL), dried over $MgSO_4$, and concentrated in vacuo. The crude 2-chloro-3,4-dihydroxybenzoic acid (7.68 g, 91%) was spectroscopically pure and directly used for the next reaction.

$^1$H NMR (DMSO-d6, 400 MHz): δ 12.65 (br s, 1H), 10.36 (s, 1H), 9.27 (s, 1H), 7.23 (d, J=8.4 Hz, 1H), 6.77 (d, J=8.4 Hz, 1H).

Step 2

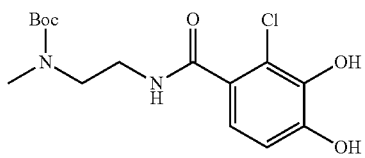 [SMILES: CN(CCNC(=O)c1ccc(O)c(O)c1Cl)C(=O)OC(C)(C)C]

Into a solution of N-Boc-N-methylethylene diamine (536 μL, 3.0 mmol) in $CH_2Cl_2$ (15 mL) were added HOBt.x$H_2O$ (668 mg, 4.2 mmol), DIEA (1.05 mL, 6.0 mmol), 2-chloro-3,4-dihydroxybenzoic acid (679 mg, 3.6 mmol) and EDC-HCl (805 mg, 4.2 mmol), respectively, at r.t. After stirring overnight, the reaction mixture was diluted with EtOAc (150 mL) and washed with half sat. $NH_4Cl$ (40 mL) and brine. The organic phase was dried over $MgSO_4$ and concentrated in vacuo. The crude catechol (860 mg) was directly used for the next reaction.

Step 3

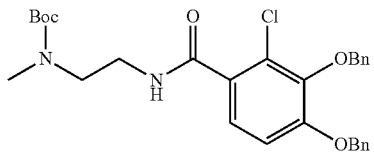 [SMILES: CNCCNC(=O)c1ccc(OCc2ccccc2)c(OCc2ccccc2)c1Cl]

1a

Into a solution of the crude catecol (860 mg, 2.5 mmol) in DMF (5 mL) were added $K_2CO_3$ (1.38 g, 10 mmol) and BnBr (714 μL, 6.0 mmol) at r.t. After stirring overnight, the reaction mixture was diluted with EtOAc (150 mL) and washed with $H_2O$ (3×25 mL) and brine. The organic layer was dried over $MgSO_4$ and concentrated in vacuo. The crude was purified on a silica gel column (Hex/EtOAc=5/5 to 3/7) to afford 1a (1.05 g, 66% in 2 steps) as slightly tannish paste.

$^1$H NMR (CDCl$_3$, 400 MHz): δ 7.47-7.30 (m, 11H), 6.91 (br, 1H), 5.15 (s, 2H), 5.02 (s, 2H), 3.60 (q, J=5.6 Hz, 2H), 3.49 (br, 2H), 2.92 (s, 3H), 1.42 (s, 9H).

Step 4

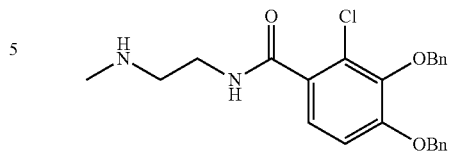

Into a solution of 1a (1.50 g, 2.86 mmol) in $CH_2Cl_2$ (15 mL) was added TFA (4.35 mL, 57.2 mmol) at r.t. After stirred for 24 hrs at r.t., the solution was concentrated. The residue was treated with sat. $NaHCO_3$ (40 mL), and then diluted with EtOAc (150 mL) and $H_2O$ (80 mL). After phase extraction, the aqueous phase was further extracted with ethyl acetate (50 mL). The combined organic layers were dried over $MgSO_4$ and concentrated to provide the crude amine (1.20 g, 98%), which was used in the following step without further purification.

$^1$H NMR (CDCl$_3$, 400 MHz): δ 7.47-7.28 (m, 11H), 6.86 (d, J=8.4 Hz, 1H), 5.10 (s, 2H), 4.99 (s, 2H), 3.62 (q, J=5.6 Hz, 2H), 3.02 (t, J=5.6 Hz, 2H), 2.55 (s, 3H).

Step 5

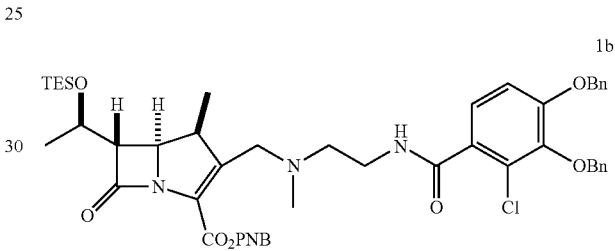

1b

A degassed solution of Pd$_2$(dba)$_3$.CHCl$_3$ (104 mg, 0.10 mmol) and dppb (128 mg, 0.30 mmol) in toluene (10 mL) was stirred for 1 h at r.t. under $N_2$. The solution was then transferred into another degassed solution of CPI (591 mg, 1.0 mmol) and crude amine (425 mg, 1.0 mmol) in THF (5 mL). TEA (139 □L, 1.0 mmol) was subsequently added. After stirring overnight, the reaction mixture was concentrated and purified on a silica gel column ($CH_2Cl_2$/MeOH=100/0 to 98/2) to afford 1b (800 mg, 89%) as an orange paste.

$^1$H NMR (CDCl$_3$, 400 MHz): δ 8.19 (d, J=8.4 Hz, 2H), 7.65 (d, J=8.4 Hz, 2H), 7.53 (d, J=8.4 Hz, 1H), 7.46-7.30 (m, 10H), 6.96 (d, J=8.4 Hz, 1H), 6.90 (t, J=4.4 Hz, 1H), 5.42 (d, J=13.6 Hz, 1H), 5.18 (d, J=14.4 Hz, 1H), 5.15 (s, 2H), 5.02 (s, 2H), 4.28-4.21 (m, 1H), 4.19 (dd, J=10.4, 3.2 Hz, 1H), 3.91 (d, J=14.4 Hz, 1H), 3.64-3.48 (m, 2H), 3.31-3.23 (m, 1H), 3.21 (dd, J=5.6, 3.2 Hz, 1H), 3.15 (dd, J=14.0, 1.2 Hz, 1H), 2.68-2.54 (m, 2H), 2.23 (s, 3H), 1.22 (d, J=6.4 Hz, 3H), 1.11 (d, J=7.2 Hz, 3H), 0.92 (t, J=8.0 Hz, 9H), 0.58 (q, J=8.0 Hz, 6H).

Step 6

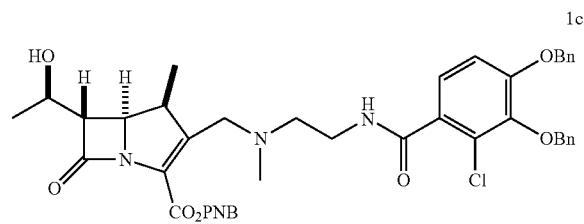

1c

Into a solution of 1b (800 mg, 0.89 mmol) in THF (25 mL) were added AcOH (102 μL, 1.78 mmol) and TBAF (1.0 M in THF) (2.67 mL, 2.67 mmol), respectively, at 0° C. After stirring for 2 h at r.t., the reaction solution was quenched with 0.25M SPB (pH 7.0, 80 mL) and extracted with EtOAc (2×40 mL). The combined organics were dried over MgSO$_4$ and concentrated in vacuo. The crude was purified on a silica gel column (CH$_2$Cl$_2$/MeOH=100/0 to 97/3) to afford 1c (520 mg, 75%) as an off-white foam.

$^1$H NMR (CDCl$_3$, 400 MHz): δ 8.20 (d, J=8.0 Hz, 2H), 7.64 (d, J=8.0 Hz, 2H), 7.64 (d, J=8.8 Hz, 1H), 7.46-7.31 (m, 10H), 6.96 (d, J=8.8 Hz, 1H), 6.85 (t, J=4.0 Hz, 1H), 5.46 (d, J=13.6 Hz, 1H), 5.20-5.15 (m, 3H), 5.03 (s, 2H), 4.24-4.14 (m, 2H), 3.91 (d, J=14.8 Hz, 1H), 3.64-3.46 (m, 2H), 3.35-3.25 (m, 1H), 3.22 (dd, J=6.0, 2.8 Hz, 1H), 3.13 (d, J=14.8 Hz, 1H), 2.68-2.51 (m, 2H), 2.23 (s, 3H), 1.91 (br s, 1H), 1.30 (d, J=6.4 Hz, 3H), 1.10 (d, J=7.6 Hz, 3H).

Step 7

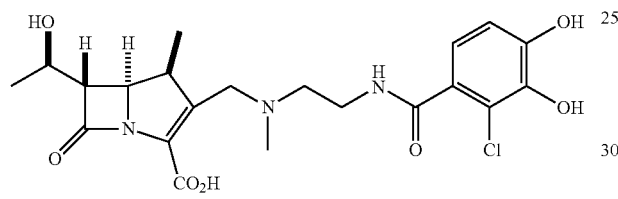

1

Into a mixture of 1c (392 mg, 0.5 mmol) in THF (20 mL), 0.25M SPB (pH 7.0) (20 mL), and IPA (10 mL) was added Pd(OH)$_2$/C (20 wt %, 351 mg) at 0° C. After stirring for 1 h at 0° C. under H$_2$, the reaction mixture was diluted with DI water and EtOAc (20 mL each) and then filtered through Celite. The filter cake was washed with DI water and EtOAc repeatedly (60 mL each). After the phase separation, the aqueous phase was lyophilized. The crude material was purified on a resin column (SP-207) to afford 1 (typically 35-50% yield) as a slightly purple or white fluffy solid.

$^1$H NMR (D$_2$O, 400 MHz): δ 6.85 (d, J=7.6 Hz, 1H), 6.78 (d, J=8.0 Hz, 1H), 4.20-4.28 (m, 2H), 4.01-3.96 (m, 2H), 3.80-3.70 (m, 2H), 3.51-3.47 (m, 1H), 3.40-3.16 (m, 3H), 2.85 (s, 3H), 1.28 (d, J=6.8 Hz, 3H), 1.18 (d, J=7.2 Hz, 3H).

Example 2: Synthesis of 2

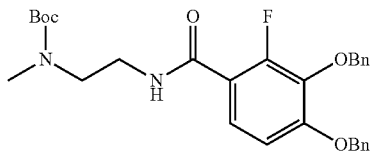

2a $^1$H NMR (CDCl$_3$, 400 MHz): δ 7.80-7.70 (br, 1H), 7.42-7.29 (m, 10H), 6.86-6.79 (br, 1H), 5.15 (s, 2H), 5.06 (s, 2H), 3.63-3.55 (br, 2H), 3.54-3.45 (br, 2H), 2.90 (s, 3H), 1.42 (s, 9H).

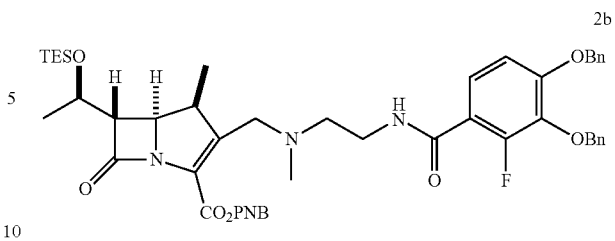

2b $^1$H NMR (CDCl$_3$, 400 MHz): δ 8.20 (d, J=8.4 Hz, 2H), 7.81 (t, J=8.8 Hz, 1H), 7.66 (d, J=8.4 Hz, 2H), 7.42-7.28 (m, 10H), 7.15-7.08 (m, 1H), 6.85 (d, J=9.2 Hz, 1H), 5.45 (d, J=14.0 Hz, 1H), 5.21 (d, J=14.4 Hz, 1H), 5.16 (s, 2H), 5.06 (s, 2H), 4.24 (t, J=6.0 Hz, 1H), 4.21 (dd, J=10.0, 2.8 Hz, 1H), 3.92 (d, J=14.4 Hz, 1H), 3.64-3.48 (m, 2H), 3.39-3.29 (m, 1H), 3.23-3.15 (m, 2H), 2.68-2.50 (m, 2H) 2.23 (s, 3H), 1.18 (d, J=6.0 Hz, 3H), 1.14 (d, J=7.6 Hz, 3H), 0.91 (t, J=8.0 Hz, 9H), 0.57 (q, J=7.6 Hz, 6H).

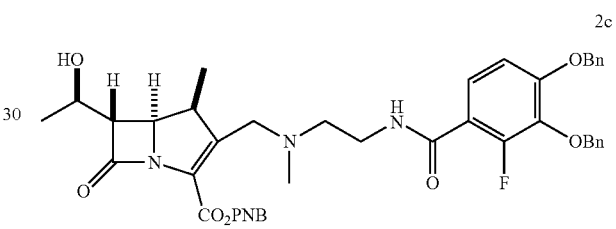

2c $^1$H NMR (CDCl$_3$, 400 MHz): δ 8.21 (d, J=9.2 Hz, 2H), 7.80 (t, J=8.8 Hz, 1H), 7.65 (d, J=8.4 Hz, 2H), 7.43-7.29 (m, 10H), 7.15-7.08 (m, 1H), 6.86 (dd, J=8.8, 1.2 Hz, 1H), 5.49 (d, J=13.6 Hz, 1H), 5.21 (d, J=14.0 Hz, 1H), 5.17 (s, 2H), 5.07 (s, 2H), 4.20-4.14 (m, 2H), 3.92 (d, J=15.2 Hz, 1H), 3.61-3.51 (m, 2H), 3.44-3.35 (m, 1H), 3.22 (dd, J=6.4, 3.2 Hz, 1H), 3.16 (d, J=14.4 Hz, 1H), 2.68-2.50 (m, 2H), 2.24 (s, 3H), 1.70 (br s, 1H), 1.27 (d, J=6.0 Hz, 3H), 1.13 (d, J=7.6 Hz, 3H).

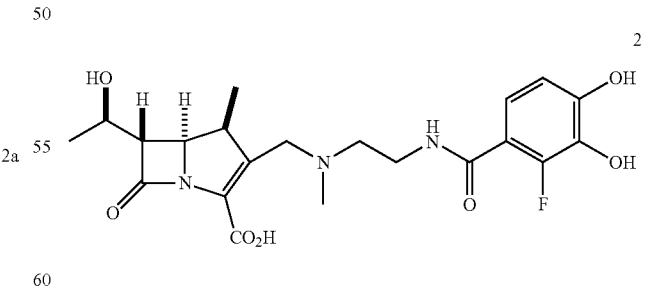

2

$^1$H NMR (D$_2$O, 400 MHz): δ 7.18-7.08 (m, 1H), 6.74-6.65 (m, 1H), 4.27-4.15 (m, 2H), 4.05-3.92 (m, 2H), 3.82-3.69 (m, 2H), 3.49-3.44 (m, 1H), 3.43-3.10 (m, 3H), 2.89 (s, 3H), 1.27 (d, J=6.0 Hz, 3H), 1.16 (d, J=7.6 Hz, 3H).

Example 3: Synthesis of 3

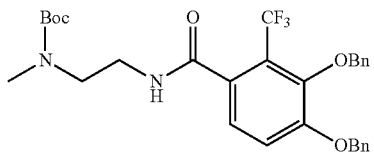
3a

¹H NMR (CDCl₃, 400 MHz): δ 7.44-7.30 (m, 10H), 7.11 (s, 2H), 5.16 (s, 2H), 5.06 (s, 2H), 3.61-3.53 (br, 2H), 3.52-3.42 (br, 2H), 2.92 (s, 3H), 1.40 (s, 9H).

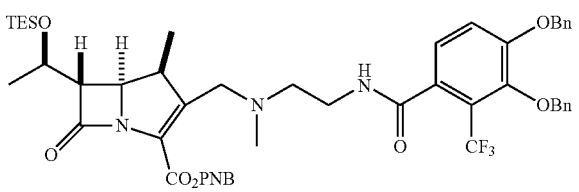
3b

¹H NMR (CDCl₃, 400 MHz): δ 8.17 (d, J=8.8 Hz, 2H), 7.63 (d, J=8.8 Hz, 2H), 7.43-7.30 (m, 10H), 7.17 (d, J=8.8 Hz, 1H), 7.14 (d, J=8.4 Hz, 1H), 6.20 (t, J=4.8 Hz, 1H), 5.35 (d, J=13.6 Hz, 1H), 5.15 (s, 2H), 5.11 (d, J=14.0 Hz, 1H), 5.07 (s, 2H), 4.27-4.22 (m, 1H), 4.18 (dd, J=10.0, 2.8 Hz, 1H), 3.87 (d, J=14.4 Hz, 1H), 3.58-3.46 (m, 2H), 3.23-3.16 (m, 2H), 3.10 (d, J=14.8 Hz, 1H), 2.65-2.52 (m, 2H) 2.20 (s, 3H), 1.22 (d, J=6.4 Hz, 3H), 1.08 (d, J=7.6 Hz, 3H), 0.92 (t, J=7.6 Hz, 9H), 0.58 (q, J=8.0 Hz, 6H).

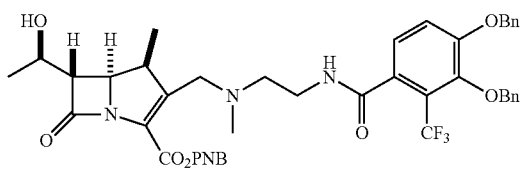
3c

¹H NMR (CDCl₃, 400 MHz): δ 8.19 (d, J=8.8 Hz, 2H), 7.62 (d, J=8.4 Hz, 2H), 7.43-7.30 (m, 10H), 7.18 (d, J=8.8, Hz, 1H), 7.13 (d, J=8.8 Hz, 1H), 6.17 (t, J=5.6 Hz, 1H), 5.41 (d, J=13.6 Hz, 1H), 5.16 (s, 2H), 5.12 (d, J=14.0 Hz, 1H), 5.07 (s, 2H), 4.23 (t, J=6.4 Hz, 1H), 4.17 (dd, J=10.4, 3.2 Hz, 1H), 3.88 (d, J=14.4 Hz, 1H), 3.58-3.43 (m, 2H), 3.28-3.19 (m, 2H), 3.10 (d, J=14.4 Hz, 1H), 2.65-2.50 (m, 2H), 2.20 (s, 3H), 1.32 (d, J=6.0 Hz, 3H), 1.09 (d, J=7.2 Hz, 3H).

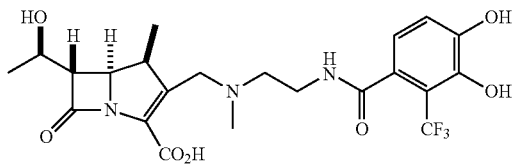
3

¹H NMR (D₂O, 400 MHz): δ 6.93 (d, J=7.6 Hz, 1H), 6.61 (d, J=7.2 Hz, 1H), 4.30-4.22 (m, 2H), 4.10-3.95 (m, 2H), 3.77-3.68 (m, 2H), 3.53-3.48 (m, 1H), 3.40-3.17 (m, 3H), 2.87 (s, 3H), 1.29 (d, J=6.4 Hz, 3H), 1.20 (d, J=7.6 Hz, 3H).

Example 4: Synthesis of 4

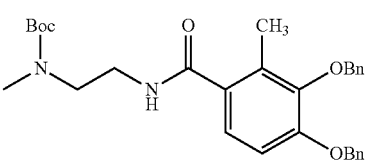
4a

¹H NMR (400 MHz, CDCl₃): δ 7.44-7.25 (m, 10H), 7.11 (d, J=7.6 Hz, 1H), 6.79 (d, J=7.6 Hz, 1H), 5.13 (s, 2H), 4.94 (s, 2H), 3.59-3.53 (m, 2H), 3.49-3.43 (m, 2H), 2.91 (s, 3H), 2.37 (s, 3H), 1.41 (s, 9H).

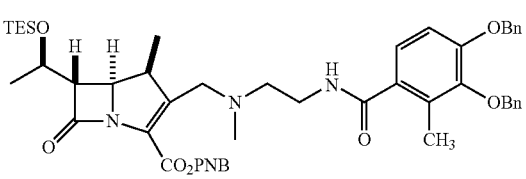
4b

¹H NMR (CDCl₃, 400 MHz): δ 8.17 (d, J=8.4 Hz, 2H), 7.63 (d, J=8.8 Hz, 2H), 7.42-7.30 (m, 10H), 7.09 (d, J=8.0 Hz, 1H), 6.81 (d, J=8.4 Hz, 1H), 6.23 (br, 1H), 5.37 (d, J=14.4 Hz, 1H), 5.14-5.10 (m, 3H), 4.95 (s, 2H), 4.24 (t, J=6.0 Hz, 1H), 4.18 (dd, J=10.4, 3.2 Hz, 1H), 3.88 (d, J=14.4 Hz, 1H), 3.53-3.50 (m, 2H), 3.25-3.20 (m, 2H), 3.11 (d, J=14.0 Hz), 2.63-2.52 (m, 2H) 2.36 (s, 3H), 2.21 (s, 3H), 1.22 (d, J=6.0 Hz, 3H), 1.10 (d, J=6.8 Hz, 3H), 0.92 (t, J=7.6 Hz, 9H), 0.58 (q, J=8.0 Hz, 6H).

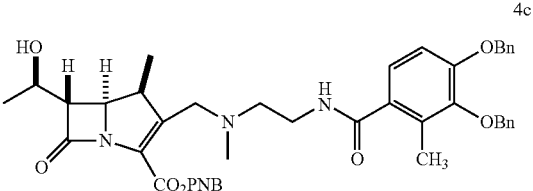
4c

¹H NMR (CDCl₃, 400 MHz): δ 8.18 (d, J=8.4 Hz, 2H), 7.61 (d, J=8.8 Hz, 2H), 7.49-7.30 (m, 10H), 7.09 (d, J=8.0 Hz, 1H), 6.82 (d, J=8.8 Hz, 1H), 6.31 (br, 1H), 5.42 (d, J=14.0 Hz, 2H), 5.14-5.09 (m, 3H), 4.95 (d, J=2H), 4.18 (t, J=6.4 Hz, 1H), 4.12 (dd, J=10.4, 3.2 Hz, 1H), 3.91 (d, J=14.4 Hz, 1H), 3.58-3.45 (m, 2H), 3.25-3.20 (m, 2H), 3.11 (d, J=14.4 Hz), 2.69-2.50 (m, 2H) 2.35 (s, 3H), 2.23 (s, 3H), 1.28 (d, J=6.4 Hz, 3H), 1.08 (d, J=7.6 Hz, 3H).

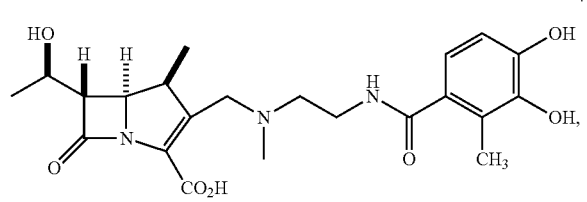

4

¹H NMR (400 MHz, D₂O) δ 6.93 (d, J=8.4 Hz, 1H), 6.77 (d, J=8.8 Hz, 1H), 4.25-4.19 (m, 2H), 3.86-3.82 (m, 2H), 3.68 (br, 2H), 3.48-3.46 (m, 1H), 3.24-3.19 (m, 2H), 3.17-3.03 (m, 1H), 2.74 (s, 3H), 2.22 (s, 3H), 1.27 (d, J=6 Hz, 3H), 1.17 (d, J=7.6 Hz, 3H).

Example 5: Synthesis of 5

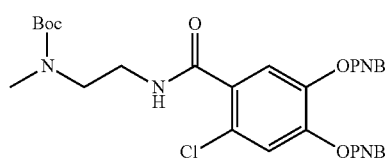

5a

¹H NMR (CDCl₃, 400 MHz): δ 8.30-8.23 (m, 4H), 7.61 (d, J=8.4 Hz, 4H), 7.48-7.41 (br, 1H), 7.10-7.05 (br, 1H), 6.90 (s, 1H), 5.26 (s, 4H), 3.63-3.56 (m, 2H), 3.52-3.46 (br, 2H), 2.91 (s, 3H), 1.41 (s, 9H).

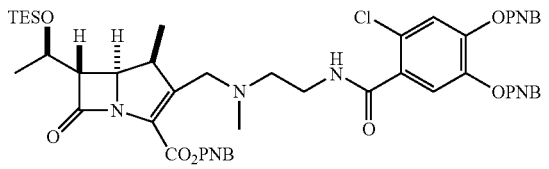

5b

¹H NMR (CDCl₃, 400 MHz): δ 8.29-8.19 (m, 6H), 7.67-7.59 (m, 7H), 7.19 (t, J=5.6 Hz, 1H), 6.89 (s, 1H), 5.44 (d, J=14.0 Hz, 1H), 5.27 (s, 2H), 5.25 (s, 2H), 5.21 (d, J=14.0 Hz, 1H), 4.27-4.21 (m, 1H), 4.17 (dd, J=10.4, 2.8 Hz, 1H), 3.92 (d, J=14.8 Hz, 1H), 3.62-3.51 (m, 2H), 3.34-3.25 (m, 1H), 3.22 (dd, J=6.0, 3.2 Hz, 1H), 3.16 (d, J=14.8 Hz, 1H), 2.68-2.54 (m, 2H) 2.22 (s, 3H), 1.25 (d, J=6.4 Hz, 3H), 1.12 (d, J=7.6 Hz, 3H), 0.93 (t, J=8.0 Hz, 9H), 0.59 (q, J=8.0 Hz, 6H).

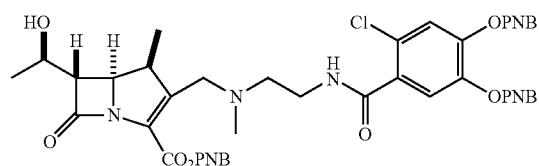

5c

¹H NMR (CDCl₃, 400 MHz): δ 8.29-8.20 (m, 6H), 7.67-7.60 (m, 6H), 7.57 (s, 1H), 7.13 (t, J=5.2 Hz 1H), 6.90 (s, 1H), 5.47 (d, J=14.0 Hz, 1H), 5.27 (s, 2H), 5.26 (s, 2H), 5.21 (d, J=13.6 Hz, 1H), 4.28-4.22 (m, 1H), 4.16 (dd, J=10.0, 2.8 Hz, 1H), 3.92 (d, J=14.8 Hz, 1H), 3.62-3.51 (m, 2H), 3.38-3.28 (m, 1H), 3.24 (dd, J=6.8, 3.2 Hz, 1H), 3.16 (d, J=14.8 Hz, 1H), 2.69-2.52 (m, 2H), 2.23 (s, 3H), 1.66 (d, J=5.2 Hz, 1H), 1.35 (d, J=6.0 Hz, 3H), 1.13 (d, J=7.2 Hz, 3H).

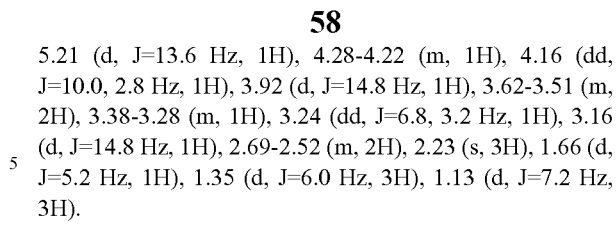

5

¹H NMR (D₂O, 400 MHz): δ 7.00 (s, 1H), 6.80 (s, 1H), 4.28-4.18 (m, 2H), 3.94-3.61 (m, 4H), 3.49-3.44 (m, 1H), 3.27-3.14 (m, 2H), 3.10-2.98 (m, 1H), 2.69 (s, 3H), 1.27 (d, J=6.4 Hz, 3H), 1.16 (d, J=6.8 Hz, 3H).

Example 6: Synthesis of 6

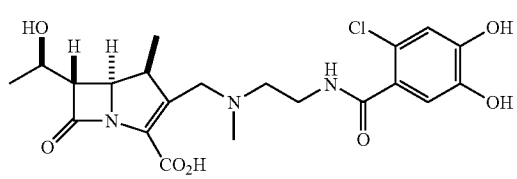

6a

¹H NMR (CDCl₃, 400 MHz): δ 8.23 (d, J=8.4 Hz, 2H), 8.20 (d, J=8.4 Hz, 2H), 7.73-7.68 (br, 1H), 7.62 (d, J=8.8 Hz, 2H), 7.57 (d, J=8.4 Hz, 2H), 7.51 (br s, 1H), 7.48 (br s, 1H), 5.26 (s, 2H), 5.20 (s, 2H), 3.60-3.50 (m, 4H), 2.93 (s, 3H), 1.47 (s, 9H).

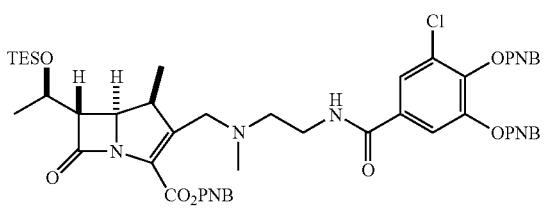

6b

¹H NMR (CDCl₃, 400 MHz): δ 8.26-8.18 (m, 6H), 7.67-7.54 (m, 7H), 7.30 (d, J=2.0 Hz, 1H), 6.77 (t, J=4.8 Hz, 1H), 5.45 (d, J=14.4 Hz, 1H), 5.28-5.23 (m, 3H), 5.20 (s, 2H), 4.29-4.21 (m, 2H), 3.95 (d, J=14.8 Hz, 1H), 3.58-3.51 (m, 2H), 3.34-3.24 (m, 2H), 3.12 (d, J=14.4 Hz, 1H), 2.68-2.55 (m, 2H), 2.24 (s, 3H), 1.24 (d, J=6.0 Hz, 3H), 1.20 (d, J=7.2 Hz, 3H), 0.92 (t, J=8.0 Hz, 9H), 0.60 (q, J=8.0 Hz, 6H).

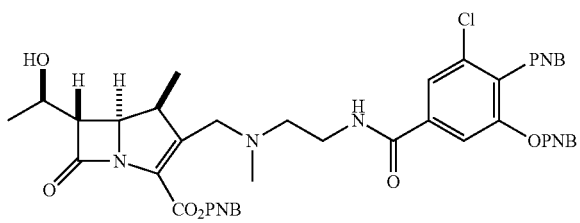

6c

¹H NMR (CDCl₃, 400 MHz): δ 8.26-8.18 (m, 6H), 7.66-7.55 (m, 6H), 7.53 (d, J=1.6 Hz, 1H), 7.30 (d, J=2.0 Hz, 1H), 6.70 (t, J=4.8 Hz 1H), 5.49 (d, J=13.6 Hz, 1H), 5.27 (s, 2H), 5.22 (d, J=13.6 Hz, 1H), 5.21 (s, 2H), 4.30-4.22 (m, 1H), 4.20 (dd, J=9.2, 2.4 Hz, 1H), 3.96 (d, J=14.4 Hz, 1H), 3.57-3.50 (m, 2H), 3.38-3.29 (m, 1H), 3.28 (dd, J=6.0, 2.8 Hz, 1H), 3.12 (d, J=14.4 Hz, 1H), 2.68-2.53 (m, 2H), 2.25 (s, 3H), 1.74 (d, J=3.6 Hz, 1H), 1.33 (d, J=6.4 Hz, 3H), 1.19 (d, J=7.2 Hz, 3H).

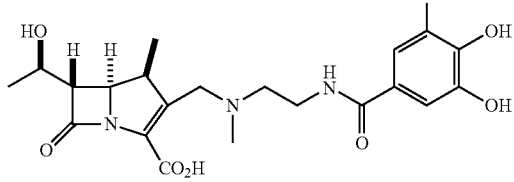

6

¹H NMR (D₂O, 400 MHz): δ 7.39 (s, 1H), 7.15 (s, 1H), 4.25-4.09 (m, 2H), 4.02-3.82 (m, 2H), 3.78-3.62 (m, 2H), 3.47-3.42 (m, 1H), 3.37-3.10 (m, 3H), 2.81 (s, 3H), 1.25 (d, J=6.4 Hz, 3H), 1.14 (d, J=5.2 Hz, 3H).

Example 7: Synthesis of 7

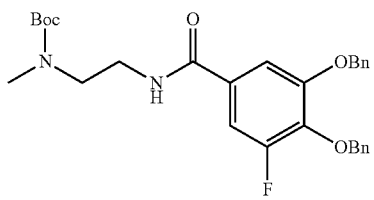

7a

¹H NMR (400 MHz, CDCl₃): δ 7.52-7.15 (comp, 12H), 5.14 (s, 4H), 3.59-3.45 (comp, 4H) 2.90 (s, 3H) 1.44 (s, 9H).

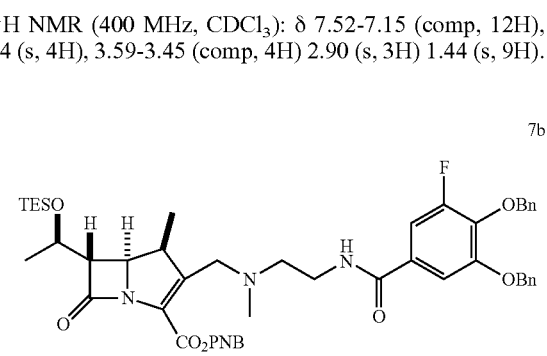

7b

¹H NMR (400 MHz, CDCl₃): δ 8.20 (d, J=8.8 Hz, 2H), 7.65 (d, J=8.8 Hz, 2H), 7.42-7.29 (m, 11H), 7.03 (dd, J=11.2, 1.6 Hz, 1H), 6.56 (br, 1H), 5.44 (d, J=14.0 Hz, 1H), 5.19 (d, 14.0 Hz, 1H), 5.15 (s, 4H), 4.27-4.19 (m, 2H), 3.93 (d, J=14.4 Hz, 1H), 3.56-3.50 (m, 2H), 3.28-3.20 (m, 2H), 3.09 (d, J=14.0 Hz, 1H), 2.63-2.52 (m, 2H), 2.23 (s, 3H), 1.22 (d, J=6.0 Hz, 3H), 1.14 (d, J=7.2 Hz, 3H), 0.92 (t, J=7.6 Hz, 9H), 0.58 (q, J=7.6 Hz, 6H).

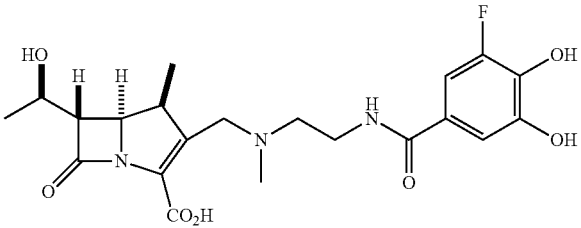

7c

¹H NMR (400 MHz, CDCl₃): δ 8.21 (d, J=8.8 Hz, 2H), 7.64 (d, J=8.4 Hz, 2H) 7.43-7.29 (m, 11H), 7.04 (d, J=12.8 Hz, 1H), 6.60 (m, 1H), 5.47 (d, J=13.6 Hz, 1H), 5.19 (d, J=14.0 Hz, 1H), 4.29-4.13 (m, 2H), 3.93 (d, J=14.4 Hz, 1H), 3.56-3.50 (m, 2H), 3.35-3.23 (m, 2H), 3.08 (d, J=14.0 Hz, 1H), 2.68-2.53 (m, 2H), 2.24 (s, 3H), 1.31 (d, J=6.4 Hz, 3H), 1.13 (d, J=7.2 Hz, 3H).

7

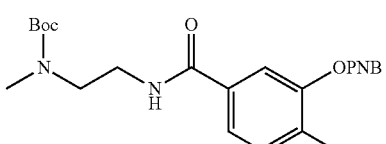

¹H NMR (400 MHz, D₂O): δ 7.18-7.02 (m, 2H), 4.21-4.10 (m, 2H), 4.01-3.91 (m, 2H), 3.71 (br, 2H), 3.44 (s, 1H), 3.40-3.13 (m, 3H), 2.88 (s, 3H), 1.27-1.12 (m, 6H)

Example 8: Synthesis of 8

8a

¹H NMR (CDCl₃, 400 MHz): δ 8.27-8.22 (m, 4H), 7.64 (d, J=8.8 Hz, 2H), 7.62 (d, J=8.8 Hz, 2H), 7.57 (br s, 1H), 7.50-7.42 (br, 1H), 7.40-7.35 (br, 1H), 6.89 (d, J=8.8 Hz, 1H), 5.30 (s, 2H), 5.28 (s, 2H), 3.59-3.46 (m, 4H), 2.91 (s, 3H), 1.42 (s, 9H).

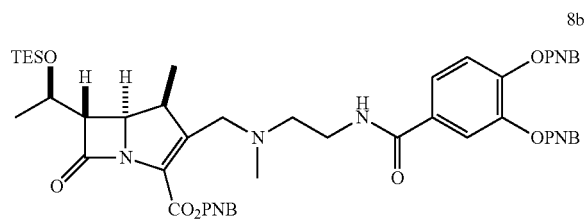

8b

¹H NMR (CDCl₃, 400 MHz): δ 8.27-8.18 (m, 6H), 7.66-7.59 (m, 6H), 7.58 (d, J=2.0 Hz, 1H), 7.21 (dd, J=8.4, 2.0 Hz, 1H), 6.88 (d, J=8.8 Hz, 1H), 6.54 (t, J=4.8 Hz, 1H), 5.42 (d, J=14.4 Hz, 1H), 5.30 (s, 2H), 5.28 (s, 2H), 5.20 (d, J=13.6 Hz, 1H), 4.27-4.21 (m, 1H), 4.17 (dd, J=10.8, 3.2 Hz, 1H), 3.91 (d, J=14.4 Hz, 1H), 3.59-3.47 (m, 2H), 3.30-3.20 (m, 2H), 3.16 (d, J=14.4 Hz, 1H), 2.68-2.52 (m, 2H), 2.24 (s, 3H), 1.23 (d, J=6.0 Hz, 3H), 1.15 (d, J=6.8 Hz, 3H), 0.92 (t, J=8.0 Hz, 9H), 0.58 (q, J=8.0 Hz, 6H).

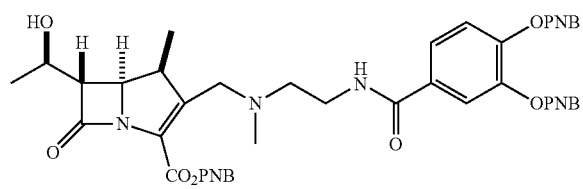

8c

¹H NMR (CDCl₃, 400 MHz): δ 8.27-8.19 (m, 6H), 7.66-7.60 (m, 6H), 7.56 (d, J=1.6 Hz, 1H), 7.23-7.19 (m, 1H), 6.90 (d, J=8.4 Hz, 1H), 6.50 (t, J=5.6 Hz, 1H), 5.46 (d, J=14.0 Hz, 1H), 5.30 (s, 2H), 5.29 (s, 2H), 5.21 (d, J=13.6 Hz, 1H), 4.27-4.19 (m, 1H), 4.14 (dd, J=10.4, 3.2 Hz, 1H), 3.91 (d, J=14.4 Hz, 1H), 3.60-3.42 (m, 2H), 3.35-3.25 (m, 1H), 3.23 (dd, J=6.8, 2.8 Hz, 1H) 3.14 (d, J=14.8 Hz, 1H), 2.68-2.50 (m, 2H), 2.24 (s, 3H), 1.67 (d, J=4.8 Hz, 1H), 1.33 (d, J=6.4 Hz, 3H), 1.13 (d, J=7.6 Hz, 3H).

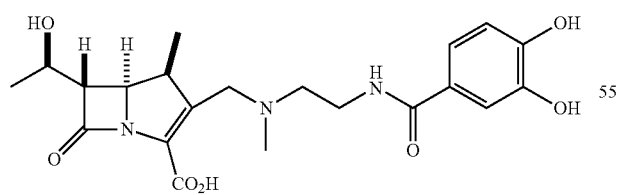

8

¹H NMR (D₂O, 400 MHz): δ 7.38-7.20 (br, 2H), 6.89 (s, 1H), 4.25-4.08 (m, 2H), 3.95-3.60 (m, 2H), 3.47-3.39 (m, 1H), 3.32-3.00 (m, 3H), 2.75 (s, 3H), 1.24 (d, J=5.6 Hz, 3H), 1.13 (s, 3H).

Example 9: Synthesis of 9

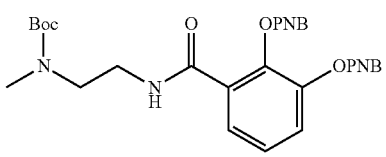

9a

¹H NMR (CDCl₃, 400 MHz): δ 8.22 (d, J=8.8 Hz, 2H), 8.19 (d, J=8.8 Hz, 2H), 7.68-7.52 (m, 5H), 7.19-7.04 (m, 2H), 5.21 (s, 4H), 3.55-3.40 (m, 2H), 3.37 (t, J=6.0 Hz, 2H), 2.85 (s, 3H), 1.37 (s, 9H).

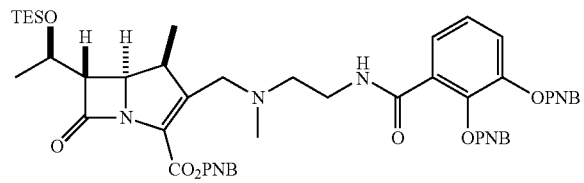

9b

¹H NMR (CDCl₃, 400 MHz): δ 8.26-8.16 (m, 6H), 7.68-7.52 (m, 8H), 7.19 (t, J=8.0 Hz, 1H), 7.08 (dd, J=8.4, 1.2 Hz, 1H), 5.41 (d, J=14.0 Hz, 1H), 5.24-5.14 (m, 5H), 4.27-4.20 (m, 1H), 4.11 (dd, J=10.0, 2.8 Hz, 1H), 3.83 (d, J=14.4 Hz, 1H), 3.57-3.39 (m, 2H), 3.21-3.13 (m, 2H), 3.05 (d, J=15.2 Hz, 1H), 2.55-2.36 (m, 2H), 2.08 (s, 3H), 1.20 (d, J=6.4 Hz, 3H), 1.05 (d, J=7.6 Hz, 3H), 0.92 (t, J=8.0 Hz, 9H), 0.58 (q, J=8.0 Hz, 6H).

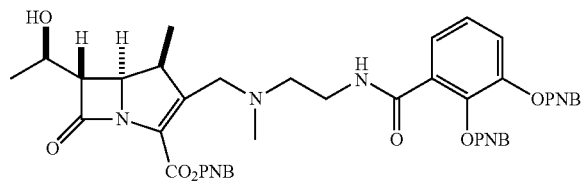

9c

¹H NMR (CDCl₃, 400 MHz): δ 8.25-8.18 (m, 6H), 7.69-7.53 (m, 8H), 7.20 (t, J=8.0 Hz, 1H), 7.09 (dd, J=6.8, 1.6 Hz, 1H), 5.45 (d, J=13.6 Hz, 1H), 5.22 (s, 2H), 5.18 (d, J=14.0 Hz, 1H), 5.16 (s, 2H), 4.24-4.16 (m, 1H), 4.01 (dd, J=10.0, 2.8 Hz, 1H), 3.82 (d, J=14.4 Hz, 1H), 3.57-3.40 (m, 2H), 3.18 (dd, J=7.2, 3.2 Hz, 1H), 3.17-3.08 (m, 1H), 3.04 (d, J=14.8 Hz, 1H), 2.56-2.35 (m, 2H), 2.08 (s, 3H), 1.73 (d, J=4.4 Hz, 1H), 1.33 (d, J=6.0 Hz, 3H), 1.03 (d, J=6.8 Hz, 3H).

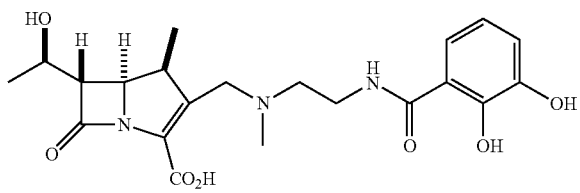

9

¹H NMR (D₂O, 400 MHz): δ 7.32-6.70 (m, 3H), 4.25-4.10 (m, 2H), 4.10-3.90 (m, 2H), 3.90-3.65 (m, 2H), 3.50-3.10 (m, 4H), 2.94 (s, 3H), 1.25 (d, J=4.4 Hz, 3H), 1.16 (d, J=6.0 Hz, 3H).

Example 10: Synthesis of 10

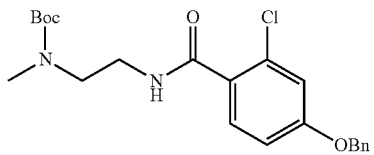

10a

¹H NMR (CDCl₃, 400 MHz): δ 7.67-7.60 (br, 1H), 7.43-7.31 (m, 5H), 6.98 (d, J=2.4 Hz, 1H), 6.95-6.83 (br, 1H), 5.07 (s, 2H), 3.59 (q, J=5.6 Hz, 2H), 3.53-3.45 (br, 2H), 2.91 (s, 3H), 1.41 (s, 9H).

10b

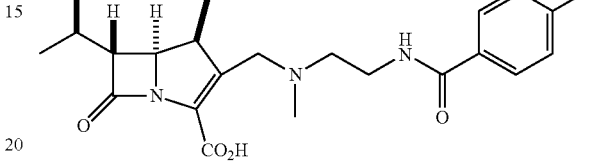

¹H NMR (CDCl₃, 400 MHz): δ 8.21 (d, J=9.2 Hz, 2H), 7.80 (d, J=8.8 Hz, 1H), 7.65 (d, J=8.8 Hz, 2H), 7.42-7.32 (m, 5H), 6.99-6.91 (m, 3H), 5.43 (d, J=14.0 Hz, 1H), 5.20 (d, J=13.6 Hz, 1H), 5.08 (s, 2H), 4.24 (p, J=6.0 Hz, 1H), 4.17 (dd, J=10.4, 3.2 Hz, 1H), 3.92 (d, J=14.4 Hz, 1H), 3.64-3.48 (m, 2H), 3.34-3.25 (m, 1H), 3.22 (dd, J=6.0, 3.2 Hz, 1H), 3.15 (d, J=14.4 Hz, 1H), 2.69-2.53 (m, 2H), 2.22 (s, 3H), 1.25 (d, J=6.4 Hz, 3H), 1.12 (d, J=7.2 Hz, 3H), 0.94 (t, J=8.0 Hz, 9H), 0.59 (q, J=8.0 Hz, 6H).

10c

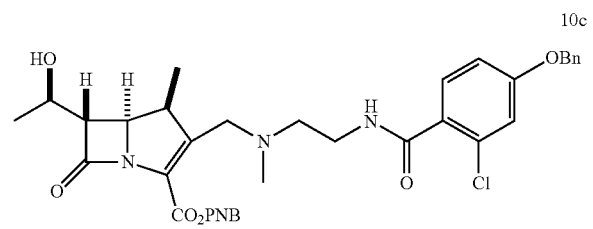

¹H NMR (CDCl₃, 400 MHz): δ 8.23 (d, J=8.8 Hz, 2H), 7.78 (d, J=8.4 Hz, 1H), 7.65 (d, J=8.4 Hz, 2H), 7.43-7.32 (m, 5H), 7.00 (d, J=2.4 Hz, 1H), 6.95-6.88 (m, 2H), 5.47 (d, J=14.0 Hz, 1H), 5.19 (d, J=14.0 Hz, 1H), 5.08 (s, 2H), 4.29-4.21 (m, 1H), 4.17 (dd, J=10.4, 2.8 Hz, 1H), 3.91 (d, J=14.8 Hz, 1H), 3.66-3.47 (m, 2H), 3.39-3.28 (m, 1H), 3.25 (dd, J=6.8, 3.2 Hz, 1H), 3.16 (d, J=14.0 Hz, 1H), 2.69-2.52 (m, 2H), 2.23 (s, 3H), 1.67 (d, J=5.2 Hz, 1H) 1.34 (d, J=6.8 Hz, 3H), 1.13 (d, J=7.2 Hz, 3H).

10

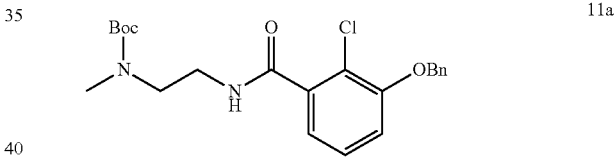

¹H NMR (D₂O, 400 MHz): δ 7.70 (d, J=8.8 Hz, 2H), 6.90 (d, J=8.4 Hz, 2H), 4.25-4.17 (m, 1H), 4.14 (dd, J=9.6, 2.8 Hz, 1H), 3.92-3.80 (m, 2H), 3.75-3.63 (m, 2H), 3.44 (dd, J=6.0, 2.8 Hz, 1H), 3.30-3.13 (m, 2H), 3.12-3.02 (m, 1H), 2.75 (s, 3H), 1.25 (d, J=6.8 Hz, 3H), 1.14 (d, J=7.2 Hz, 3H).

Example 11: Synthesis of 11

11a

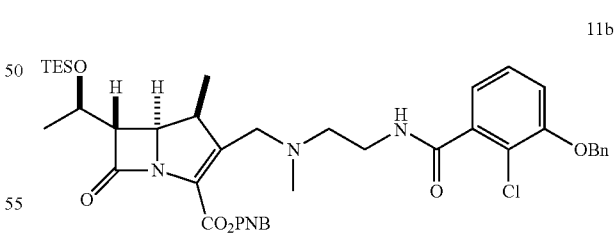

¹H NMR (CDCl₃, 400 MHz): δ 7.46-8.30 (m, 5H), 7.24-7.10 (m, 2H), 7.02-6.97 (br, 1H), 5.17 (s, 2H), 3.62 (q, J=5.6 Hz, 2H), 3.54-3.46 (br, 2H), 2.93 (s, 3H), 1.41 (s, 9H).

11b

¹H NMR (CDCl₃, 400 MHz): δ 8.20 (d, J=8.4 Hz, 2H), 7.64 (d, J=9.2 Hz, 2H), 7.46-7.30 (m, 5H), 7.24-7.22 (m, 2H), 7.04-7.00 (m, 1H), 6.67 (t, J=4.8 Hz, 1H), 5.40 (d, J=13.6 Hz, 1H), 5.17 (d, J=13.6 Hz, 1H), 5.16 (s, 2H), 4.24 (p, J=6.0 Hz, 1H), 4.18 (dd, J=10.4, 2.8 Hz, 1H), 3.90 (d, J=14.4 Hz, 1H), 3.65-3.50 (m, 2H), 3.31-3.22 (m, 1H), 3.21 (dd, J=5.6, 3.2 Hz, 1H), 3.14 (d, J=14.8 Hz, 1H), 2.69-2.54 (m, 2H), 2.23 (s, 3H), 1.22 (d, J=6.4 Hz, 3H), 1.11 (d, J=6.8 Hz, 3H), 0.92 (t, J=8.0 Hz, 9H), 0.58 (q, J=8.0 Hz, 6H).

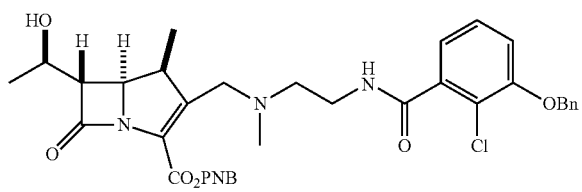
11c

¹H NMR (CDCl₃, 400 MHz): δ 8.21 (d, J=8.0 Hz, 2H), 7.63 (d, J=8.8 Hz, 2H), 7.46-7.30 (m, 5H), 7.24-7.21 (m, 2H), 7.03 (dd, J=6.4, 2.4 Hz, 1H), 6.63 (t, J=4.8 Hz, 1H), 5.45 (d, J=13.6 Hz, 1H), 5.17 (d, J=13.6 Hz, 1H), 5.16 (s, 2H), 4.25-4.19 (m, 1H), 4.18 (dd, J=10.4, 2.8 Hz, 1H), 3.91 (d, J=14.4 Hz, 1H), 3.66-3.48 (m, 2H), 3.36-3.26 (m, 1H), 3.23 (dd, J=5.6, 2.0 Hz, 1H), 3.14 (d, J=14.8 Hz, 1H), 2.69-2.52 (m, 2H), 2.23 (s, 3H), 1.81 (d J=3.6 Hz, 1H), 1.31 (d, J=6.4 Hz, 3H), 1.11 (d, J=7.2 Hz, 3H).

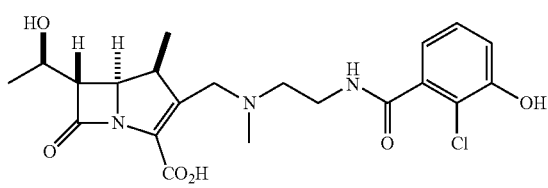
11

¹H NMR (D₂O, 400 MHz): δ 7.15 (t, J=8.4 Hz, 1H), 6.88 (d, J=8.4 Hz, 1H), 6.74-6.67 (m, 1H), 4.28-4.19 (m, 2H), 3.87 (d, J=14.8 Hz, 1H), 3.73-3.60 (m, 3H), 3.46 (dd, J=6.0, 2.4 Hz, 1H), 3.28-3.06 (m, 2H), 3.02-2.88 (m, 1H), 2.62 (s, 3H), 1.29 (d, J=6.4 Hz, 3H), 1.15 (d, J=7.2 Hz, 3H).

Example 12: Synthesis of 12

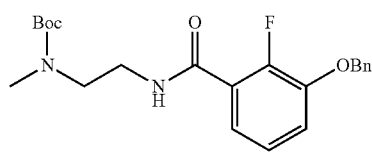
12a

¹H NMR (CDCl₃, 400 MHz): δ 7.65-7.54 (br, 1H), 7.45-7.31 (m, 5H), 7.14-7.06 (br, 2H), 5.14 (s, 2H), 3.65-3.58 (m, 2H), 3.54-3.46 (br, 2H), 2.92 (s, 3H), 1.43 (s, 9H).

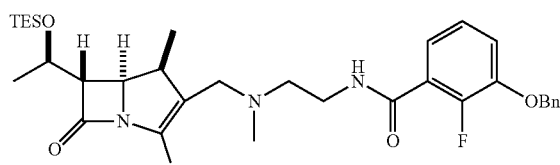
12b

¹H NMR (CDCl₃, 400 MHz): δ 8.20 (d, J=8.4 Hz, 2H), 7.67-7.62 (m, 3H), 7.43-7.31 (m, 5H), 7.25-7.20 (m, 1H), 7.14-7.11 (m, 2H), 5.45 (d, J=13.6 Hz, 1H), 5.21 (d, J=13.6 Hz, 1H), 5.13 (s, 2H), 4.24 (p, J=5.6 Hz, 1H), 4.19 (dd, J=10.0, 3.2 Hz, 1H), 3.92 (d, J=15.2 Hz, 1H), 3.67-3.51 (m, 2H), 3.39-3.30 (m, 1H), 3.21 (dd, J=5.2, 3.2 Hz, 1H), 3.17 (d, J=15.2 Hz, 1H), 2.69-2.52 (m, 2H), 2.24 (s, 3H), 1.18 (d, J=6.4 Hz, 3H), 1.14 (d, J=7.2 Hz, 3H), 0.91 (t, J=8.0 Hz, 9H), 0.57 (q, J=8.0 Hz, 6H).

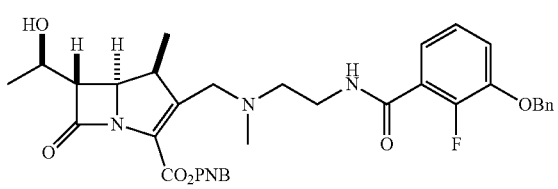
12c

¹H NMR (CDCl₃, 400 MHz): δ 8.21 (d, J=8.8 Hz, 2H), 7.67-7.62 (m, 3H), 7.44-7.32 (m, 5H), 7.25-7.18 (m, 1H), 7.15-7.12 (m, 2H), 5.49 (d, J=13.6 Hz, 1H), 5.20 (d, J=13.6 Hz, 1H), 5.13 (s, 2H), 4.22-4.15 (m, 2H), 3.92 (d, J=14.8 Hz, 1H), 3.64-3.52 (m, 2H), 3.45-3.36 (m, 1H), 3.22 (dd, J=6.4, 2.8 Hz, 1H), 3.16 (d, J=14.8 Hz, 1H), 2.69-2.52 (m, 2H), 2.23 (s, 3H), 1.71 (d, J=3.6 Hz, 1H), 1.27 (d, J=6.0 Hz, 3H), 1.14 (d, J=7.2 Hz, 3H).

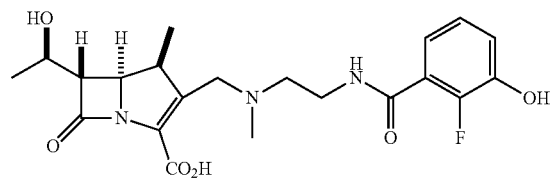
12

¹H NMR (D₂O, 400 MHz): δ 7.11-6.96 (m, 3H), 4.27-4.17 (m, 2H), 3.93 (d, J=14.8 Hz, 1H), 3.87 (d, J=14.8 Hz, 1H), 3.78-3.60 (m, 2H), 3.47 (dd, J=6.0, 2.8 Hz, 1H), 3.33-3.08 (m, 3H), 2.78 (s, 3H), 1.27 (d, J=6.0 Hz, 3H), 1.16 (d, J=4.8 Hz, 3H).

Example 13: Synthesis of 13

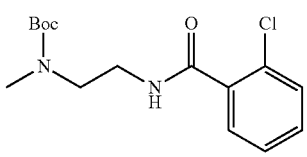
13a

¹H NMR (CDCl₃, 400 MHz): δ 7.67-7.56 (br, 1H), 7.42-7.26 (m, 3H), 6.86-6.74 (br, 1H), 3.62 (q, J=5.6 Hz, 2H), 3.54-3.47 (br, 2H), 2.93 (s, 3H), 1.42 (s, 9H).

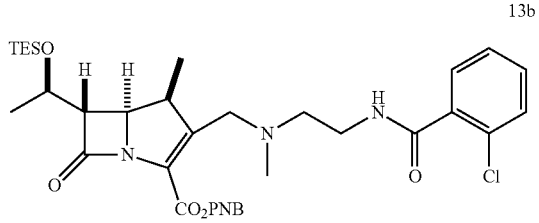

13b

¹H NMR (CDCl₃, 400 MHz): δ 8.22 (d, J=8.0 Hz, 2H), 7.75-7.70 (m, 1H), 7.65 (d, J=7.6 Hz, 2H), 7.41-7.30 (m, 3H), 6.83-6.78 (m, 1H), 5.42 (d, J=14.0 Hz, 1H), 5.18 (d, J=13.6 Hz, 1H), 4.27-4.19 (m, 1H), 4.16 (dd, J=10.0, 3.2 Hz, 1H), 3.92 (d, J=14.8 Hz, 1H), 3.66-3.50 (m, 2H), 3.32-3.24 (m, 1H), 3.21 (dd, J=6.0, 3.2 Hz, 1H), 3.15 (d, J=14.8 Hz, 1H), 2.71-2.54 (m, 2H), 2.23 (s, 3H), 1.24 (d, J=5.6 Hz, 3H), 1.11 (d, J=6.8 Hz, 3H), 0.94 (t, J=8.0 Hz, 9H), 0.59 (q, J=8.0 Hz, 6H).

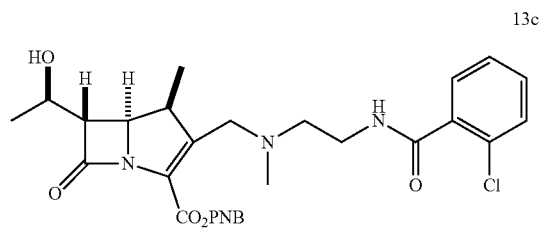 [SMILES: C[C@@H](O)[C@H]1C(=O)N2C(C(=O)O)=C(CN(C)CCNC(=O)c3ccccc3Cl)[C@H](C)[C@H]12]

13c

¹H NMR (CDCl₃, 400 MHz): δ 8.23 (d, J=9.2 Hz, 2H), 7.72 (dd, J=5.6, 2.0 Hz, 1H), 7.65 (d, J=8.8 Hz, 2H), 7.42-7.30 (m, 3H), 6.78-6.72 (m, 1H), 5.46 (d, J=13.6 Hz, 1H), 5.19 (d, J=13.6 Hz, 1H), 4.28-4.22 (m, 1H), 4.18 (dd, J=10.0, 2.8 Hz, 1H), 3.92 (d, J=14.8 Hz, 1H), 3.66-3.50 (m, 2H), 3.38-3.28 (m, 1H), 3.25 (dd, J=6.8, 3.2 Hz, 1H), 3.16 (d, J=14.8 Hz, 1H), 2.70-2.54 (m, 2H), 2.23 (s, 3H), 1.34 (d, J=6.4 Hz, 3H), 1.12 (d, J=7.6 Hz, 3H).

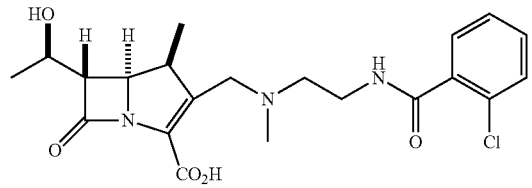

13

¹H NMR (D₂O, 400 MHz): δ 7.80-7.41 (m, 4H), 4.28-4.20 (m, 2H), 3.87 (d, J=12.0 Hz, 1H), 3.78-3.65 (m, 3H), 3.47 (dd, J=5.6, 2.0 Hz, 1H), 3.30-2.95 (m, 3H), 2.66 (br s, 3H), 1.29 (d, J=6.4 Hz, 3H), 1.17 (d, J=7.6 Hz, 3H).

Example 14: Synthesis of 14

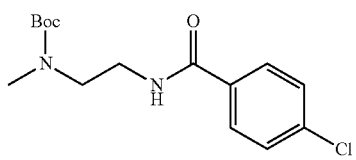

14a

¹H NMR (CDCl₃, 400 MHz): δ 7.76 (d, J=7.2 Hz, 2H), 7.54-7.48 (m, 1H), 7.38 (d, J=8.4 Hz, 2H), 3.62-3.48 (m, 4H), 2.91 (s, 3H), 1.44 (s, 9H).

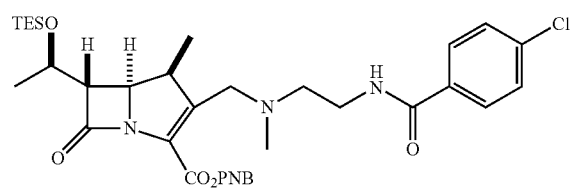

14b

¹H NMR (CDCl₃, 400 MHz): δ 8.22 (d, J=8.8 Hz, 2H), 7.71 (d, J=8.4 Hz, 2H), 7.65 (d, J=8.8 Hz, 2H), 7.40 (d, J=8.8 Hz, 2H), 6.67-6.62 (m, 1H), 5.43 (d, J=13.6 Hz, 1H), 5.19 (d, J=13.6 Hz, 1H), 4.24 (p, J=6.0 Hz, 1H), 4.15 (dd, J=10.0, 3.2 Hz, 1H), 3.93 (d, J=14.4 Hz, 1H), 3.64-3.46 (m, 2H), 3.28-3.19 (m, 2H), 3.14 (d, J=14.4 Hz, 1H), 2.70-2.53 (m, 2H), 2.25 (s, 3H), 1.23 (d, J=6.0 Hz, 3H), 1.13 (d, J=7.6 Hz, 3H), 0.93 (t, J=8.0 Hz, 9H), 0.59 (q, J=8.0 Hz, 6H).

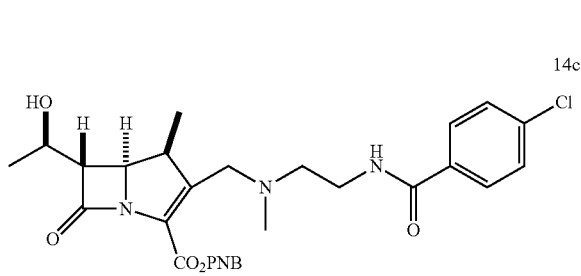

14c

¹H NMR (CDCl₃, 400 MHz): δ 8.22 (d, J=6.8 Hz, 2H), 7.71 (d, J=8.8 Hz, 2H), 7.64 (d, J=7.2 Hz, 2H), 7.40 (d, J=8.4 Hz, 2H), 6.63-6.57 (br, 1H), 5.46 (d, J=13.2 Hz, 1H), 5.19 (d, J=14.0 Hz, 1H), 4.28-4.20 (m, 1H), 4.18-4.12 (m, 1H), 3.92 (d, J=15.2 Hz, 1H), 3.62-3.46 (m, 3H), 3.34-3.22 (m, 2H), 3.14 (d, J=14.4 Hz, 1H), 2.69-2.50 (m, 2H), 2.25 (s, 3H), 1.33 (d, J=6.4 Hz, 3H), 1.14 (d, J=7.2 Hz, 3H).

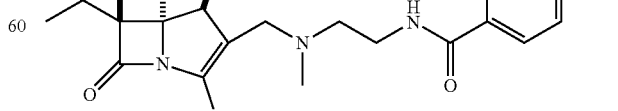

14

¹H NMR (D₂O, 400 MHz): δ 7.75 (d, J=8.8 Hz, 2H), 7.53 (d, J=8.4 Hz, 2H), 4.25-4.10 (m, 2H), 3.82 (d, J=13.6 Hz,

1H), 3.75-3.58 (m, 3H), 3.43 (dd, J=5.6, 2.4 Hz, 1H), 3.23-3.05 (m, 2H), 2.97-2.80 (m, 1H), 2.62 (br s, 3H), 1.25 (d, J=6.4 Hz, 3H), 1.13 (d, J=7.2 Hz, 3H).

Example 15: Synthesis of 15

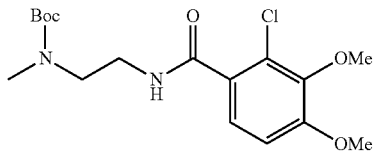

15a

<sup>1</sup>H NMR (400 MHz, CDCl<sub>3</sub>): δ 7.50-7.36 (br, 1H), 6.88-6.79 (m, 1H), 3.89 (s, 3H), 3.85 (s, 3H), 3.60 (q, J=6.0 Hz, 2H), 3.52-3.46 (m, 2H), 2.92 (s, 3H), 1.42 (s, 9H).

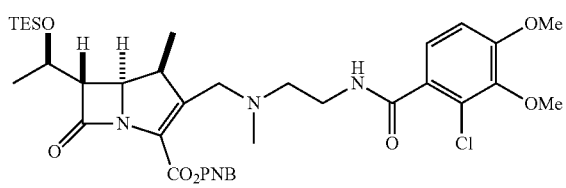

15b

<sup>1</sup>H NMR (CDCl<sub>3</sub>, 400 MHz): δ 8.21 (d, J=8.8 Hz, 2H), 7.66 (d, J=8.8 Hz, 2H), 7.56 (d, J=8.8 Hz, 1H), 6.91 (t, J=4.0 Hz, 1H), 6.88 (d, J=9.2 Hz, 1H), 5.43 (d, J=13.6 Hz, 1H), 5.20 (d, J=13.6 Hz, 1H), 4.28-4.21 (m, 1H), 4.18 (dd, J=9.6, 3.2 Hz, 1H), 3.91 (d, J=14.4 Hz, 1H), 3.90 (s, 3H), 3.85 (s, 3H), 3.64-3.49 (m, 2H), 3.34-3.24 (m, 1H), 3.22 (dd, J=5.6, 2.8 Hz, 1H), 3.16 (d, J=14.8 Hz, 1H), 2.69-2.53 (m, 2H), 2.23 (s, 3H), 1.24 (d, J=6.0 Hz, 3H), 1.12 (d, J=7.6 Hz, 3H), 0.93 (t, J=8.0 Hz, 9H), 0.59 (q, J=8.0 Hz, 6H).

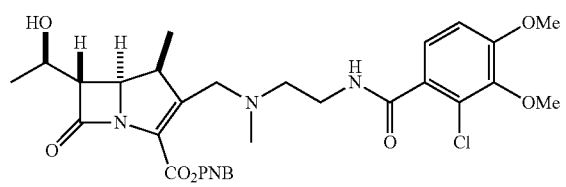

15c

<sup>1</sup>H NMR (CDCl<sub>3</sub>, 400 MHz): δ 8.22 (d, J=8.8 Hz, 2H), 7.65 (d, J=8.8 Hz, 2H), 7.54 (d, J=8.4 Hz, 1H), 6.89 (d, J=8.8 Hz, 1H), 6.84 (t, J=4.4 Hz, 1H), 5.47 (d, J=14.4 Hz, 1H), 5.19 (d, J=13.6 Hz, 1H), 4.28-4.20 (m, 1H), 4.16 (dd, J=10.4, 3.2 Hz, 1H), 3.91 (d, J=14.4 Hz, 1H), 3.90 (s, 3H), 3.86 (s, 3H), 3.64-3.48 (m, 2H), 3.36-3.27 (m, 1H), 3.24 (dd, J=6.0, 2.8 Hz, 1H), 3.15 (d, J=14.8 Hz, 1H), 2.69-2.51 (m, 2H), 2.23 (s, 3H), 1.78 (d, J=4.4 Hz, 1H), 1.34 (d, J=6.4 Hz, 3H), 1.12 (d, J=7.2 Hz, 3H).

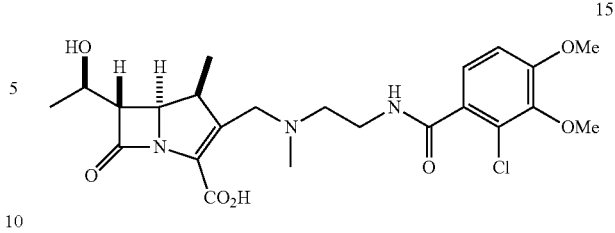

15

<sup>1</sup>H NMR (D<sub>2</sub>O, 400 MHz): δ 7.37 (d, J=8.4 Hz, 1H), 7.11 (d, J=8.4 Hz, 1H), 4.26-4.19 (m, 2H), 4.09 (d, J=14.4 Hz, 1H), 4.00-3.89 (m, 4H), 3.84 (s, 3H), 3.81-3.70 (m, 2H), 3.50-3.15 (m, 4H), 2.93 (s, 3H), 1.26 (d, J=6.0 Hz, 3H), 1.18 (d, J=6.8 Hz, 3H).

Example 16: Synthesis of 16

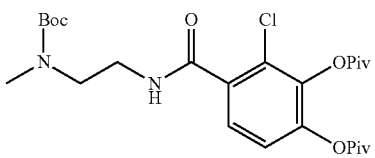

16a

<sup>1</sup>H NMR (400 MHz, CDCl<sub>3</sub>): δ 7.51 (d, J=9.6 Hz, 1H), 7.12 (d, J=9.2 Hz, 1H), 3.60 (q, J=6.0 Hz, 2H), 3.53-3.45 (m, 2H), 2.92 (s, 3H), 1.42 (s, 9H), 1.38 (s, 9H), 1.33 (s, 9H).

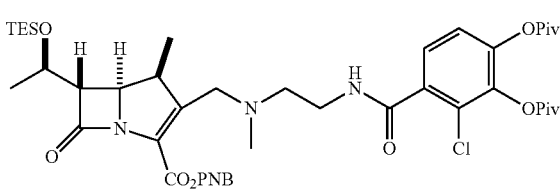

16b

<sup>1</sup>H NMR (CDCl<sub>3</sub>, 400 MHz): δ 8.21 (d, J=8.4 Hz, 2H), 7.66 (d, J=8.0 Hz, 2H), 7.56 (d, J=8.8 Hz, 1H), 7.14 (d, J=8.4 Hz, 1H), 6.71 (t, J=4.4 Hz, 1H), 5.41 (d, J=13.6 Hz, 1H), 5.17 (d, J=14.0 Hz, 1H), 4.30-4.23 (m, 1H), 4.21 (dd, J=10.8, 3.2 Hz, 1H), 3.91 (d, J=14.4 Hz, 1H), 3.60-3.54 (m, 2H), 3.29-3.20 (m, 2H), 3.12 (d, J=14.0 Hz, 1H), 2.68-2.55 (m, 2H), 2.22 (s, 3H), 1.38 (s, 9H), 1.33 (s, 9H), 1.22 (d, J=6.4 Hz, 3H), 1.11 (d, J=6.8 Hz, 3H), 0.93 (t, J=8.0 Hz, 9H), 0.59 (q, J=8.0 Hz, 6H).

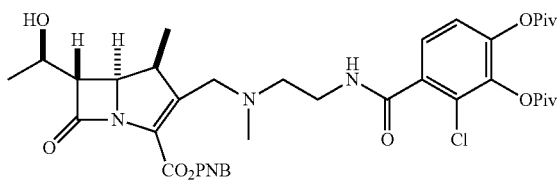

16c

<sup>1</sup>H NMR (CDCl<sub>3</sub>, 400 MHz): δ 8.23 (d, J=8.8 Hz, 2H), 7.66 (d, J=8.4 Hz, 2H), 7.58 (d, J=8.0 Hz, 1H), 7.15 (d, J=8.0 Hz, 1H), 6.75 (br t, 1H), 5.47 (d, J=14.0 Hz, 1H), 5.19 (d, J=13.2 Hz, 1H), 4.22-4.14 (m, 1H), 4.09 (dd, J=10.8, 3.2 Hz, 1H), 3.94 (d, J=14.4 Hz, 1H), 3.63-3.47 (m, 2H), 3.27-3.20 (m, 2H), 3.09 (d, J=14.8 Hz, 1H), 2.68-2.52 (m, 2H), 2.24 (s, 3H), 1.39 (s, 9H), 1.35-1.32 (m, 12H), 1.06 (d, J=7.2 Hz, 3H).

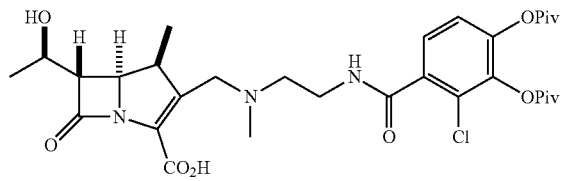

16

¹H NMR (D₂O, 400 MHz): δ 7.55 (br d, 1H), 7.31 (d, J=8.4 Hz, 1H), 4.28-4.14 (m, 2H), 3.87-3.73 (m, 1H), 3.72-3.37 (m, 4H), 3.28-3.14 (m, 1H), 3.10-2.92 (m, 1H), 2.92-2.72 (m, 1H). 2.49 (br s, 3H), 1.37 (s, 9H), 1.32 (s, 9H), 1.27 (d, J=6.0 Hz, 3H), 1.12 (d, J=7.2 Hz, 3H).

Example 17: Synthesis of 17

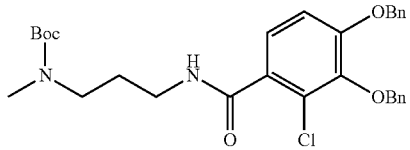

17a

¹H NMR (400 MHz, CDCl₃): δ 7.50-7.30 (m, 11H), 6.92 (d, J=8.8 Hz, 1H), 5.15 (s, 2H), 5.03 (s, 2H), 3.48-3.32 (m, 4H), 2.85 (s, 3H), 1.86-1.74 (m, 2H), 1.42 (s, 9H).

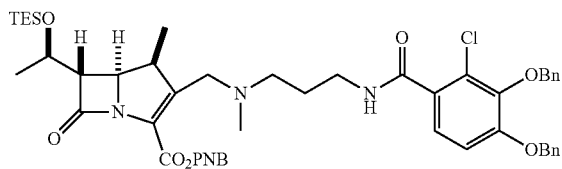

17b

¹H NMR (CDCl₃, 400 MHz): δ 8.20 (d, J=8.8 Hz, 2H), 7.65 (d, J=8.4 Hz, 2H), 7.46-7.29 (m, 11H), 7.03 (t, J=5.6 Hz, 1H), 6.93 (d, J=8.8 Hz, 1H), 5.42 (d, J=14.0 Hz, 1H), 5.19 (d, J=13.6 Hz, 1H), 5.14 (s, 2H), 5.03 (s, 2H), 4.23 (p, J=5.6 Hz, 1H), 4.15 (dd, J=10.4, 3.6 Hz, 1H), 3.81 (d, J=14.4 Hz, 1H), 3.60-3.46 (m, 2H), 3.32-3.15 (m, 2H), 3.10 (d, J=14.8 Hz, 1H), 2.59-2.51 (m, 1H), 2.48-2.39 (m, 1H), 2.19 (s, 3H), 1.80 (p, J=6.4 Hz, 1H), 1.20 (d, J=6.0 Hz, 3H), 1.02 (d, J=6.4 Hz, 3H), 0.93 (t, J=8.0 Hz, 9H), 0.58 (q, J=8.0 Hz, 6H).

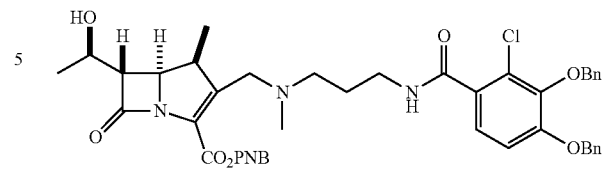

17c

¹H NMR (CDCl₃, 400 MHz): δ 8.21 (d, J=8.4 Hz, 2H), 7.64 (d, J=8.4 Hz, 2H), 7.47-7.30 (m, 12H), 6.95 (d, J=8.4 Hz, 1H), 5.46 (d, J=13.6 Hz, 1H), 5.18 (d, J=13.6 Hz, 1H), 5.15 (s, 2H), 5.02 (s, 2H), 4.12-4.03 (m, 1H), 4.00 (dd, J=10.4, 2.4 Hz, 1H), 3.80 (d, J=14.0 Hz, 1H), 3.65-3.45 (m, 2H), 3.14 (dd, J=6.8, 2.8 Hz, 1H), 3.09-3.01 (m, 2H), 2.62-2.45 (m, 2H), 2.17 (s, 3H), 1.95 (d, J=4.4 Hz, 1H), 1.89-1.71 (m, 2H), 1.26 (d, J=6.4 Hz, 3H), 0.94 (d, J=6.8 Hz, 3H).

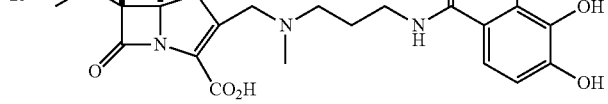

17

¹H NMR (D₂O, 400 MHz): δ 6.74 (d, J=7.6 Hz, 1H), 6.69 (d, J=8.4 Hz, 3H), 4.26-4.12 (m, 2H), 4.04-3.97 (m, 2H), 3.52-3.40 (m, 3H), 3.25-3.09 (m, 3H), 2.84 (s, 3H), 2.12-1.95 (m, 2H), 1.26 (d, J=6.0 Hz, 3H), 1.15 (d, J=6.8 Hz, 3H).

Example 18: Synthesis of 20

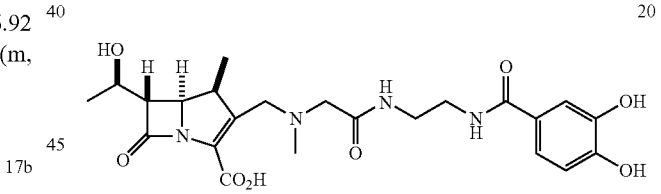

20

¹H NMR (D₂O, 400 MHz): δ 7.27 (s, 1H), 7.24 (dd, J=8.0, 2.4 Hz, 1H), 6.89 (d, J=8.0 Hz, 1H), 4.18-4.10 (m, 1H), 4.00-3.94 (m, 1H), 3.68 (d, J=14.0 Hz, 1H), 3.61-3.38 (m, 4H), 3.31-3.27 (m, 1H), 3.21 (d, J=16.0 Hz, 1H), 3.16-3.02 (m, 3H), 2.25 (s, 3H), 1.23 (d, J=6.0 Hz, 3H), 0.90 (d, J=7.2 Hz, 3H).

Example 19: Synthesis of 21

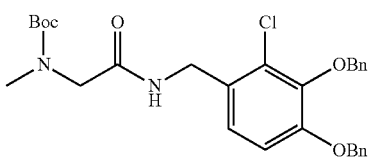

21a

¹H NMR (CDCl₃, 400 MHz): δ 7.48-7.30 (m, 10H), 7.07 (d, J=8.4 Hz, 1H), 6.86 (d, J=8.0 Hz, 1H), 5.12 (s, 2H), 5.04 (s, 2H), 4.49 (d, J=6.0 Hz, 2H), 3.87 (s, 2H), 2.91 (s, 3H), 1.42 (br s, 9H).

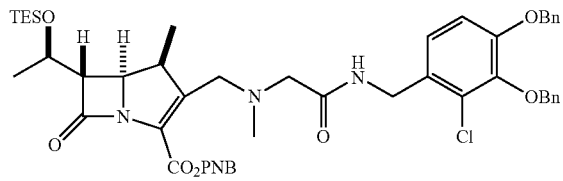

21b

¹H NMR (CDCl₃, 400 MHz): δ 8.20 (d, J=8.0 Hz, 2H), 7.65 (d, J=8.4 Hz, 2H), 7.52-7.30 (m, 11H), 7.10 (d, J=8.8 Hz, 1H), 6.88 (d, J=8.8 Hz, 1H), 5.42 (d, J=13.6 Hz, 1H), 5.20 (d, J=13.6 Hz, 1H), 5.11 (s, 2H), 5.04 (s, 2H), 4.56-4.44 (m, 2H), 4.28-4.22 (m, 1H), 4.20 (dd, J=10.0, 3.2 Hz, 1H), 4.02 (d, J=14.4 Hz, 1H), 3.26-3.18 (m, 2H), 3.11 (d, J=14.4 Hz, 1H), 3.09 (d, J=16.4 Hz, 1H), 2.98 (d, J=16.4 Hz, 1H), 2.22 (s, 3H), 1.22 (d, J=6.4 Hz, 3H), 1.11 (d, J=7.2 Hz, 3H), 0.94 (t, J=8.0 Hz, 9H), 0.59 (q, J=7.6 Hz, 6H).

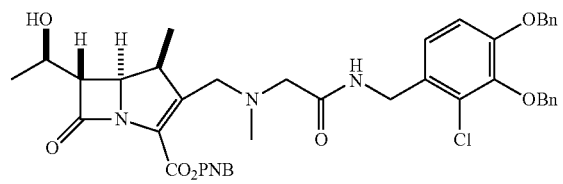

21c

¹H NMR (CDCl₃, 400 MHz): δ 8.21 (d, J=8.4 Hz, 2H), 7.64 (d, J=8.8 Hz, 2H), 7.50-7.30 (m, 11H), 7.12 (d, J=8.4 Hz, 1H), 6.88 (d, J=8.8 Hz, 1H), 5.46 (d, J=13.6 Hz, 1H), 5.19 (d, J=14.0 Hz, 1H), 5.12 (s, 2H), 5.04 (s, 2H), 4.60 (dd, J=14.4, 6.8 Hz, 1H), 4.38 (dd, J=14.0, 5.2 Hz, 1H), 4.10-4.00 (m, 3H), 3.21-3.12 (m, 2H), 3.08-3.02 (m, 2H), 4.92 (d, J=16.8 Hz, 1H), 2.27 (s, 3H), 2.18 (d, J=4.8 Hz, 1H), 1.25 (d, J=6.4 Hz, 3H), 1.05 (d, J=7.2 Hz, 3H).

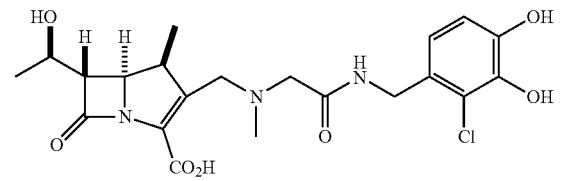

21

¹H NMR (D₂O, 400 MHz): δ 6.80 (d, J=8.0 Hz, 1H), 6.75 (d, J=8.0 Hz, 1H), 4.42 (s, 2H), 4.27-4.18 (m, 1H), 4.08-4.03 (m, 1H), 3.80-3.22 (m, 1H), 3.40-3.06 (m, 5H), 2.35 (s, 3H), 1.27 (d, J=6.0 Hz, 3H), 0.96 (d, J=7.6 Hz, 3H).

Example 20: Synthesis of 22

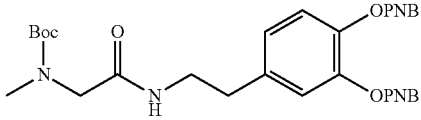

22a

¹H NMR (400 MHz, CDCl₃): δ 8.26-8.21 (m, 4H), 7.64 (d, J=8.4 Hz, 2H), 7.61 (d, J=8.0 Hz, 2H), 6.85 (d, J=8.4 Hz, 1H), 6.81 (d, J=1.6 Hz, 1H), 6.75 (dd, J=8.4, 1.6 Hz, 1H), 5.25 (s, 2H), 5.22 (s, 2H), 3.81 (s, 2H), 3.48 (q, J=6.4 Hz, 2H), 2.85 (s, 3H), 2.74 (t, J=6.8 Hz, 2H), 1.42 (s, 9H).

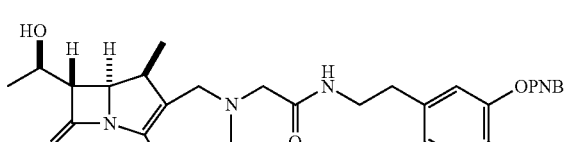

22c

¹H NMR (CDCl₃, 400 MHz): δ 8.30-8.20 (m, 6H), 7.68-7.58 (m, 6H), 6.97 (t, J=5.6 Hz, 1H), 6.88 (d, J=8.4 Hz, 1H), 6.83 (d, J=1.6 Hz, 1H), 6.77 (dd, J=8.0, 1.6 Hz, 1H), 5.47 (d, J=13.6 Hz, 1H), 5.28-5.18 (m, 7H), 4.23-4.15 (m, 1H), 4.11 (dd, J=10.0, 2.8 Hz, 1H), 3.99 (d, J=14.4 Hz, 1H), 3.66-3.41 (m, 2H), 3.23 (dd, J=6.8, 2.8 Hz, 1H), 3.07-2.97 (m, 3H), 2.90 (d, J=16.4 Hz, 1H), 2.82-2.74 (m, 2H), 2.17 (s, 3H), 2.04 (d, J=4.4 Hz, 1H), 1.34 (d, J=6.4 Hz, 3H), 1.08 (d, J=7.2 Hz, 3H).

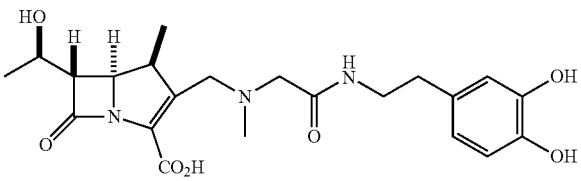

22

¹H NMR (D₂O, 400 MHz): δ 6.86 (d, J=7.6 Hz, 1H), 6.80 (d, J=1.6 Hz, 1H), 6.71 (dd, J=8.0, 1.6 Hz, 1H), 4.24 (p, J=6.0 Hz, 1H), 4.08 (dd, J=10.0, 2.4 Hz, 1H), 3.64 (d, J=14.0 Hz, 1H), 3.60-3.36 (m, 4H), 3.11-2.99 (m, 2H), 2.96-2.86 (m, 2H), 2.77-2.70 (m, 2H), 2.14 (s, 3H), 1.30 (d, J=6.0 Hz, 3H), 0.96 (d, J=7.2 Hz, 3H).

Example 21: Synthesis of 23

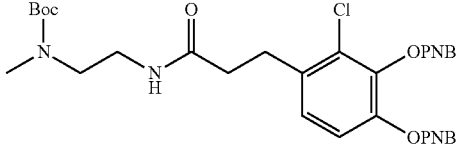

23a

¹H NMR (400 MHz, CDCl₃): δ 8.22 (d, J=7.2 Hz, 4H), 7.66 (d, J=8.4 Hz, 2H), 7.54 (d, J=8.8 Hz, 1H), 7.00 (d, J=8.4 Hz, 1H), 6.79 (d, J=8.8 Hz, 1H), 6.42-6.34 (br, 1H), 5.19 (s, 2H), 5.15 (s, 2H), 3.37 (br s, 4H), 3.03 (t, J=8.0 Hz, 2H), 2.86 (s, 3H), 2.44 (t, J=7.6 Hz, 2H), 1.45 (s, 9H.

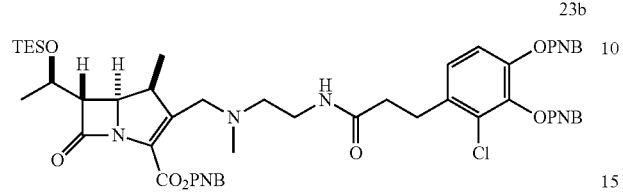

23b

¹H NMR (CDCl₃, 400 MHz): δ 8.23-8.17 (m, 6H), 7.64 (d, J=8.8 Hz, 4H), 7.54 (d, J=8.4 Hz, 2H), 7.01 (d, J=8.8 Hz, 1H), 6.80 (d, J=8.8 Hz, 1H), 5.86 (t, J=5.2 Hz, 1H), 5.43 (d, J=14.0 Hz, 1H), 5.21 (d, J=14.0 Hz, 1H), 5.18 (s, 2H), 5.14 (s, 2H), 4.24 (p, J=6.0 Hz, 1H), 4.20 (dd, J=10.0, 2.8 Hz, 1H), 3.83 (d, J=14.4 Hz, 1H), 3.36-3.20 (m, 2H), 3.11-3.00 (m, 3H), 2.54-2.38 (m, 4H), 2.16 (s, 3H), 1.23 (d, J=5.6 Hz, 3H), 1.14 (d, J=7.6 Hz, 3H), 0.92 (t, J=8.0 Hz, 9H), 0.58 (t, J=8.0 Hz, 6H).

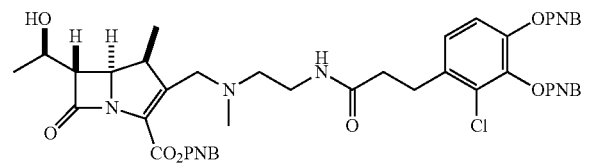

23c

¹H NMR (CDCl₃, 400 MHz): δ 8.25-8.18 (m, 6H), 7.65 (d, J=8.0 Hz, 2H), 7.63 (d, J=8.0 Hz, 2H), 7.54 (d, J=8.8 Hz, 2H), 7.02 (d, J=8.8 Hz, 1H), 6.80 (d, J=8.8 Hz, 1H), 5.86 (t, J=4.8 Hz, 1H), 5.47 (d, J=14.4 Hz, 1H), 5.23-5.16 (m, 3H), 5.15 (s, 2H), 4.28-4.17 (m, 2H), 3.84 (d, J=14.8 Hz, 1H), 3.37-3.23 (m, 4H), 3.12-3.00 (m, 3H), 2.54-2.38 (m, 4H), 2.15 (s, 3H), 1.33 (d, J=6.0 Hz, 3H), 1.14 (d, J=7.2 Hz, 3H).

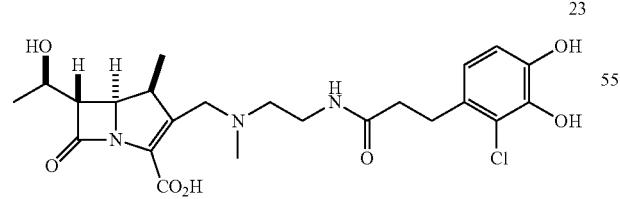

23

¹H NMR (D₂O, 400 MHz): δ 6.73 (d, J=7.6 Hz, 1H), 6.58 (d, J=7.6 Hz, 1H), 4.27-4.16 (m, 2H), 3.80-3.60 (m, 2H), 3.48-3.30 (m, 3H), 3.20-3.08 (m, 1H), 3.00-2.85 (m, 3H), 2.81-2.72 (m, 1H), 2.65-2.50 (m, 5H), 1.29 (d, J=6.4 Hz, 3H), 1.12 (d, J=5.2 Hz, 3H).

Example 22: Synthesis of 24

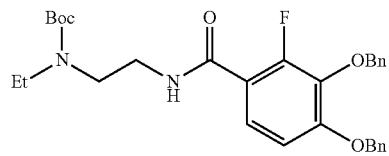

24a

¹H NMR (400 MHz, CDCl₃): δ 7.75 (br, 1H), 7.41-7.29 (comp, 10H), 6.82 (d, J=8.8 Hz, 1H), 5.15 (s, 2H), 5.06 (s, 2H), 3.60-3.56 (m, 2H), 3.42, 3.26 (br, 2H), 1.45 (s, 9H), 1.11, (t, J=7.6 Hz, 3H).

24b

¹H NMR (400 MHz, CDCl₃): δ 8.20 (d, J=9.2 Hz, 2H), 7.80 (t, J=8.4 Hz, 1H), 7.65 (d, J=8.8 Hz, 2H), 7.40-7.28 (comp, 10H), 7.71-7.10 (m, 1H), 6.85 (d, J=8.8 Hz), 5.44 (d, J=14.0 Hz, 1H), 5.22 (d, J=14.0 Hz, 1H), 5.16 (s, 2H), 5.06 (s, 2H), 4.23 (t, J=6.4 Hz, 1H), 4.18 (dd, J=3.2 Hz; 10.0 Hz, 1H), 4.00 (d, J=15.2 Hz, 1H), 3.65-3.62 (m, 1H), 3.46-3.39 (m, 1H), 3.36-3.30 (m, 1H), 3.23-3.18 (m, 2H) 2.79-2.70 (m, 1H), 2.67-2.60 (m, 1H), 2.56-2.49 (m, 1H), 2.44-2.37 (m, 1H), 1.17 (d, J=6.0 Hz, 3H), 1.12 (d, J=7.6 Hz, 3H), 1.04 (t, J=7.2 Hz, 3H) 0.90 (t, J=8.0 Hz, 9H), 0.56 (q, J=8.0 Hz, 6H).

24

¹H NMR (400 MHz, D₂O): δ 8.00 (d, J=4.8 Hz, 1H), 7.01 (t, J=8.4 Hz, 1H), 6.61 (d, J=8.4 Hz, 1H), 3.98 (dd, J=2.8 Hz; 10.0 Hz, 1H), 3.93-3.87 (m, 1H), 3.69 (d, J=15.6 Hz, 1H), 3.55 (d, J=16.0 Hz, 1H), 3.50-3.38 (m, 2H), 3.10 (dd, J=3.2 Hz; 6.8 Hz, 1H), 3.02-2.98 (m, 1H), 2.93-2.74 (comp, 4H), 1.12-1.02 (comp, 9H).

Example 23: Synthesis of 25

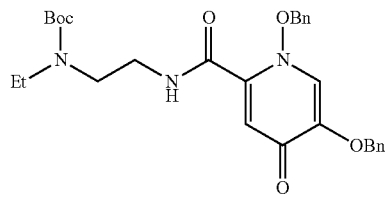
25a $^1$H NMR (400 MHz, DMSO): δ 9.00-8.90 (br, 1H), 8.10-8.04 (br, 1H), 7.50-7.32 (m, 10H), 6.15 (s, 1H), 5.34 (s, 2H), 5.01 (s, 2H), 3.38-3.25 (overlapping with H$_2$O), 2.78 (d, J=8.0 Hz, 3H), 1.39 (s, 9H).

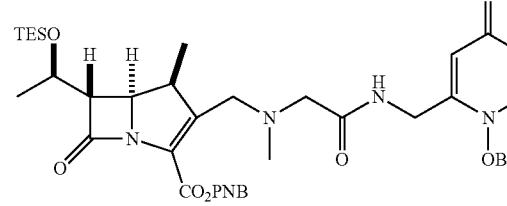
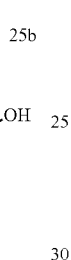
25b $^1$H NMR (CDCl$_3$, 400 MHz): δ 8.22 (d, J=8.8 Hz, 2H), 8.17 (t, J=6.0 Hz, 1H), 8.06 (s, 1H), 7.79 (s, 1H), 7.66 (d, J=8.4 Hz, 2H), 7.44-7.34 (m, 5H), 5.45 (d, J=13.6 Hz, 1H), 5.25-5.19 (m, 3H), 4.29-4.20 (m, 1H), 4.15 (dd, J=10.8, 2.8 Hz, 1H), 3.91 (d, J=14.8 Hz, 1H), 3.60-3.35 (m, 3H), 3.23-3.16 (m, 2H), 2.70-2.60 (m, 1H), 2.56-2.47 (m, 1H), 2.26 (s, 3H), 1.23 (d, J=6.0 Hz, 3H), 1.14 (d, J=8.0 Hz, 3H), 0.93 (t, J=8.0 Hz, 9H), 0.59 (q, J=7.6 Hz, 6H).

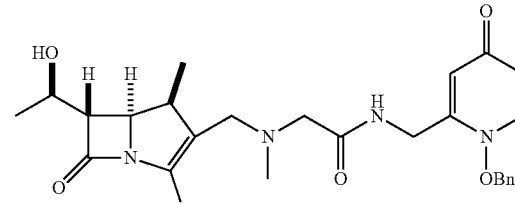
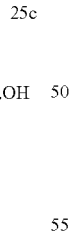
25c $^1$H NMR (CDCl$_3$, 400 MHz): δ 8.22 (d, J=8.0 Hz, 2H), 8.17-8.11 (br, 1H), 8.07-8.02 (br, 1H), 8.79-8.74 (br, 1H), 7.44-7.30 (m, 5H), 5.48 (d, J=14.0 Hz, 1H), 5.24-5.16 (m, 3H), 4.25-4.09 (m, 2H), 3.92 (d, J=14.4 Hz, 1H), 3.60-3.40 (m, 3H), 3.24-3.19 (m, 1H), 3.14 (d, J=14.4 Hz, 1H), 2.68-2.59 (m, 1H), 2.50-2.41 (m, 1H), 2.27 (s, 3H), 1.33 (d, J=6.0 Hz, 3H), 1.11 (d, J=6.8 Hz, 3H).

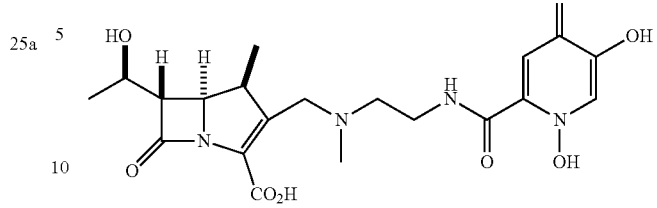
25

$^1$H NMR (D$_2$O, 400 MHz): δ 7.63 (s, 1H), 7.09 (s, 1H), 4.28-4.10 (m, 2H), 3.90-3.65 (m, 4H), 3.48-3.43 (m, 1H), 3.31-3.00 (m, 3H), 2.72 (s, 3H), 1.27 (d, J=6.0 Hz, 3H), 1.14 (d, J=6.0 Hz, 3H).

Example 24: Synthesis of 26

26a $^1$H NMR (400 MHz, CDCl$_3$): δ 7.48-7.23 (m, 11H), 6.95 (s, 1H), 6.20 (s, 1H), 5.02 (s, 2H), 5.01 (s, 2H), 4.28 (d, J=6.0 Hz, 2H), 3.89 (s, 2H), 2.92 (s, 3H), 1.45 (s, 9H).

26b $^1$H NMR (CDCl$_3$, 400 MHz): δ 8.21 (d, J=8.4 Hz, 2H), 7.67 (d, J=8.8 Hz, 2H), 7.50-7.26 (m, 11H), 6.95 (s, 1H), 6.24 (s, 1H), 5.43 (d, J=14.0 Hz, 1H), 5.22 (d, J=14.4 Hz, 1H), 5.02 (s, 4H), 4.39 (dd, J=16.4, 6.4 Hz, 1H), 4.31-4.21 (m, 3H), 3.99 (d, J=14.0 Hz, 1H), 3.26-3.04 (m, 5H), 2.27 (s, 3H), 1.25 (d, J=6.4 Hz, 3H), 1.12 (d, J=7.6 Hz, 3H), 0.94 (t, J=8.0 Hz, 9H), 0.60 (t, J=8.0 Hz, 6H).

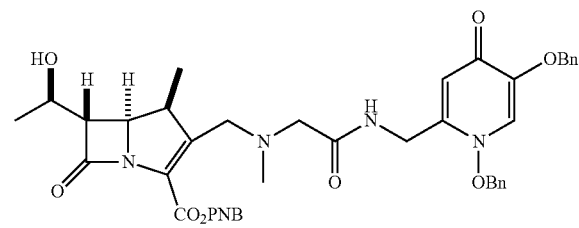
26c

¹H NMR (CDCl₃, 400 MHz): δ 8.21 (d, J=8.8 Hz, 2H), 7.68-7.59 (m, 3H), 7.48-7.24 (m, 10H), 6.99 (s, 1H), 6.07 (s, 1H), 5.46 (d, J=13.6 Hz, 1H), 5.22 (d, J=14.0 Hz, 1H), 5.05 (dd, J=29.2, 11.2 Hz, 2H), 4.99 (dd, J=17.2, 12.4 Hz, 2H), 4.67 (dd, J=16.8, 7.6 Hz, 1H), 4.41 (dd, J=9.6, 2.4 Hz, 1H), 4.29-4.21 (m, 1H), 4.11 (d, J=14.0 Hz, 1H), 4.00 (dd, J=16.8, 4.8 Hz, 1H), 3.35-3.26 (m, 1H), 3.21-3.12 (m, 2H), 3.07 (d, J=17.2 Hz, 1H), 2.38 (s, 3H), 1.38 (d, J=6.4 Hz, 3H), 1.14 (d, J=7.2 Hz, 3H).

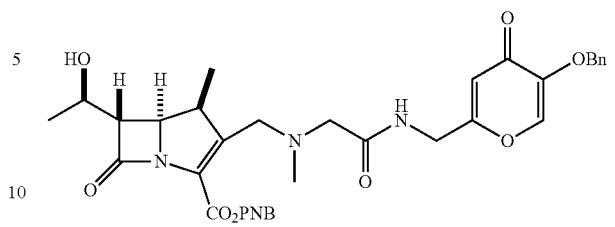

27c

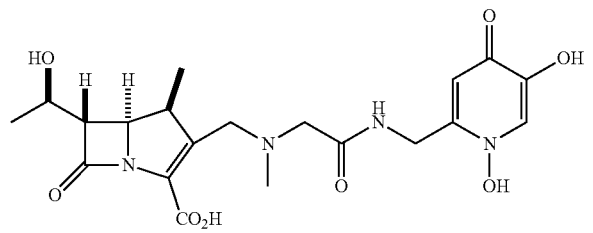

26

¹H NMR (CDCl₃, 400 MHz): δ 8.23 (d, J=8.4 Hz, 2H), 7.66 (d, J=8.4 Hz, 2H), 7.56 (t, J=6.0 Hz, 1H), 7.52 (s, 1H), 7.38-7.30 (m, 5H), 6.25 (s, 1H), 5.48 (d, J=13.6 Hz, 1H), 5.22 (d, J=14.0 Hz, 1H), 5.05 (s, 2H), 4.50 (dd, J=16.4, 6.8 Hz, 1H), 4.30-4.23 (m, 2H), 4.17 (dd, J=16.8, 5.6 Hz, 1H), 4.09 (d, J=14.4 Hz, 1H), 3.32-3.23 (m, 2H), 3.17 (d, J=16.8 Hz, 1H), 3.09 (d, J=14.4 Hz, 1H), 3.00 (d, J=17.2 Hz, 1H), 2.35 (s, 3H), 1.38 (d, J=6.4 Hz, 3H), 1.17 (d, J=7.6 Hz, 3H).

¹H NMR (D₂O, 400 MHz): δ 7.66 (s, 1H), 6.55 (s, 1H), 4.45 (s, 2H), 4.30-3.70 (m, 6H), 3.45 (s, 1H), 3.30-3.18 (m, 1H), 2.75 (s, 3H), 1.27 (s, 3H), 1.11 (s, 3H).

Example 25: Synthesis of 27

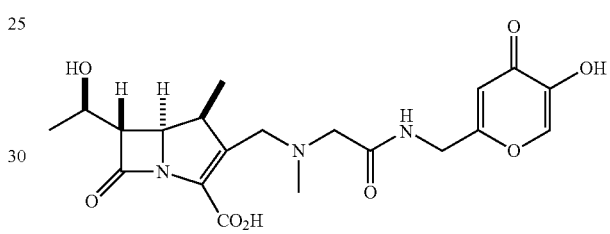

27

¹H NMR (D₂O, 400 MHz): δ 7.94 (s, 1H), 6.44 (s, 1H), 4.35 (s, 2H), 4.26-4.12 (m, 2H), 3.80 (d, J=14.0 Hz, 1H), 3.44-3.18 (m, 5H), 2.37 (s, 3H), 1.29 (d, J=6.4 Hz, 3H), 1.09 (d, J=7.2 Hz, 3H).

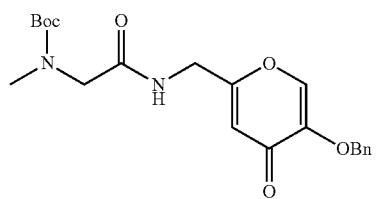

27a

Example 26: Synthesis of 28

¹H NMR (400 MHz, CDCl₃): δ 7.48 (s, 1H), 7.40-7.29 (m, 5H), 6.30 (s, 1H), 5.05 (s, 2H), 4.27 (d, J=5.6 Hz, 2H), 3.89 (s, 2H), 2.95 (s, 3H), 1.46 (s, 9H).

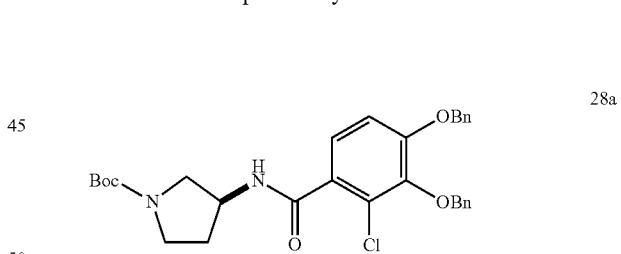

28a

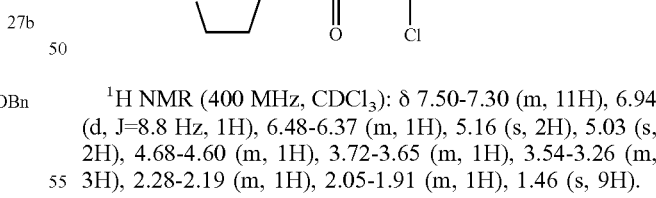

¹H NMR (400 MHz, CDCl₃): δ 7.50-7.30 (m, 11H), 6.94 (d, J=8.8 Hz, 1H), 6.48-6.37 (m, 1H), 5.16 (s, 2H), 5.03 (s, 2H), 4.68-4.60 (m, 1H), 3.72-3.65 (m, 1H), 3.54-3.26 (m, 3H), 2.28-2.19 (m, 1H), 2.05-1.91 (m, 1H), 1.46 (s, 9H).

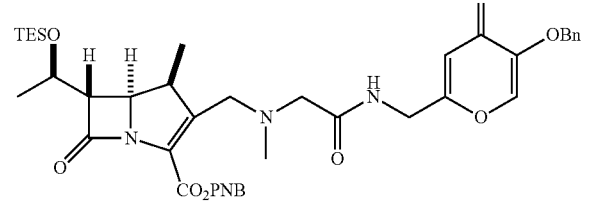

27b

28b

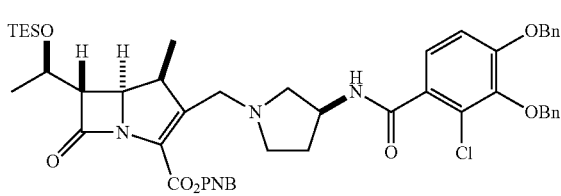

¹H NMR (CDCl₃, 400 MHz): δ 8.20 (d, J=8.4 Hz, 2H), 7.66 (d, J=8.4 Hz, 2H), 7.49 (s, 1H), 7.38-7.30 (m, 5H), 6.32 (s, 1H), 5.43 (d, J=14.4 Hz, 1H), 5.22 (d, J=14.4 Hz, 1H), 5.05 (s, 2H), 4.36 (dd, J=16.8, 6.8 Hz, 1H), 4.31-4.21 (m, 3H), 4.08-3.96 (br, 1H), 3.27-3.04 (m, 5H), 2.30 (s, 3H), 1.24 (d, J=6.0 Hz, 3H), 1.15 (d, J=6.8 Hz, 3H), 0.93 (t, J=8.0 Hz, 9H), 0.59 (t, J=8.0 Hz, 6H).

¹H NMR (CDCl₃, 400 MHz): δ 8.21 (d, J=9.2 Hz, 2H), 7.66 (d, J=8.4 Hz, 2H), 7.48 (d, J=8.8 Hz, 1H), 7.46-7.30 (m, 10H), 6.96 (d, J=8.8 Hz, 1H), 6.59 (d, J=8.4 Hz, 1H), 5.45 (d, J=13.6 Hz, 1H), 5.22 (d, J=14.0 Hz, 1H), 5.16 (s, 2H), 5.03 (s, 2H), 4.64-4.58 (m, 1H), 4.25 (p, J=6.0 Hz, 1H), 4.19 (dd, J=10.0, 3.2 Hz, 1H), 3.88 (d, J=14.4 Hz, 1H), 3.39 (d, J=14.4 Hz, 1H), 3.36-3.26 (m, 1H), 3.23 (dd, J=5.2, 2.8 Hz, 1H), 2.88-2.84 (m, 1H), 2.69 (dd, J=9.2, 2.8 Hz, 1H), 2.63, (dd, J=10.0, 6.0 Hz, 1H), 2.50-2.30 (m, 2H), 1.24 (d, J=6.4 Hz, 3H), 1.18 (d, J=7.6 Hz, 3H), 0.92 (t, J=8.0 Hz, 9H), 0.58 (q, J=8.0 Hz, 6H).

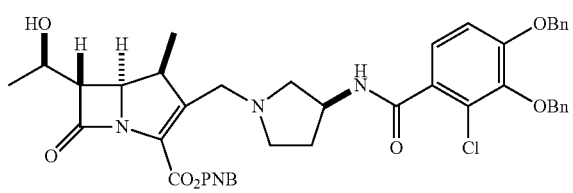

28c

¹H NMR (CDCl₃, 400 MHz): δ 8.23 (d, J=8.8 Hz, 2H), 7.66 (d, J=Hz, 2H), 7.48 (d, J=8.8 Hz, 1H), 7.46-7.30 (m, 10H), 6.96 (d, J=8.8 Hz, 1H), 6.56 (d, J=8.4 Hz, 1H), 5.49 (d, J=14.0 Hz, 1H), 5.22 (d, J=14.0 Hz, 1H), 5.17 (s, 2H), 5.04 (s, 2H), 4.66-4.59 (m, 1H), 4.28-4.21 (m, 1H), 4.19 (dd, J=9.6, 2.4 Hz, 1H), 3.87 (d, J=14.8 Hz, 1H), 3.42-3.32 (m, 2H), 3.27 (dd, J=6.0, 2.8 Hz, 1H), 2.91-2.85 (m, 1H), 2.71-2.66 (m, 1H), 2.61-2.56 (m, 1H), 2.48-2.41 (m, 1H), 2.40-2.30 (m, 1H), 1.78-1.69 (m, 1H), 1.64 (d, J=5.2 Hz, 1H), 1.34 (d, J=6.4 Hz, 3H), 1.18 (d, J=7.2 Hz, 3H).

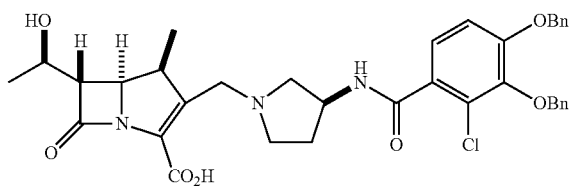

28

¹H NMR (D₂O, 400 MHz): δ 6.77-6.67 (br, 2H), 4.67-4.58 (m, 1H), 4.30-4.20 (br, 2H), 4.08-3.95 (br, 2H), 3.57-3.20 (m, 6H), 2.58-2.47 (br, 1H), 2.16-2.04 (br, 1H), 1.29 (d, J=6.4 Hz, 3H), 1.18 (br s, 3H).

Example 27: Synthesis of 29

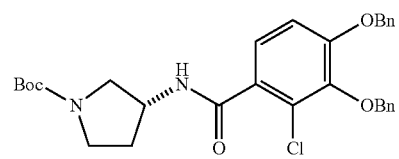

29a

¹H NMR (400 MHz, CDCl₃): δ 7.50-7.30 (m, 11H), 6.94 (d, J=8.4 Hz, 1H), 6.48-6.37 (m, 1H), 5.16 (s, 2H), 5.03 (s, 2H), 4.68-4.60 (m, 1H), 3.71-3.65 (m, 1H), 3.53-3.26 (m, 3H), 2.28-2.18 (m, 1H), 2.05-1.90 (m, 1H), 1.46 (s, 9H).

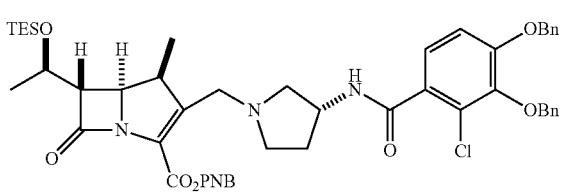

29b

¹H NMR (CDCl₃, 400 MHz): δ 8.21 (d, J=8.4 Hz, 2H), 7.66 (d, J=8.8 Hz, 2H), 7.48 (d, J=8.4 Hz, 1H), 7.46-7.30 (m, 10H), 6.96 (d, J=8.4 Hz, 1H), 6.62 (d, J=8.0 Hz, 1H), 5.44 (d, J=14.0 Hz, 1H), 5.21 (d, J=14.0 Hz, 1H), 5.17 (s, 2H), 5.03 (s, 2H), 4.66-4.59 (m, 1H), 4.26 (p, J=6.0 Hz, 1H), 4.21 (dd, J=10.0, 2.4 Hz, 1H), 3.89 (d, J=14.8 Hz, 1H), 3.40-3.31 (m, 2H), 3.23 (dd, J=5.2, 3.2 Hz, 1H), 2.87-2.80 (m, 2H), 2.64-2.59 (m, 1H), 2.40-2.32 (m, 2H), 1.26 (d, J=6.4 Hz, 3H), 1.17 (d, J=7.6 Hz, 3H), 0.94 (t, J=8.0 Hz, 9H), 0.60 (q, J=8.0 Hz, 6H).

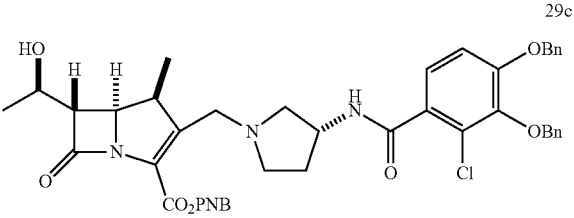

29c

¹H NMR (CDCl₃, 400 MHz): δ 8.22 (d, J=9.2 Hz, 2H), 7.65 (d, J=8.8 Hz, 2H), 7.48 (d, J=8.4 Hz, 1H), 7.46-7.31 (m, 10H), 6.96 (d, J=8.8 Hz, 1H), 6.62 (d, J=8.4 Hz, 1H), 5.48 (d, J=13.6 Hz, 1H), 5.22 (d, J=13.2 Hz, 1H), 5.17 (s, 2H), 5.03 (s, 2H), 4.67-4.59 (m, 1H), 4.30-4.20 (m, 2H), 3.89 (d, J=14.4 Hz, 1H), 3.44-3.35 (m, 2H), 3.28 (dd, J=6.4, 3.2 Hz, 1H), 2.87-2.77 (m, 2H), 2.68-2.62 (m, 1H), 2.39-2.30 (m, 2H), 1.79-1.66 (m, 2H), 1.35 (d, J=6.4 Hz, 3H), 1.19 (d, J=Hz, 3H).

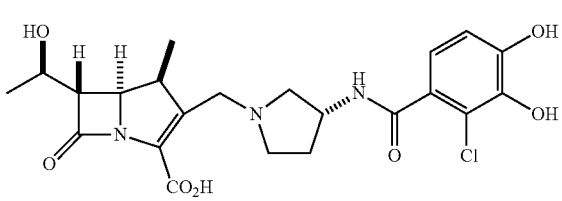

29

¹H NMR (D₂O, 400 MHz): δ 6.80-6.68 (br, 2H), 4.69-4.61 (m, 1H), 4.30-4.20 (br, 2H), 4.12-3.95 (br, 2H), 3.72-3.20 (m, 6H), 2.60-2.48 (br, 1H), 2.23-2.04 (br, 1H), 1.29 (d, J=5.2 Hz, 3H), 1.18 (br s, 3H).

Example 28: Synthesis of 34

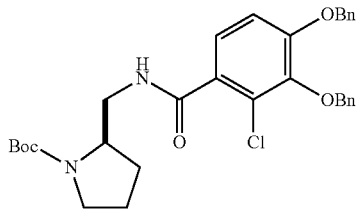
34a

¹H NMR (400 MHz, CDCl₃): δ 7.48-7.30 (m, 11H), 6.89 (d, J=8.4 Hz, 1H), 5.14 (s, 2H), 5.02 (s, 2H), 4.14-4.05 (m, 1H), 3.66-3.31 (m, 4H), 2.09-1.72 (m, 4H), 1.43 (s, 9H).

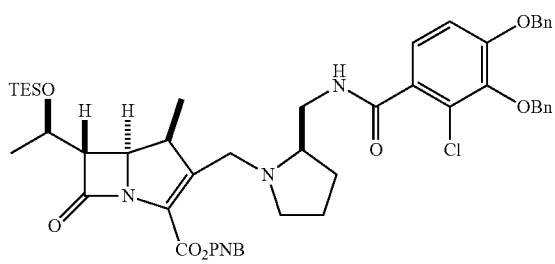
34b

¹H NMR (CDCl₃, 400 MHz): δ 8.07 (d, J=8.8 Hz, 2H), 7.56 (d, J=9.2 Hz, 2H), 7.46-7.30 (m, 11H), 7.12-7.08 (m, 1H), 6.95 (d, J=8.4 Hz, 1H), 5.23 (d, J=14.0 Hz, 1H), 5.13 (s, 2H), 5.06-4.95 (m, 3H), 4.23 (p, J=6.0 Hz, 1H), 4.20-4.14 (m, 2H), 3.87-3.80 (m, 1H), 3.38-3.31 (m, 1H), 3.21 (dd, J=5.6, 3.2 Hz, 1H), 3.15-3.03 (m, 2H), 2.89 (d, J=12.4 Hz, 1H), 2.69-2.62 (m, 1H), 2.34-2.26 (m, 1H), 1.99-1.87 (m, 1H), 1.78-1.67 (m, 3H), 1.23 (d, J=6.0 Hz, 3H), 1.14 (d, J=7.6 Hz, 3H), 0.92 (t, J=8.0 Hz, 9H), 0.57 (q, J=8.0 Hz, 6H).

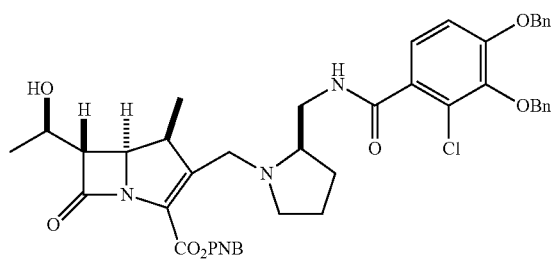
34c

¹H NMR (CDCl₃, 400 MHz): δ 8.10 (d, J=8.4 Hz, 2H), 7.56 (d, J=8.8 Hz, 2H), 7.46-7.30 (m, 11H), 7.04-6.99 (m, 1H), 6.95 (d, J=8.4 Hz, 1H), 5.29 (d, J=14.0 Hz, 1H), 5.13 (s, 2H), 5.06-4.99 (m, 3H), 4.24-4.12 (m, 3H), 3.80-3.73 (m, 1H), 3.37-3.30 (m, 1H), 3.24-3.14 (m, 2H), 3.09-3.02 (m, 1H), 2.93 (d, J=12.8 Hz, 1H), 2.73-2.65 (m, 1H), 2.38-2.30 (m, 1H), 1.99-1.87 (m, 1H), 1.79 (d, J=5.2 Hz, 1H), 1.78-1.67 (m, 3H), 1.32 (d, J=6.0 Hz, 3H), 1.14 (d, J=6.8 Hz, 3H).

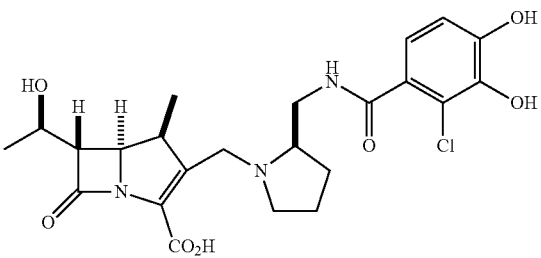
34

¹H NMR (D₂O, 400 MHz): δ 6.74 (d, J=7.6 Hz, 3H), 6.70 (d, J=7.6 Hz, 3H), 4.42-4.13 (m, 3H), 3.85-3.45 (m, 6H), 3.33-3.20 (m, 2H), 2.36-2.23 (br, 1H), 2.15-1.98 (br, 2H), 1.97-1.85 (br, 1H), 1.26 (d, J=6.0 Hz, 3H), 1.16 (d, J=6.4 Hz, 3H).

Example 29: Synthesis of 35

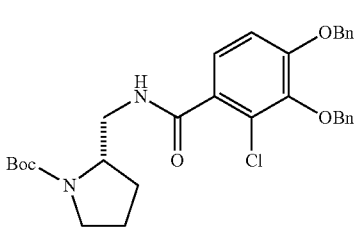
35a

¹H NMR (400 MHz, CDCl₃): δ 7.48-7.30 (m, 11H), 6.89 (d, J=8.0 Hz, 1H), 5.14 (s, 2H), 5.02 (s, 2H), 4.13-4.05 (m, 1H), 3.65-3.30 (m, 4H), 2.09-1.72 (m, 4H), 1.43 (s, 9H).

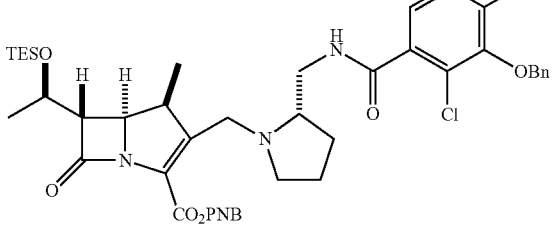
35b

¹H NMR (CDCl₃, 400 MHz): δ 8.21 (d, J=8.8 Hz, 2H), 7.66 (d, J=8.8 Hz, 2H), 7.56 (d, J=8.8 Hz, 1H), 7.46-7.30 (m, 10H), 6.97 (d, J=9.2 Hz, 1H), 6.90-6.86 (m, 1H), 5.44 (d, J=14.0 Hz, 1H), 5.21 (d, J=14.4 Hz, 1H), 5.17 (s, 2H), 5.04 (dd, J=14.4, 10.8 Hz, 2H), 4.25 (p, J=6.0 Hz, 1H), 4.19 (dd, J=10.0, 3.2 Hz, 1H), 3.89 (d, J=14.8 Hz, 1H), 3.86-3.79 (m, 1H), 3.39 (d, J=14.4 Hz, 1H), 3.37-3.26 (m, 1H), 3.21 (dd, J=5.6, 3.2 Hz, 1H), 3.00-2.94 (m, 1H), 2.79-2.72 (m, 1H), 2.20-2.13 (m, 1H), 2.02-1.92 (m, 1H), 1.78-1.67 (m, 3H), 1.23 (d, J=5.6 Hz, 3H), 1.07 (d, J=6.8 Hz, 3H), 0.92 (t, J=8.0 Hz, 9H), 0.58 (q, J=8.0 Hz, 6H).

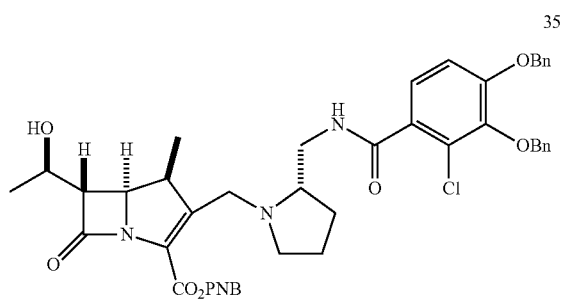

35c

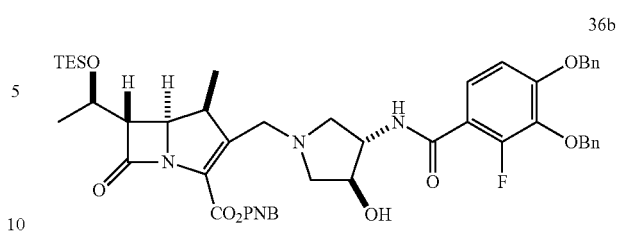

36b

¹H NMR (400 MHz, CDCl₃): δ 8.21 (d, J=8.8 Hz, 2H), 7.76 (app t, J=8.8 Hz, 1H), 7.66 (d, J=8.8 Hz, 2H), 7.40-7.30 (comp, 10H), 6.92-6.85 (comp, 2H), 5.46 (d, J=14.0 Hz, 1H), 5.22 (d, J=13.6 Hz, 1H), 5.17 (s, 2H), 5.07 (s, 2H), 4.26-4.20 (comp, 4H), 3.93 (d, J=14.4 Hz, 1H), 3.69 (br, 1H) 3.37-3.32 (comp, 2H), 3.24 (dd, J=2.8 Hz, 5.2 Hz, 1H), 3.14 (dd, J=7.6 Hz, 9.2 Hz, 1H), 3.04 (dd, J=6.0 Hz, 9.6 Hz, 1H), 2.57 (dd, J=4.8 Hz, 10.8 Hz, 1H) 2.51 (dd, J=5.6 Hz, 9.2 Hz, 1H) 1.25 (d, J=6.0 Hz, 3H), 1.19 (d, J=7.6 Hz, 3H), 0.94 (t, J=8.0 Hz, 9H), 0.59 (q, J=8.0 Hz, 6H).

¹H NMR (CDCl₃, 400 MHz): δ 8.21 (d, J=8.8 Hz, 2H), 7.65 (d, J=8.4 Hz, 2H), 7.55 (d, J=8.8 Hz, 1H), 7.46-7.30 (m, 10H), 6.97 (d, J=9.2 Hz, 1H), 6.86 (d, J=9.2 Hz, 1H), 5.47 (d, J=13.6 Hz, 1H), 5.21 (d, J=14.0 Hz, 1H), 5.17 (s, 2H), 5.04 (dd, J=13.2, 10.8 Hz, 2H), 4.27-4.16 (m, 2H), 3.89 (d, J=14.8 Hz, 1H), 3.81 (ddd, J=14.0, 7.6, 2.4 Hz, 1H), 3.42-3.29 (m, 3H), 3.24 (dd, J=6.0, 2.8 Hz, 1H), 2.95 (t, J=6.4 Hz, 1H), 2.78-2.72 (br, 1H), 2.16 (q, J=8.4 Hz, 1H), 2.02-1.92 (m, 1H), 1.85 (d, J=4.4 Hz, 1H), 1.78-1.65 (m, 3H), 1.33 (d, J=6.0 Hz, 3H), 1.07 (d, J=7.2 Hz, 3H).

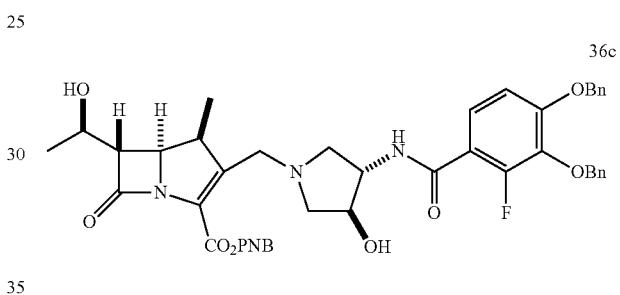

36c

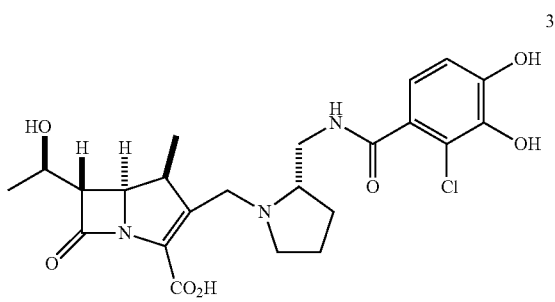

35

¹H NMR (400 MHz, CDCl₃): δ 8.21 (d, J=9.2 Hz, 2H), 7.75 (app t, J=8.8 Hz, 1H), 7.65 (d, J=8.4 Hz, 2H), 7.40-7.30 (comp, 10H), 6.95-6.84 (comp, 2H), 5.48 (d, J=13.6 Hz, 1H), 5.21 (d, J=14.0 Hz, 1H), 5.16 (s, 2H), 5.07 (s, 2H), 4.26-4.18 (comp, 4H), 3.93 (d, J=14.0 Hz, 1H), 3.39-3.34 (comp, 2H), 3.28 (dd, J=3.2 Hz, 6.4 Hz, 1H), 3.16-3.05 (comp, 2H), 2.58-2.51 (comp, 2H), 1.34 (d, J=6.0 Hz, 3H), 1.20 (d, J=7.6 Hz, 3H).

¹H NMR (D₂O, 400 MHz): δ 6.78-6.68 (m, 2H), 4.28-3.98 (m, 4H), 3.80-3.45 (m, 5H), 3.33-3.20 (br, 1H), 2.96-2.85 (br, 1H), 2.39-2.20 (br, 1H), 2.13-1.84 (br, 3H), 1.29 (d, J=6.8 Hz, 3H), 1.18 (d, J=6.0 Hz, 3H).

Example 30: Synthesis of 36

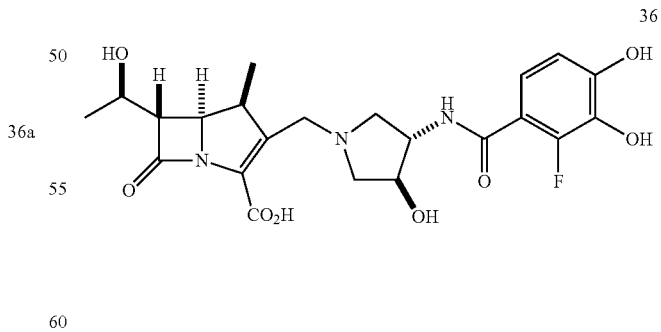

36

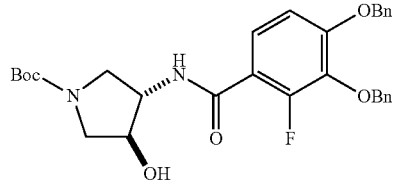

36a

¹H NMR (400 MHz, CD₃OD): δ 7.74 (app t, J=8.8 Hz, 1H), 7.42-7.31 (comp, 10H), 6.85 (d, J=9.2 Hz, 1H), 6.71 (br, 1H), 5.17 (s, 2H), 5.08 (s, 2H), 4.40-4.30 (comp, 2H), 3.90-3.80 (m, 1H), 3.80-3.71 (m, 1H), 3.40-3.31 (comp, 2H), 1.48 (s, 9H).

¹H NMR (400 MHz, D₂O): δ 8.18 (br, 1H), 6.93 (app t, J=8.4 Hz, 1H), 6.62 (d, J=8.8 Hz, 1H), 4.20 (br, 2H), 4.00 (dd, J=2.4 Hz, 10.0 Hz, 1H) 3.93 (t, J=6.0 Hz, 1H) 3.85-3.75 (m, 1H), 3.56 (d, J=15.6 Hz, 1H), 3.40-3.30 (m, 2H), 3.18-3.12 (m, 2H), 3.05-3.00 (m, 1H), 2.85-2.78 (m, 2H), 1.12 (d, J=6.0 Hz, 3H), 1.06 (d, J=6.0 Hz, 3H).

Example 31: Synthesis of 37

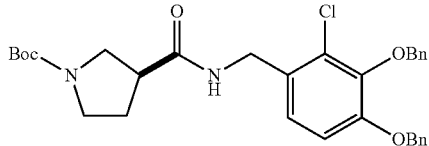
37a $^1$H NMR (400 MHz, CDCl$_3$): δ 7.48-7.30 (m, 10H), 7.06 (d, J=8.4 Hz, 1H), 6.87 (d, J=8.4 Hz, 1H), 5.95-5.88 (br, 1H), 5.12 (s, 2H), 5.06 (s, 2H), 4.47 (d, J=6.4 Hz, 2H), 3.66-3.50 (m, 3H), 3.47 (dd, J=11.2, 7.6 Hz, 1H), 3.35-3.27 (m, 1H), 2.87-2.78 (m, 1H), 2.20-203 (m, 2H), 1.45 (s, 9H).

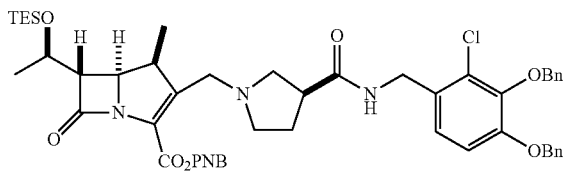
37b $^1$H NMR (CDCl$_3$, 400 MHz): δ 8.20 (d, J=8.4 Hz, 2H), 7.64 (d, J=8.8 Hz, 2H), 7.47-7.29 (m, 10H), 7.06 (d, J=8.4 Hz, 1H), 6.97 (t, J=5.6 Hz, 1H), 6.87 (d, J=8.4 Hz, 1H), 5.41 (d, J=13.6 Hz, 1H), 5.17 (d, J=13.6 Hz, 1H), 5.11 (s, 2H), 5.04 (s, 2H), 4.50 (dd, J=14.4, 6.4 Hz, 1H), 4.33 (dd, J=14.8, 6.0 Hz, 1H), 4.27-4.20 (m, 1H), 4.17 (dd, J=10.4, 3.2 Hz, 1H), 3.90 (d, J=14.4 Hz, 1H), 3.32 (d, J=14.0 Hz, 1H), 3.23-3.17 (m, 2H), 2.95-2.80 (m, 3H), 2.46-2.36 (m, 2H), 2.20-2.08 (m, 1H), 2.00-1.90 (m, 1H), 1.22 (d, J=5.6 Hz, 3H), 1.08 (d, J=7.2 Hz, 3H), 0.94 (t, J=8.0 Hz, 9H), 0.59 (q, J=8.0 Hz, 6H).

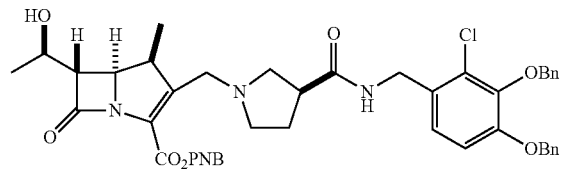
37c $^1$H NMR (CDCl$_3$, 400 MHz): δ 8.21 (d, J=8.8 Hz, 2H), 7.63 (d, J=9.2 Hz, 2H), 7.48-7.32 (m, 10H), 7.11 (d, J=8.4 Hz, 1H), 7.00-6.96 (m, 1H), 6.88 (d, J=8.8 Hz, 1H), 5.45 (d, J=13.6 Hz, 1H), 5.19-5.13 (m, 3H), 5.02 (s, 2H), 4.69 (dd, J=14.0, 7.2 Hz, 1H), 4.16 (dd, J=14.0, 3.2 Hz, 1H), 3.96 (dd, J=11.2, 3.6 Hz, 1H), 3.88-3.80 (m, 2H), 3.26 (d, J=14.4 Hz, 1H), 3.12 (dd, J=8.0, 3.2 Hz, 1H), 3.04-2.97 (m, 1H), 2.92-2.80 (m, 3H), 2.64-2.62 (m, 1H), 2.37-2.28 (m, 1H), 2.25-2.11 (m, 2H), 2.00-1.91 (m, 1H), 1.20 (d, J=6.0 Hz, 3H), 0.86 (d, J=7.2 Hz, 3H).

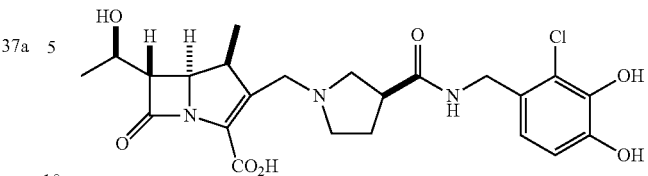
37

$^1$H NMR (D$_2$O, 400 MHz): δ 6.78 (d, J=8.0 Hz, 1H), 6.70 (d, J=8.0 Hz, 1H), 4.35 (dd, J=21.6, 14.8 Hz, 2H), 4.27-4.20 (m, 2H), 4.03 (s, 2H), 3.50-3.17 (m, 7H), 2.44-2.30 (m, 1H), 2.25-2.12 (m, 1H), 1.29 (d, J=6.8 Hz, 3H), 1.16 (d, J=7.6 Hz, 3H).

Example 32: Synthesis of 38

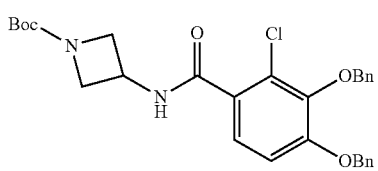
38a $^1$H NMR (400 MHz, CDCl$_3$): δ 7.50 (d, J=8.8 Hz, 1H), 7.47-7.30 (m, 10H), 6.96 (d, J=8.8 Hz, 1H), 6.76 (d, J=8.4 Hz, 1H), 5.17 (s, 2H), 5.04 (s, 2H), 4.89-4.75 (m, 1H), 4.33 (dd, J=9.6, 7.2 Hz, 2H), 3.84 (dd, J=9.6, 5.2 Hz, 1H), 1.45 (s, 9H).

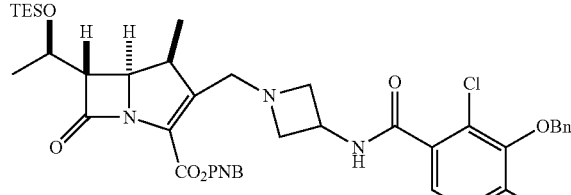
38b $^1$H NMR (CDCl$_3$, 400 MHz): δ 8.22 (d, J=8.8 Hz, 2H), 7.67 (d, J=9.2 Hz, 2H), 7.48-7.30 (m, 11H), 6.95 (d, J=8.4 Hz, 1H), 6.64 (d, J=8.0 Hz, 1H), 5.46 (d, J=13.6 Hz, 1H), 5.23 (d, J=14.0 Hz, 1H), 5.17 (s, 2H), 5.05 (s, 2H), 4.77-4.68 (m, 1H), 4.25 (p, J=6.0 Hz, 1H), 4.18 (dd, J=10.8, 3.6 Hz, 1H), 3.87 (d, J=14.0 Hz, 1H), 3.78-3.70 (m, 2H), 3.32-3.21 (m, 3H), 3.10 (t, J=6.0 Hz, 1H), 3.00 (t, J=6.8 Hz, 1H), 1.27 (d, J=6.0 Hz, 3H), 1.17 (d, J=7.6 Hz, 3H), 0.95 (t, J=8.0 Hz, 9H), 0.60 (q, J=8.0 Hz, 6H).

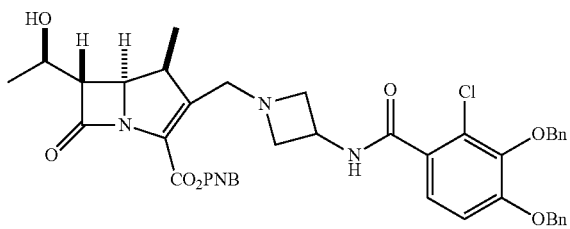

38c

¹H NMR (CDCl₃, 400 MHz): δ 8.23 (d, J=8.8 Hz, 2H), 7.67 (d, J=8.4 Hz, 2H), 7.48-7.30 (m, 11H), 6.95 (d, J=8.8 Hz, 1H), 6.66 (d, J=7.6 Hz, 1H), 5.50 (d, J=13.6 Hz, 1H), 5.22 (d, J=13.6 Hz, 1H), 5.17 (s, 2H), 5.04 (s, 2H), 4.76-4.66 (m, 1H), 4.27 (p, J=6.0 Hz, 1H), 4.20 (dd, J=10.4, 2.8 Hz, 1H), 3.86 (d, J=14.8 Hz, 1H), 3.76-3.68 (m, 2H), 3.36-3.25 (m, 3H), 3.09 (t, J=6.4 Hz, 1H), 3.01 (t, J=6.0 Hz, 1H), 1.36 (d, J=6.0 Hz, 3H), 1.18 (d, J 7.6 Hz, 3H).

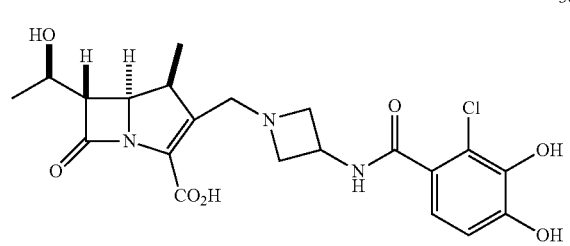

38

¹H NMR (D₂O, 400 MHz): δ 6.88-6.72 (br, 2H), 4.40-3.70 (m, 8H), 3.48-3.43 (m, 1H), 3.28-3.10 (br, 1H), 1.29 (d, J=5.6 Hz, 3H), 1.16 (br s, 3H).

Example 33: Synthesis of 39

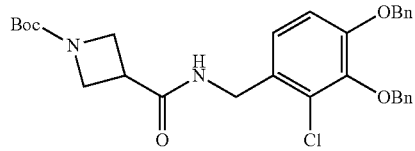

39a

¹H NMR (400 MHz, CDCl₃): δ 7.48-7.30 (m, 10H), 7.09 (d, J=8.8 Hz, 1H), 6.87 (d, J=8.0 Hz, 1H), 5.86 (t, J=6.0 Hz, 1H), 5.12 (s, 2H), 5.06 (s, 2H), 4.49 (d, J=5.6 Hz, 2H), 4.12-4.00 (m, 4H), 3.19-3.11 (m, 1H), 1.43 (s, 9H).

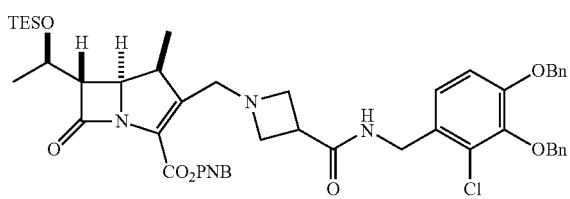

39b

¹H NMR (CDCl₃, 400 MHz): δ 8.21 (d, J=8.4 Hz, 2H), 7.66 (d, J=8.4 Hz, 2H), 7.47-7.29 (m, 10H), 7.10 (d, J=8.4 Hz, 1H), 6.87 (d, J=8.4 Hz, 1H), 6.54 (t, J=6.0 Hz, 1H), 5.44 (d, J=13.6 Hz, 1H), 5.21 (d, J=14.0 Hz, 1H), 5.12 (s, 2H), 5.05 (s, 2H), 4.48 (d, J=6.0 Hz, 2H), 4.23 (p, J=6.0 Hz, 1H), 4.17 (dd, J=11.2, 3.6 Hz, 1H), 3.96 (d, J=14.0 Hz, 1H), 3.47-3.30 (m, 4H), 3.25-3.16 (m, 3H), 3.05 (p, J=6.8 Hz, 1H), 1.23 (d, J=6.0 Hz, 3H), 1.12 (d, J=7.2 Hz, 3H), 0.93 (t, J=8.0 Hz, 9H), 0.59 (q, J=8.0 Hz, 6H).

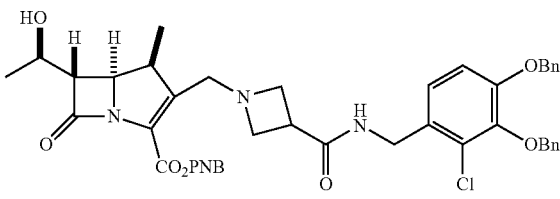

39c

¹H NMR (CDCl₃, 400 MHz): δ 8.22 (d, J=8.8 Hz, 2H), 7.65 (d, J=8.4 Hz, 2H), 7.48-7.31 (m, 10H), 7.11 (d, J=8.0 Hz, 1H), 6.88 (d, J=8.8 Hz, 1H), 6.83 (t, J=5.2 Hz, 1H), 5.48 (d, J=13.6 Hz, 1H), 5.21 (d, J=13.6 Hz, 1H), 5.13 (s, 2H), 5.04 (s, 2H), 4.54 (dd, J=14.0, 5.6 Hz, 1H), 4.43 (dd, J=14.4, 4.8 Hz, 1H), 4.15-4.08 (m, 2H), 3.95 (d, J=14.0 Hz, 1H), 3.45-3.31 (m, 4H), 3.22-3.12 (m, 3H), 3.04-2.95 (m, 1H), 1.29 (d, J=6.4 Hz, 3H), 1.05 (d, J=7.6 Hz, 3H).

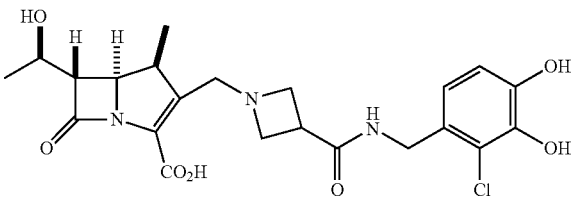

39

¹H NMR (D₂O, 400 MHz): δ 6.76 (d, J=7.6 Hz, 1H), 6.66 (d, J=8.0 Hz, 1H), 4.38 (s, 2H), 4.28-4.00 (m, 5H), 3.91-3.75 (m, 5H), 3.65-3.42 (m, 2H), 3.20-3.10 (m, 1H), 1.28 (d, J=6.4 Hz, 3H), 1.13 (d, J=5.6 Hz, 3H).

Example 34: Synthesis of 41

SCHEME 3.

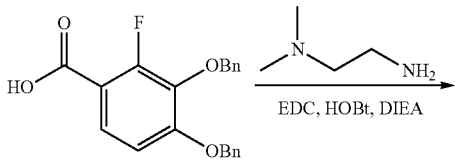

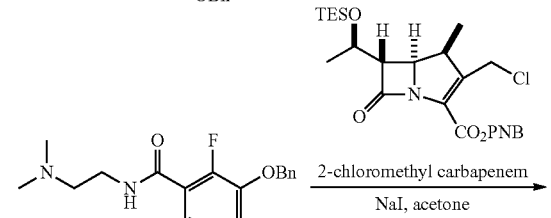

41a

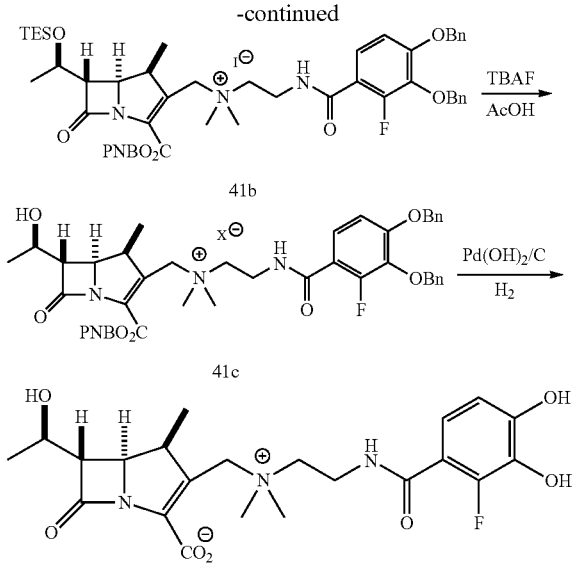

Into a mixture of 3,4-bis(benzyloxy)-2-fluorobenzoic acid (1.76 g, 5.0 mmol) in CH$_2$Cl$_2$ (25 mL) were added HOBt.xH$_2$O (1.11 g, 7.0 mmol), DIEA (1.74 mL, 10.0 mmol), N,N-dimethylethylene diamine (655 μL, 6.0 mmol) and EDC·HCl (1.34 g, 7.0 mmol) at r.t. After stirring overnight, the reaction mixture was diluted with EtOAc (125 mL) and washed with half sat. NaHCO$_3$ (50 mL) and brine. The organic phase was dried over MgSO$_4$ and concentrated in vacuo. The crude was purified on a silica gel column (CH$_2$Cl$_2$/MeOH=98/2 to 90/10) to afford 41a (1.44 g, 68%) as an off-white solid.

$^1$H NMR (CDCl$_3$, 400 MHz): δ 7.76 (app t, J=8.8 Hz, 1H), 7.44-7.29 (m, 10H), 7.17-7.10 (m, 1H), 6.83 (dd, J=8.8, 1.2 Hz, 1H), 5.16 (s, 2H), 5.09 (s, 2H), 3.53 (q, J=6.0 Hz, 2H), 2.50 (t, J=6.0 Hz, 2H), 2.27 (s, 6H).

Step 2

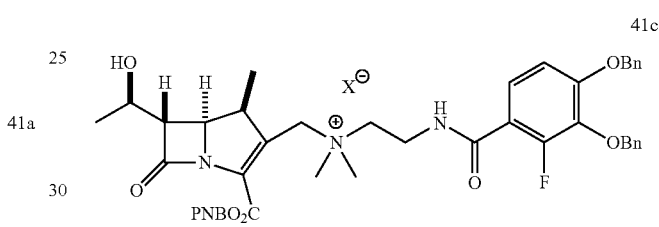

Into a mixture of 2-chloromethyl carbapenem (1.6 g, 3.1 mmol) and 41a (1.56 g, 3.7 mmol) in acetone (15 mL) was added NaI (930 mg, 6.2 mmol) at r.t. After stirring for 2 h, the resulting mixture was concentrated and purified on a silica gel column (CH$_2$Cl$_2$/MeOH=98/2 to 97/3) to afford 41b (1.90 g, 60%) as a yellow foam. {Note: 2-chloromethyl carbapenem [$^1$H NMR (CDCl$_3$, 400 MHz): δ 8.23 (d, J=8.8 Hz, 2H), 7.66 (d, J=8.4 Hz, 2H), 5.46 (d, J=14.0 Hz, 1H), 5.26 (d, J=13.6 Hz, 1H), 5.15 (d, J=12.4 Hz, 1H), 4.31-4.23 (m, 2H), 4.14 (d, J=12.8 Hz, 1H), 3.49-3.39 (m, 1H), 3.29 (dd, J=5.6, 3.6 Hz, 1H), 1.26 (d, J=6.4 Hz, 3H), 1.20 (d, J=7.6 Hz, 3H), 0.947 (t, J=8.0 Hz, 9H), 0.60 (q, J=6.0 Hz, 6H)] was prepared from 2-hydroxymethyl carbapenem by treating with triphosgene (0.5 equiv.) and 2,6-lutidine (4.0 equiv.) in CH$_2$Cl$_2$.}

$^1$H NMR (CD$_3$OD, 400 MHz): δ 8.19 (d, J=9.2 Hz, 2H), 7.76 (d, J=8.8 Hz, 2H), 7.53 (app t, J=8.4 Hz, 1H), 7.50-7.26 (m, 10H), 7.04 (dd, J=8.8, 1.6 Hz, 1H), 5.48 (d, J=14.0 Hz, 1H), 5.40 (d, J=14.0 Hz, 1H), 5.22 (s, 2H), 5.19 (d, J=13.6 Hz, 1H), 5.07 (s, 2H), 4.54 (dd, J=10.0, 3.2 Hz, 1H), 4.41-4.36 (m, 1H), 4.08 (d, J=13.2 Hz, 1H), 3.91-3.85 (m, 2H), 3.67-3.58 (m, 2H), 3.55-3.48 (m, 2H), 3.27 (s, 3H), 3.21 (s, 3H), 1.25 (d, J=6.0 Hz, 3H), 1.24 (d, J=7.2 Hz, 3H), 0.95 (t, J=8.0 Hz, 9H), 0.62 (q, J=8.0 Hz, 6H).

Step 3

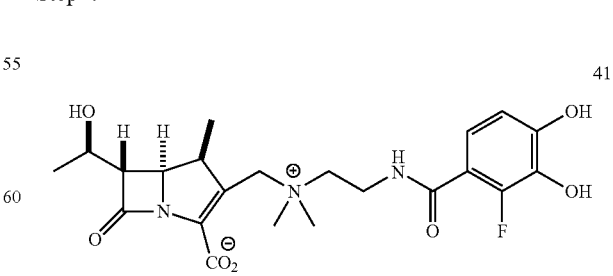

Into a solution of 41b (1.38 g, 1.35 mmol) in THF (40 mL) were added AcOH (155 mL, 2.70 mmol) and TBAF (1.0 M in THF) (4.05 mL, 4.05 mmol), respectively, at 0° C. After stirring for 2.5 h at 0° C. and then 0.5 h at r.t., the reaction solution was quenched with 0.25M SPB (pH 7.0, 150 mL) and extracted with EtOAc (450 mL) (note: due to the formation of emulsion, a small amount of brine was added). The organic phase was dried over MgSO$_4$ and concentrated in vacuo. The crude was purified on a silica gel column (CH$_2$Cl$_2$/MeOH=95/5 to 75/25) to afford 41c (780 mg) as an off-white foam.

$^1$H NMR (CD$_3$OD, 400 MHz): δ 8.17 (d, J=8.4 Hz, 2H), 7.73 (d, J=8.8 Hz, 2H), 7.51 (app t, J=8.8 Hz, 1H), 7.48-7.25 (m, 10H), 7.03 (d, J=9.2 Hz, 1H), 5.49 (d, J=13.6 Hz, 1H), 5.38 (d, J=13.6 Hz, 1H), 5.20 (s, 2H), 5.15 (d, J=13.2 Hz, 1H), 5.06 (s, 2H), 4.44 (dd, J=9.6, 3.2 Hz, 1H), 4.20-4.08 (m, 2H), 3.91-3.85 (m, 2H), 3.71-3.59 (m, 2H), 3.58-3.48 (m, 1H), 3.45 (dd, J=6.0, 2.8 Hz, 1H), 3.27 (s, 3H), 3.21 (s, 3H), 1.30 (d, J=6.0 Hz, 3H), 1.24 (d, J=7.2 Hz, 3H).

Step 4

Into a mixture of 41c (227 mg) in THF (10 mL), DI water (10 mL), and IPA (5 mL) was added Pd(OH)$_2$/C (20 wt %, 53 mg) at 0° C. After stirring for 2 h at 0° C. under H$_2$, the reaction mixture was diluted with DI water and EtOAc (10 mL each) and then filtered through Celite. The filter cake was washed with DI water and EtOAc repeatedly (20 mL each). After the phase separation, the aqueous phase was lyophilized. The crude material was purified on a resin column (SP-207) to afford 41 as a white fluffy solid.

$^1$H NMR (400 MHz, DMSO-d6): δ 8.27-8.21 (m, 1H), 7.03 (app t, J=8.4 Hz, 1H), 6.66 (d, J=8.0 Hz, 1H), 5.28 (d, J=12.0 Hz, 1H), 4.10 (dd, J=9.6, 2.0 Hz, 1H), 3.97-3.89 (m, 1H), 3.81-3.50 (m, 5H), 3.16-3.08 (m, 2H), 3.06 (s, 3H), 3.02 (s, 3H), 1.13 (d, J=6.4 Hz, 3H), 1.04 (d, J=7.2 Hz, 3H).

Example 35: Synthesis of 42

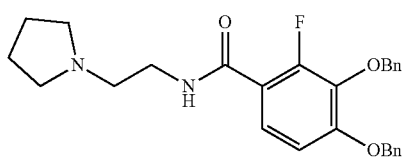

42a $^1$H NMR (CD$_3$OD, 400 MHz): δ 7.76 (app t, J=8.8 Hz, 1H), 7.45-7.28 (m, 10H), 7.18-7.11 (m, 1H), 6.83 (dd, J=9.2, 0.8 Hz, 1H), 5.16 (s, 2H), 5.09 (s, 2H), 3.56 (q, J=6.0 Hz, 2H), 2.69 (t, J=6.0 Hz, 2H), 2.59-2.51 (m, 4H), 1.84-1.76 (m, 4H).

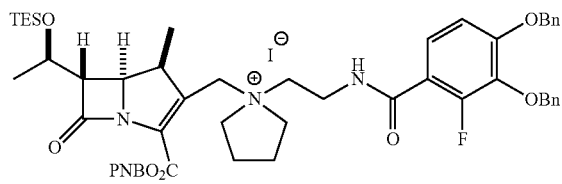

42b $^1$H NMR (CD$_3$OD, 400 MHz): δ 8.17 (d, J=8.4 Hz, 2H), 7.77 (d, J=8.8 Hz, 2H), 7.51 (app t, J=8.8 Hz, 1H), 7.48-7.26 (m, 10H), 7.01 (dd, J=9.2, 0.8 Hz, 1H), 5.47 (d, J=14.0 Hz, 1H), 5.41 (d, J=14.0 Hz, 1H), 5.33 (d, J=14.0 Hz, 1H), 5.21 (s, 2H), 5.07 (s, 2H), 4.53 (dd, J=10.0, 2.8 Hz, 1H), 4.38 (qd, J=6.0, 3.6 Hz, 1H), 4.14 (d, J=14.4 Hz, 1H), 3.84-3.74 (m, 4H), 3.69-3.46 (m, 6H), 2.30-2.15 (m, 4H), 1.26 (d, J=7.6 Hz, 3H), 1.25 (d, J=5.6 Hz, 3H), 0.95 (t, J=8.0 Hz, 9H), 0.62 (q, J=8.0 Hz, 6H).

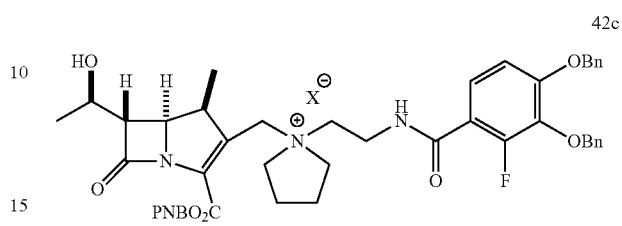

42c $^1$H NMR (CD$_3$OD, 400 MHz): δ 8.18 (d, J=8.4 Hz, 2H), 7.74 (d, J=8.4 Hz, 2H), 7.49 (app t, J=8.4 Hz, 1H), 7.48-7.25 (m, 10H), 7.01 (d, J=8.8 Hz, 1H), 5.49 (d, J=13.6 Hz, 1H), 5.40 (d, J=14.0 Hz, 1H), 5.31 (d, J=14.0 Hz, 1H), 5.21 (s, 2H), 5.06 (s, 2H), 4.42 (dd, J=10.0, 2.8 Hz, 1H), 4.20-4.10 (m, 2H), 3.83-3.72 (m, 4H), 3.68-3.46 (m, 5H), 3.45 (dd, J=5.6, 2.4 Hz, 1H), 2.31-2.14 (m, 4H), 1.30 (d, J=6.4 Hz, 3H), 1.26 (d, J=7.6 Hz, 3H).

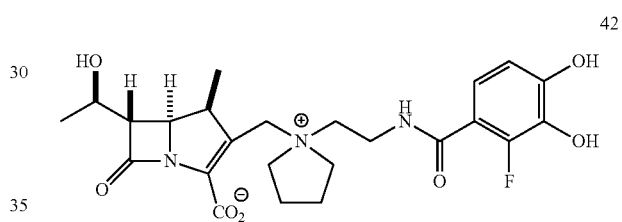

42

$^1$H NMR (400 MHz, DMSO-d6): δ 8.28-8.22 (m, 1H), 7.04 (app t, J=8.4 Hz, 1H), 6.66 (d, J=8.8 Hz, 1H), 5.30 (d, J=13.2 Hz, 1H), 4.08 (dd, J=10.0, 2.8 Hz, 1H), 3.96-3.90 (m, 1H), 3.79 (d, J=13.2 Hz, 1H), 3.77-3.68 (m, 1H), 3.63-3.40 (m, 7H), 3.20-3.08 (m, 2H), 2.20-1.95 (m, 4H), 1.14 (d, J=6.0 Hz, 3H), 1.04 (d, J=6.0 Hz, 3H).

Example 36: Synthesis of 43

SCHEME 4.

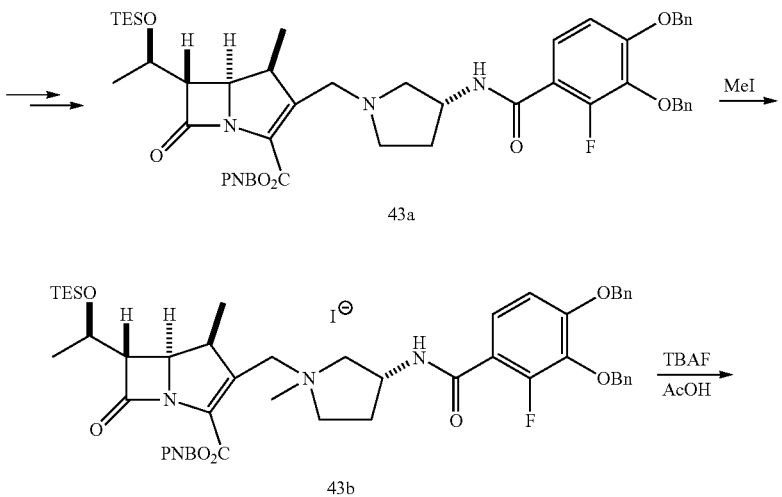

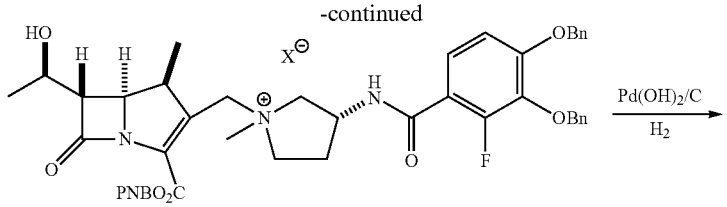

43c

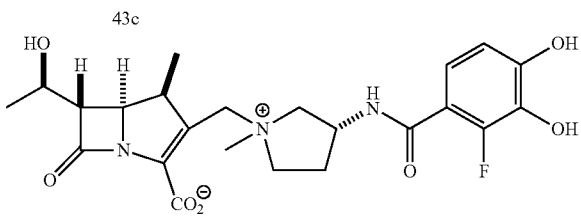

43

Step 1

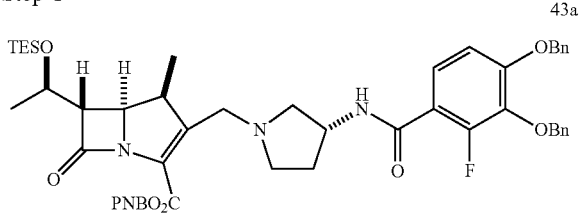

43a

Using a similar procedure described for Example 1, 43a was obtained as a yellow foam.

$^1$H NMR (CDCl$_3$, 400 MHz): δ 8.21 (d, J=8.4 Hz, 2H), 7.77 (app t, J=8.8 Hz, 1H), 7.66 (d, J=8.0 Hz, 2H), 7.43-7.29 (m, 10H), 6.89-6.82 (m, 2H), 5.44 (d, J=13.6 Hz, 1H), 5.23 (d, J=14.4 Hz, 1H), 5.17 (s, 2H), 5.08 (s, 2H), 4.67-4.58 (m, 1H), 4.30-4.20 (m, 2H), 3.89 (d, J=14.4 Hz, 1H), 3.42-3.32 (m, 2H), 3.24 (dd, J=6.0, 3.2 Hz, 1H), 2.89-2.80 (m, 2H), 2.56 (dd, J=9.2, 3.2 Hz, 1H), 2.43-2.30 (m, 2H), 1.74-1.66 (m, 1H), 1.26 (d, J=6.4 Hz, 3H), 1.20 (d, J=7.2 Hz, 3H), 0.95 (t, J=8.0 Hz, 9H), 0.60 (q, J=8.0 Hz, 6H).

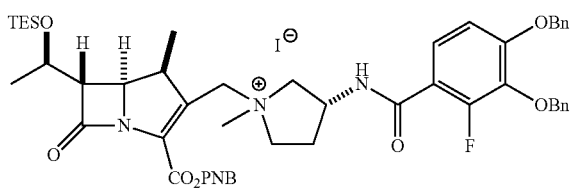

43b

A solution of 43a (590 mg, 0.66 mmol) and MeI (4.1 mL, 66 mmol) in CH$_2$Cl$_2$ (3.0 mL) was stirred for 15 h at r.t. After concentration under reduced pressure, the crude was purified on a silica gel column (CH$_2$Cl$_2$/MeOH=99/1 to 96/4) to afford two diastereomers, 43b (an upper spot on TLC) as a yellow foam (150 mg) and 43b' (a lower spot on TLC) as a yellow form (235 mg). A diastereomer 43b was used for the next step.

diastereomer 43b $^1$H NMR (CDCl$_3$, 400 MHz): δ 8.23 (d, J=8.0 Hz, 2H), 7.68 (d, J=8.8 Hz, 2H), 7.63 (app t, J=8.8 Hz, 1H), 7.58-7.52 (m, 1H), 7.42-7.27 (m, 10H), 6.80 (d, J=8.8 Hz, 1H), 5.43 (d, J=14.0 Hz, 1H), 5.32 (d, J=13.6 Hz, 1H), 5.26-5.16 (m, 1H), 5.14-5.08 (m, 3H), 5.07 (s, 2H), 4.88 (d, J=13.6 Hz, 1H), 4.59-4.52 (m, 1H), 4.39 (dd, J=9.6, 2.0 Hz, 1H), 4.35-4.27 (m, 2H), 4.02 (dd, J=11.2, 6.0 Hz, 1H), 3.89-3.82 (m, 1H), 3.46-3.34 (m, 5H), 2.85-2.63 (m, 2H), 1.42 (d, J=7.2 Hz, 3H), 1.21 (d, J=6.4 Hz, 3H), 0.93 (t, J=8.0 Hz, 9H), 0.59 (q, J=8.0 Hz, 6H).

diastereomer 43b'

$^1$H NMR (CDCl$_3$, 400 MHz): δ 8.19 (d, J=8.4 Hz, 2H), 7.85 (app t, J=8.0 Hz, 1H), 7.67-7.61 (m, 3H), 7.44-7.27 (m, 10H), 6.81 (d, J=9.6 Hz, 1H), 5.40 (d, J=13.6 Hz, 1H), 5.28 (d, J=13.6 Hz, 1H), 5.17 (d, J=13.6 Hz, 1H), 5.14 (s, 2H), 5.09 (s, 2H), 4.94-4.79 (m, 2H), 4.47 (dd, J=12.0, 9.6 Hz, 1H), 4.41 (dd, J=10.0, 2.8 Hz, 1H), 4.34-4.27 (m, 1H), 4.00 (dd, J=10.8, 8.8 Hz, 1H), 3.72-3.64 (m, 1H), 3.47-3.34 (m, 3H), 3.22 (s, 3H), 2.85-2.72 (m, 1H), 2.60-2.59 (m, 1H), 1.41 (d, J=6.8 Hz, 3H), 1.22 (d, J=6.4 Hz, 3H), 0.93 (t, J=8.0 Hz, 9H), 0.59 (q, J=8.0 Hz, 6H).

Step 3

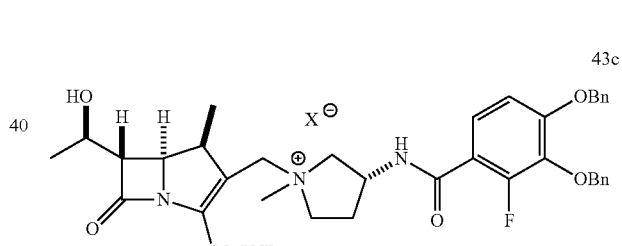

43c

Using a similar procedure described for Example 34, 43c was obtained as a white film.

$^1$H NMR (CD$_3$OD, 400 MHz): δ 8.24 (d, J=8.4 Hz, 2H), 7.78 (d, J=8.8 Hz, 2H), 7.48-7.27 (m, 12H), 7.03 (dd, J=8.8, 1.2 Hz, 1H), 5.53 (d, J=13.6 Hz, 1H), 5.41 (d, J=13.6 Hz, 1H), 5.21 (s, 2H), 5.20 (d, J=13.2 Hz, 1H), 5.08 (s, 2H), 4.94-4.86 (m, 1H), 4.42 (dd, J=10.0, 3.2 Hz, 1H), 4.21-4.03 (m, 3H), 3.86-3.69 (m, 3H), 3.55-3.45 (m, 2H), 3.25 (s, 3H), 2.78-2.68 (m, 1H), 2.46-2.35 (m, 1H), 1.30 (d, J=6.4 Hz, 3H), 1.26 (d, J=7.6 Hz, 3H).

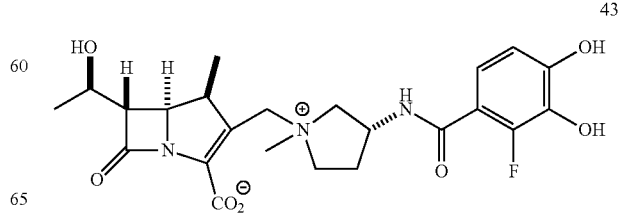

43

Using a similar procedure described for Example 34, 43 was obtained as a white fluffy solid.
$^1$H NMR (400 MHz, DMSO-d6): δ 8.45-8.40 (m, 1H), 6.94 (app t, J=8.0 Hz, 1H), 6.64 (d, J=8.0 Hz, 1H), 5.36 (d, J=12.8 Hz, 1H), 4.76-4.62 (m, 1H), 4.08 (dd, J=9.2, 2.4 Hz, 1H), 4.01-3.45 (m, 6H), 3.15-3.05 (m, 4H), 2.91-2.85 (m, 1H), 2.62-2.10 (m, 2H), 1.13 (d, J=6.0 Hz, 3H), 1.02 (d, J=7.2 Hz, 3H).
Example 37: Synthesis of 101
SCHEME 5.
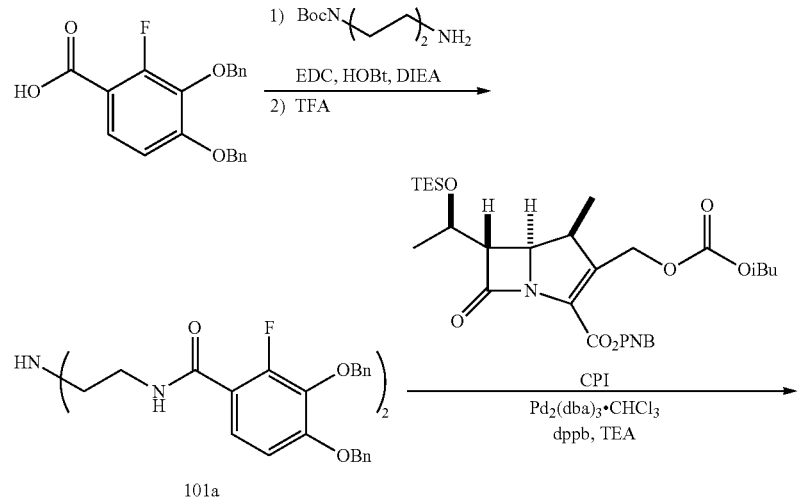
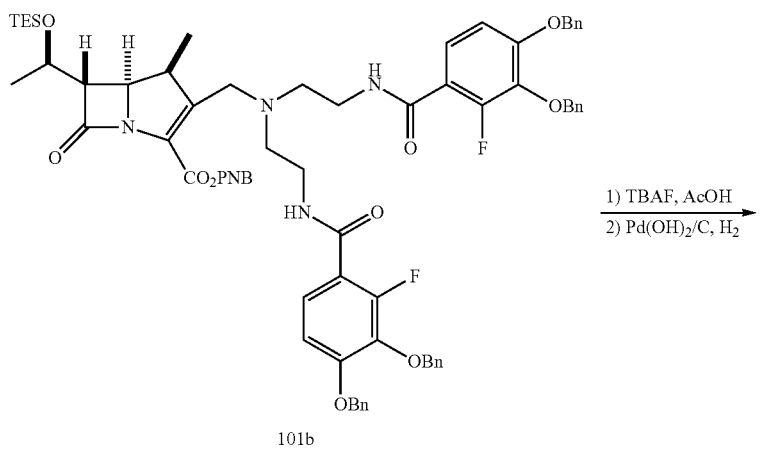
101b
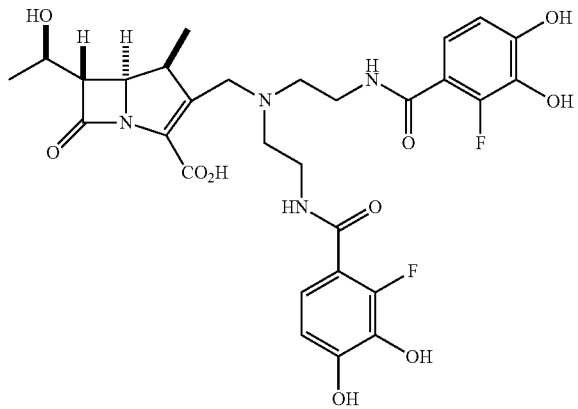
101

Step 1

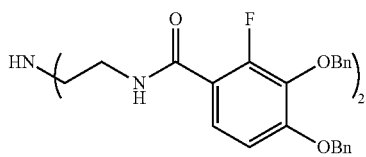
101a

Into a solution of t-butyl bis(2-aminoethyl)carbamate (407 mg, 2.0 mmol) in CH₂Cl₂ (20 mL) were added HOBt.xH₂O (890 mg, 5.6 mmol), DIEA (1.40 mL, 8.0 mmol), 2-fluoro-3,4-bis(phenylmethoxy)benzoic acid (1.62 g, 4.6 mmol), and EDC.HCl (1.07 g, 5.6 mmol), respectively, at r.t. After stirring overnight, the reaction solution was diluted with EtOAc (100 mL) and washed with half sat. NH₄Cl (50 mL). The organic phase was dried over MgSO₄ and concentrated in vacuo. The crude was then treated with TFA (2.3 mL, 30 mmol) in CH₂Cl₂ (20 mL) at r.t. After stirring overnight, the reaction solution was concentrated under reduced pressure. The residue was treated with half sat. NaHCO₃ (100 mL) and extracted with EtOAc (200 mL+50 mL). The combined organics were dried over MgSO₄ and concentrated in vacuo. The crude was purified on a silica gel column (CH₂Cl₂/MeOH=98/2 to 92/8) to afford 101a (1.01 g, 65% in 2 steps) as an off-white solid.

¹H NMR (400 MHz, CDCl₃): δ 7.67 (t, J=8.8 Hz, 2H), 7.40-7.20 (m, 20H), 6.73 (d, J=8.4 Hz, 2H), 5.05 (s, 4H), 4.99 (s, 4H), 3.64 (q, J=5.2 Hz, 4H), 3.02 (t, J=5.2 Hz, 4H).

Step 2

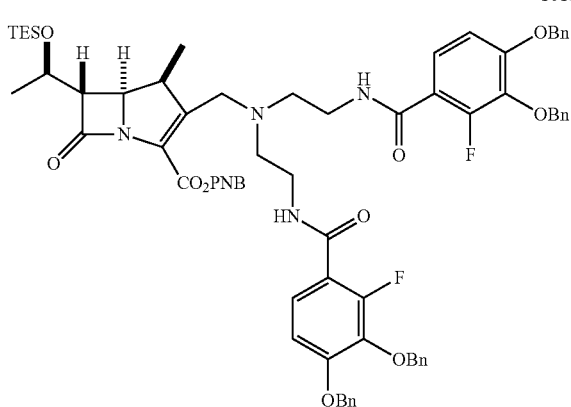
101b

A degassed solution of Pd₂(dba)₃.CHCl₃ (135 mg, 0.13 mmol) and dppb (166 mg, 0.39 mmol) in toluene (14 mL) was stirred for 1 h at r.t. under N₂. The solution was then transferred into another degassed solution of CPI (768 mg, 1.3 mmol) and 101a (1.01 g, 1.3 mmol) in THF (7 mL). TEA (181 μL, 1.3 mmol) was subsequently added. After stirring overnight, the reaction mixture was concentrated and purified on a silica gel column (Hex/EtOAc=5/5 to 3/7) to afford 101b (1.15 mg, 71%) as a slightly yellow foam.

¹H NMR (400 MHz, CDCl₃): δ 8.16 (d, J=8.8 Hz, 2H), 7.68 (t, J=8.4 Hz, 2H), 7.63 (t, J=8.8 Hz, 2H), 7.42-7.24 (m, 20H), 7.05-6.96 (m, 2H), 6.76 (d, J=9.2 Hz, 2H), 5.43 (d, J=14.0 Hz, 1H), 5.20 (d, J=14.0 Hz, 1H), 5.06 (s, 4H), 4.99 (s, 4H), 4.22 (qd, J=6.8, 4.8 Hz, 1H), 4.16 (dd, J=9.6, 2.8 Hz, 1H), 4.11 (d, J=14.8 Hz, 1H), 3.66-3.48 (m, 4H), 3.33-3.21 (m, 2H), 3.18 (dd, J=4.8, 3.2 Hz, 1H), 2.88-2.79 (m, 2H), 2.68-2.60 (m, 1H), 1.11 (d, J=6.0 Hz, 3H), 1.09 (d, J=8.0 Hz, 3H), 0.88 (t, J=8.0 Hz, 9H), 0.54 (q, J=8.0 Hz, 6H).

Step 3

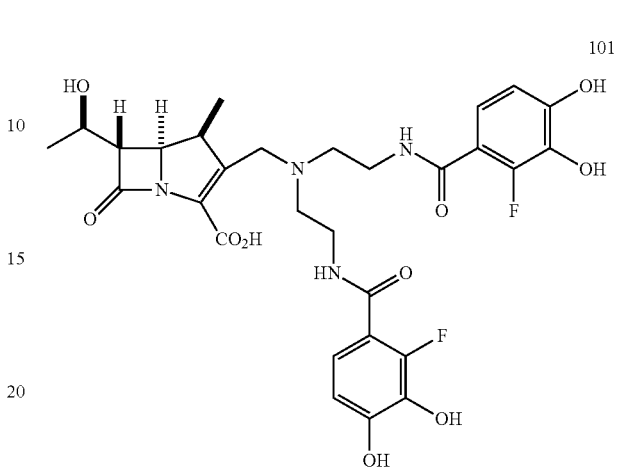
101

Into a solution of 101b (380 mg, 0.30 mmol) in THF (10 mL) were added AcOH (34 μL, 0.60 mmol) and TBAF (1.0 M in THF) (900 mL, 2.67 mmol), respectively, at 0° C. After stirring for 1.5 h at r.t., the reaction solution was quenched with 0.25M SPB (pH 7.0, 30 mL) and extracted with EtOAc (30 mL+15 mL). The combined organics were dried over MgSO₄ and concentrated in vacuo.

Into a mixture of the crude in THF/H₂O/IPA (5/4/2) (30 mL) was added Pd(OH)₂/C (20 wt %, 210 mg) at 0° C. After stirring for 1 h at 0° C. under H₂, the reaction mixture was diluted with DI water and EtOAc (20 mL each) and then filtered through Celite. The filter cake was washed with DI water and EtOAc repeatedly (40 mL each). After the phase separation, the aqueous phase was purified on a resin column (SP-207) to afford 101 (37 mg, 19% yield in 2 steps) as a white fluffy solid.

¹H NMR (600 MHz, DMSO-d₆): δ 10.0 (br s, 2H), 9.23 (br s, 2H), 7.97-7.91 (m, 2H), 6.97 (t, J=8.4 Hz, 2H), 6.60 (d, J=8.4 Hz, 1H), 5.02 (br s, 1H), 3.99 (dd, J=10.2, 2.4 Hz, 1H), 3.92 (p, J=6.0 Hz, 1H), 3.74 (d, J=15.0 Hz, 1H), 3.50-3.25 (m, 5H), 3.18-3.11 (m, 2H), 2.84-2.78 (m, 2H), 2.63-2.57 (m, 2H), 1.09 (d, J=6.0 Hz, 3H), 1.01 (d, J=6.6 Hz, 3H).

Example 38: Synthesis of 102

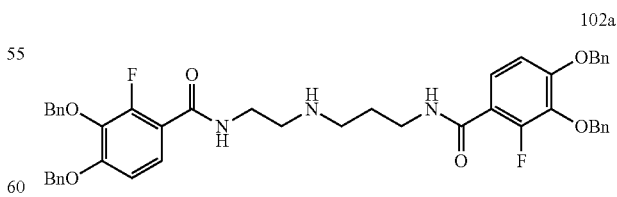
102a

¹H NMR (400 MHz, CDCl₃): δ 7.70 (t, J=9.2 Hz, 1H), 7.59 (t, J=8.8 Hz, 1H), 7.40-7.20 (m, 20H), 7.20-7.10 (m, 2H), 6.76 (d, J=8.8 Hz, 1H), 6.74 (d, J=8.8 Hz, 1H), 5.11 (s, 2H), 5.08 (s, 2H), 5.03 (s, 2H), 5.02 (s, 2H), 3.71 (q, J=5.2 Hz, 2H), 3.58 (q, J=5.6 Hz, 2H), 3.06 (t, J=5.2 Hz, 2H), 2.89 (t, J=6.0 Hz, 2H), 1.94 (p, J=6.0 Hz, 2H).

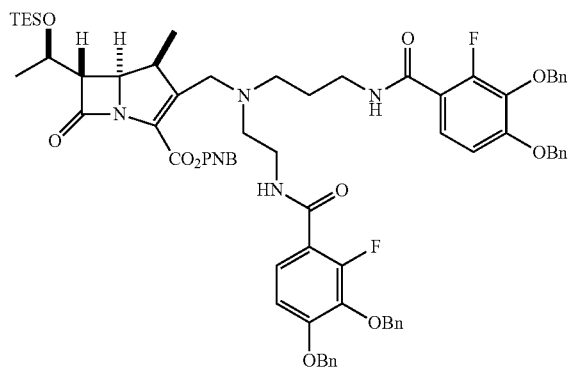

102b

¹H NMR (400 MHz, CDCl₃): δ 8.18 (d, J=8.8 Hz, 2H), 7.76 (t, J=8.8 Hz, 1H), 7.72 (t, J=8.8 Hz, 1H), 7.64 (d, J=8.8 Hz, 2H), 7.44-7.25 (m, 20H), 7.14-7.06 (m, 1H), 6.82 (d, J=8.0 Hz, 1H), 6.80 (d, J=8.4 Hz, 1H), 6.77-6.68 (m, 1H), 5.43 (d, J=13.6 Hz, 1H), 5.20 (d, J=14.0 Hz, 1H), 5.13 (s, 2H), 5.12 (s, 2H), 5.05 (s, 4H), 4.22 (p, J=5.6 Hz, 1H), 4.17 (dd, J=10.4, 3.2 Hz, 1H), 4.04 (d, J=14.8 Hz, 1H), 3.69-3.60 (m, 1H), 3.53-3.42 (m, 3H), 3.37-3.28 (m, 1H), 3.25-3.17 (m, 2H), 2.83-2.74 (m, 1H), 2.72-2.63 (m, 1H), 2.58-2.50 (m, 1H), 2.50-2.41 (m, 1H), 1.86-1.75 (m, 2H), 1.16 (d, J=6.4 Hz, 3H), 1.12 (d, J=7.2 Hz, 3H), 0.90 (t, J=8.0 Hz, 9H), 0.56 (q, J=8.0 Hz, 6H).

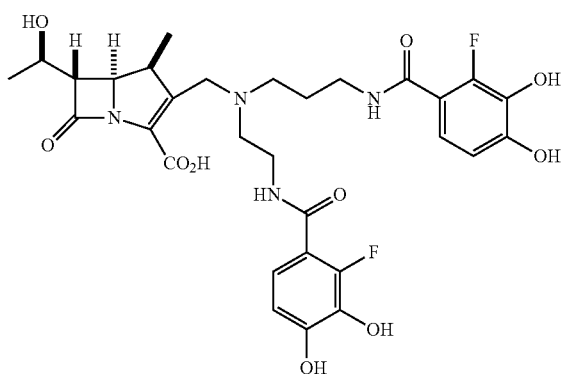

102

¹H NMR (600 MHz, DMSO-d₆): δ 9.97 (br s, 2H), 9.22 (br s, 2H), 8.05-7.97 (m, 2H), 7.02 (t, J=8.4 Hz, 1H), 6.93 (t, J=8.4 Hz, 1H), 6.62 (d, J=7.8 Hz, 1H), 6.61 (d, J=7.8 Hz, 1H), 4.99 (br s, 1H), 3.98 (d, J=7.8 Hz, 1H), 3.91 (p, J=6.0 Hz, 1H), 3.66-3.54 (m, 2H), 3.49-3.22 (m, 6H), 3.12-3.03 (m, 2H), 2.90-2.76 (m, 2H), 2.75-2.60 (m, 2H), 1.82-1.69 (m, 2H), 1.11 (d, J=6.0 Hz, 3H), 1.04 (d, J=7.8 Hz, 3H).

Example 39: Synthesis of 103

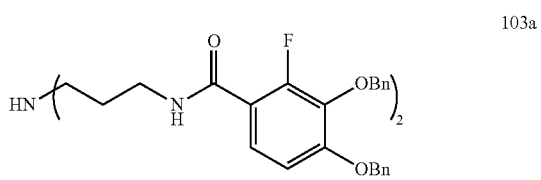

103a

¹H NMR (400 MHz, CDCl₃): δ 7.68 (t, J=9.2 Hz, 2H), 7.40-7.10 (m, 22H), 6.81 (d, J=9.2 Hz, 2H), 5.09 (s, 4H), 5.05 (s, 4H), 3.69-3.62 (m, 4H), 3.05-2.97 (m, 4H), 2.18-2.09 (m, 4H).

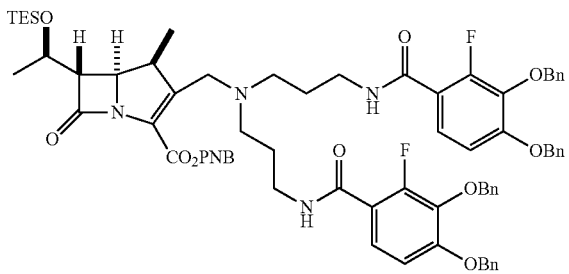

103b

¹H NMR (400 MHz, CDCl₃): δ 8.19 (d, J=8.4 Hz, 2H), 7.70 (t, J=8.8 Hz, 2H), 7.65 (d, J=8.4 Hz, 2H), 7.40-7.27 (m, 20H), 6.95-6.87 (m, 2H), 6.79 (d, J=8.0 Hz, 2H), 5.44 (d, J=14.0 Hz, 1H), 5.20 (d, J=14.0 Hz, 1H), 5.09 (s, 4H), 5.03 (s, 4H), 4.26-4.20 (m, 1H), 4.18 (dd, J=10.0, 2.8 Hz, 1H), 3.93 (d, J=14.8 Hz, 1H), 3.54-3.46 (m, 4H), 3.37-3.28 (m, 1H), 3.22 (dd, J=5.6, 3.2 Hz, 1H), 3.17 (d, J=14.8 Hz, 1H), 2.67-2.58 (m, 2H), 2.42-2.34 (m, 2H), 1.81-1.73 (m, 4H), 1.23 (d, J=5.6 Hz, 3H), 1.13 (d, J=7.6 Hz, 3H), 0.93 (t, J=8.0 Hz, 9H), 0.59 (q, J=8.0 Hz, 6H).

103

¹H NMR (400 MHz, DMSO-d₆): δ 8.03 (br s, 2H), 6.93 (t, J=8.4 Hz, 2H), 6.62 (d, J=8.4 Hz, 2H), 3.97 (dd, J=8.0, 1.6 Hz, 1H), 3.93-3.85 (m, 1H), 3.68 (d, J=15.6 Hz, 1H), 3.52-3.22 (m, 5H), 3.05 (dd, J=6.8, 2.4 Hz, 1H), 3.02-2.92 (m, 1H), 2.90-2.80 (m, 2H), 2.80-2.70 (m, 2H), 1.86-1.71 (m, 4H), 1.11 (d, J=6.4 Hz, 3H), 1.02 (d, J=6.8 Hz, 3H).

Example 40: Synthesis of 104

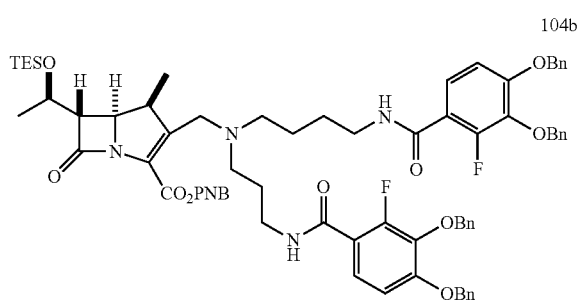

104b

¹H NMR (400 MHz, CDCl₃): δ 8.19 (d, J=8.8 Hz, 2H), 7.74 (td, J=8.7, 2.6 Hz, 2H), 7.65 (d, J=8.7 Hz, 2H), 7.46-7.24 (m, 20H), 6.98-6.85 (m, 1H), 6.84-6.79 (m, 2H), 6.74-6.66 (m, 1H), 5.43 (d, J=13.9 Hz, 1H), 5.19 (d, J=14.0 Hz, 1H), 5.13 (s, 4H), 5.06 (s, 4H), 4.28-4.16 (m, 2H), 3.93 (d, J=15.0 Hz, 1H), 3.51-3.40 (m, 3H), 3.36-3.28 (m, 1H), 3.21 (dd, J=5.5, 3.0 Hz, 1H), 3.15 (d, J=15.1 Hz, 1H), 2.62-2.52 (m, 2H), 2.41-2.30 (m, 2H), 1.77 (t, J=6.9 Hz, 1H), 1.64-1.49 (m, 4H), 1.23 (d, J=5.9 Hz, 3H), 1.12 (d, J=7.3 Hz, 3H), 0.93 (t, J=7.9 Hz, 9H), 0.59 (q, J=7.9 Hz, 6H).

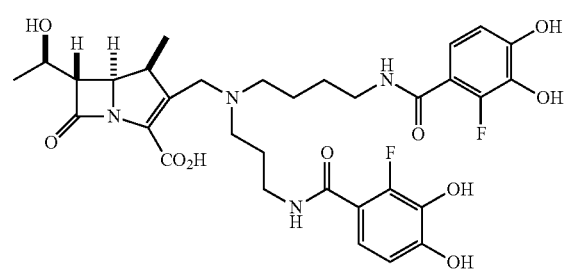

104

¹H NMR (400 MHz, DMSO-d₆): δ 8.02 (s, 1H), 7.96 (s, 1H), 6.95-6.85 (m, 2H), 6.64-6.59 (m, 2H), 4.00-3.86 (m, 2H), 3.72-2.67 (m, 12H), 1.78 (br, 2H), 1.51 (br, 4H), 1.12 (d, J=6.2 Hz, 3H), 1.04 (d, J=7.2 Hz, 3H).

Example 41: Synthesis of 105

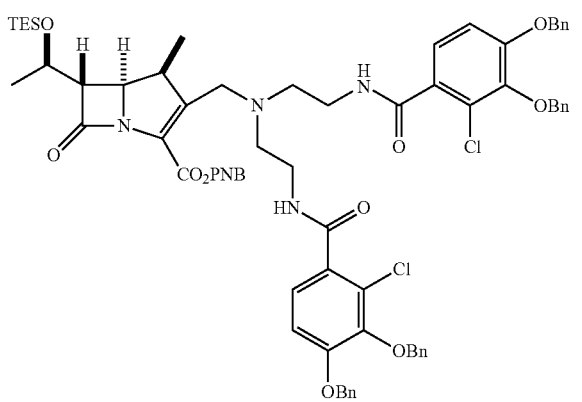

105b

¹H NMR (600 MHz, CDCl₃): δ 8.14 (d, J=8.7 Hz, 2H), 7.62 (d, J=8.9 Hz, 2H), 7.42-7.20 (m, 22H), 7.09 (t, J=5.3 Hz, 2H), 6.83 (d, J=8.7 Hz, 2H), 5.34 (d, J=14.0 Hz, 1H), 5.08 (d, J=14.0 Hz, 1H), 4.96 (s, 4H), 4.95 (s, 4H), 4.25-4.17 (m, 1H), 4.13-4.07 (m, 1H), 3.96 (d, J=14.5 Hz, 1H), 3.70-3.67 (m, 2H), 3.50-3.44 (m, 2H), 3.26-3.15 (m, 3H), 2.85-2.80 (m, 2H), 2.63-2.58 (m, 2H), 1.12 (d, J=6.2 Hz, 3H), 1.05 (d, J=7.4 Hz, 3H), 0.87 (t, J=7.9 Hz, 9H), 0.53 (q, J=7.9 Hz, 6H).

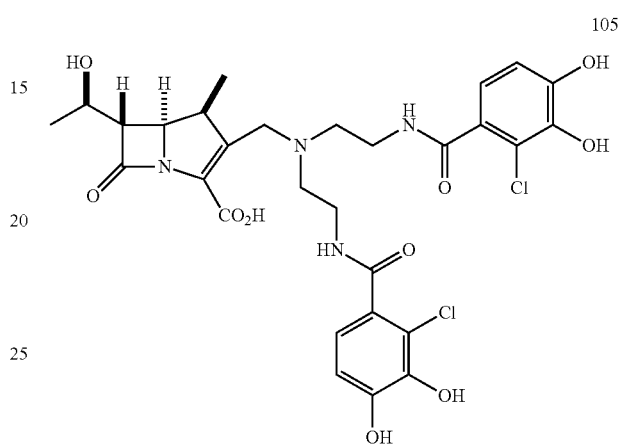

105

¹H NMR (600 MHz, DMSO-d₆): δ 8.11 (s, 2H), 6.93-6.34 (m, 4H), 4.00-3.96 (m, 1H), 3.90 (p, J=6.2 Hz, 1H), 3.80-3.76 (m, 1H), 3.43-2.34 (m, 12H), 1.10 (d, J=6.2 Hz, 3H), 1.02 (d, J=6.7 Hz, 3H).

Example 42: Synthesis of 106

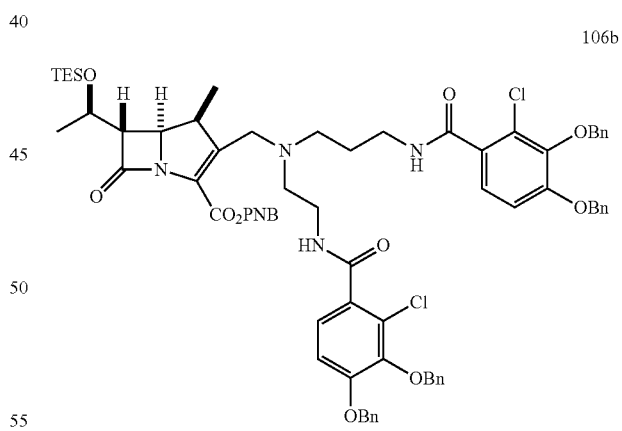

106b

¹H NMR (400 MHz, CDCl₃): δ 8.16 (d, J=8.8 Hz, 2H), 7.63 (d, J=8.8 Hz, 2H), 7.43-7.25 (m, 22H), 7.04 (t, J=4.8 Hz, 1H) 6.91-6.86 (m, 2H), 6.58 (t, J=5.6 Hz, 1H), 5.39 (d, J=14.0 Hz, 1H), 5.15 (d, J=14.0 Hz, 1H), 5.08 (s, 2H), 5.06, (s, 2H), 4.99 (s, 2H), 4.99 (s, 2H) 4.26-4.16 (m, 2H), 4.00 (d, J=14.8 Hz, 1H), 3.60-3.42 (m, 4H), 3.32-3.27 (m, 1H), 3.21-3.18 (m, 2H), 2.83-2.76 (m, 1H), 2.72-2.65 (m, 1H), 2.60-2.51 (m, 1H), 2.50-2.43 (m, 1H), 1.82-1.70 (m, 2H), 1.20 (d, J=6.4 Hz, 3H), 1.11 (d, J=7.6 Hz, 3H), 0.91 (t, J=8.4 Hz, 9H), 0.59 (q, J=7.6 Hz, 6H).

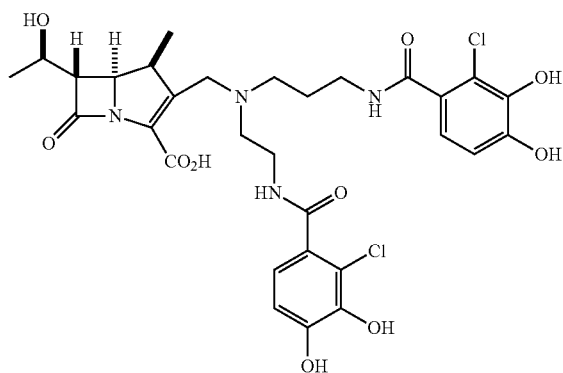

¹H NMR (400 MHz, DMSO-d₆): δ 8.16-8.15 (m, 2H), 6.77-6.67 (m, 4H), 3.99-3.84 (m, 2H), 3.70-3.30 (m, 9H), 2.80 (br, 2H), 2.65 (br, 2H), 1.73 (br, 2H), 1.11 (d, J=6.0 Hz, 3H), 1.03 (d, J=8.0 Hz, 3H).

Example 43: Synthesis of 107

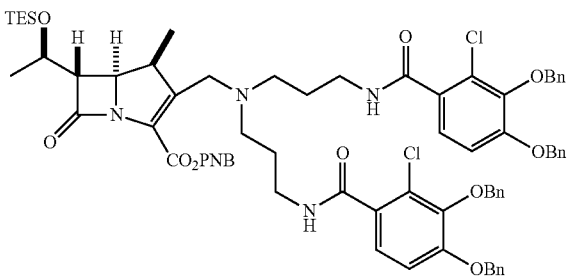

¹H NMR (600 MHz, CDCl₃): δ 8.19 (d, J=8.6 Hz, 2H), 7.65 (d, J=8.5 Hz, 2H), 7.47-7.24 (m, 22H), 6.93 (t, J=5.8 Hz, 2H), 6.84 (d, J=8.6 Hz, 2H), 5.42 (d, J=13.9 Hz, 1H), 5.19 (d, J=13.9 Hz, 1H), 5.02 (s, 4H), 4.96 (s, 4H), 4.30-4.23 (m, 1H), 4.18 (dd, J=10.3, 3.1 Hz, 1H), 3.87 (d, J=14.9 Hz, 1H), 3.55-3.45 (m, 4H), 3.30-3.26 (m, 1H), 3.22 (dd, J=5.3, 3.1 Hz, 1H), 3.18 (d, J=14.9 Hz, 1H), 2.70-2.65 (m, 2H), 2.30-2.31 (m, 2H), 1.79-1.75 (m, 4H), 1.24 (d, J=6.2 Hz, 3H), 1.10 (d, J=7.3 Hz, 3H), 0.94 (t, J=7.9 Hz, 9H), 0.60 (q, J=7.9 Hz, 6H).

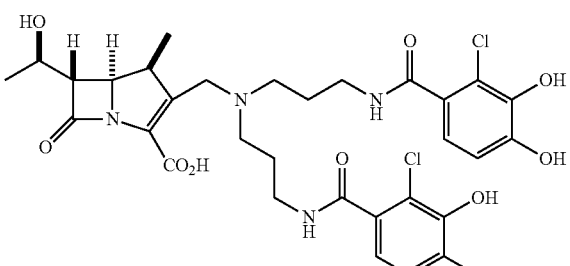

¹H NMR (600 MHz, DMSO-d₆): δ 8.20 (t, J=5.8 Hz, 2H), 6.77-6.63 (m, 4H), 3.97 (dd, J=10.1, 2.9 Hz, 1H), 3.89 (q, J=6.3 Hz, 1H), 3.66 (br, 1H), 3.55-2.66 (m, 7H), 1.75 (br, 4H), 1.12 (d, J=6.2 Hz, 3H), 1.03 (d, J=7.2 Hz, 3H).

Example 44: Synthesis of 108

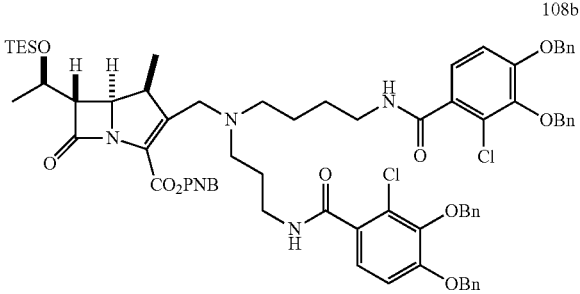

¹H NMR (400 MHz, CDCl₃): 8.18 (d, J=8.8 Hz, 2H), 7.64 (d, J=9.0 Hz, 2H), 7.46-7.26 (m, 22H), 6.87 (dd, J=9.8, 8.7 Hz, 2H), 6.83-6.78 (m, 1H), 6.57-6.54 (m, 1H), 5.41 (d, J=13.9 Hz, 1H), 5.18 (d, J=14.0 Hz, 1H), 5.09 (s, 4H), 4.99 (s, 4H), 4.29-4.21 (m, 1H), 4.18 (dd, J=10.2, 3.1 Hz, 1H), 3.90 (d, J=15.0 Hz, 1H), 3.60-3.33 (m, 4H), 3.33-3.25 (m, 1H), 3.22 (dd, J=5.3, 3.1 Hz, 1H), 3.14 (d, J=15.0 Hz, 1H), 2.64-2.56 m, 2H), 2.43-2.26 (m, 2H), 1.79-1.75 (m, 2H), 1.69-1.47 (m, 4H), 1.24 (d, J=6.1 Hz, 3H), 1.10 (d, J=7.2 Hz, 3H), 0.93 (t, J=7.9 Hz, 9H), 0.59 (q, J=7.9, 6H).

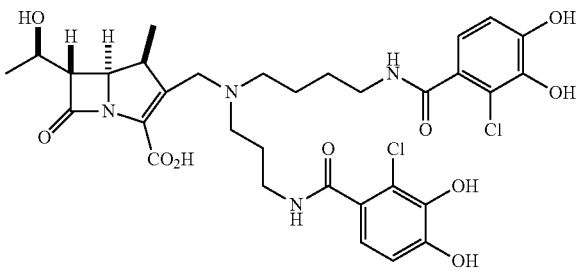

¹H NMR (400 MHz, DMSO-d₆): δ 8.16 (br, 2H), 6.99-6.54 (m, 4H), 3.98 (d, J=10.0 Hz, 1H), 3.90 (t, J=6.3 Hz, 1H), 3.67-2.63 (m, 12H), 1.76 (br, 2H), 1.59 (br, 2H), 1.49 (br, 2H), 1.12 (d, J=6.2 Hz, 3H), 1.04 (d, J=7.4 Hz, 3H).

Example 45: Synthesis of 109

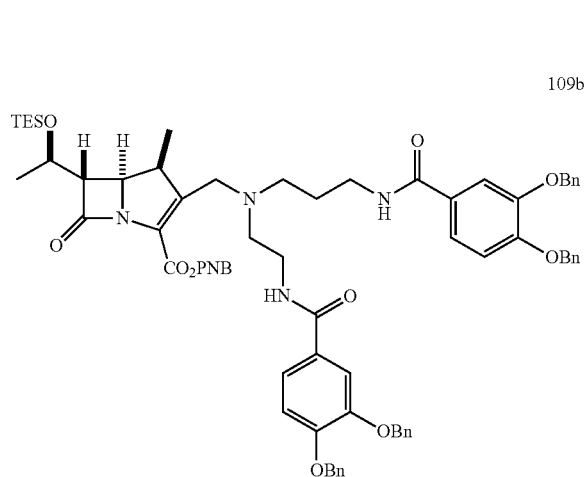

109b

¹H NMR (400 MHz, CDCl₃): δ 8.19 (d, J=8.8 Hz, 2H), 7.67-7.62 (m, 3H), 7.51-7.23 (m, 23H), 7.15 (t, J=5.6 Hz, 1H) 6.91-6.88 (m, 2H), 6.63 (t, J=5.2 Hz, 1H), 5.40 (d, J=14.0 Hz, 1H), 5.19-5.10 (m, 9H), 4.21-4.16 (m, 1H), 4.03-4.00 (m, 1H), 3.87 (d, J=15.0 Hz, 1H), 3.86-3.60 (m, 1H), 3.52-3.30 (m, 3H), 3.24-3.17 (m, 2H), 3.11-3.09 (m, 1H), 2.78-2.62 (m, 2H), 2.42-2.30 (m, 2H) 1.17 (br, 2H) 1.04 (d, J=6.4 Hz, 3H), 0.99 (d, J=7.2 Hz, 3H), 0.90 (t, J=8.4 Hz, 9H), 0.55 (q, J=8.0 Hz, 6H).

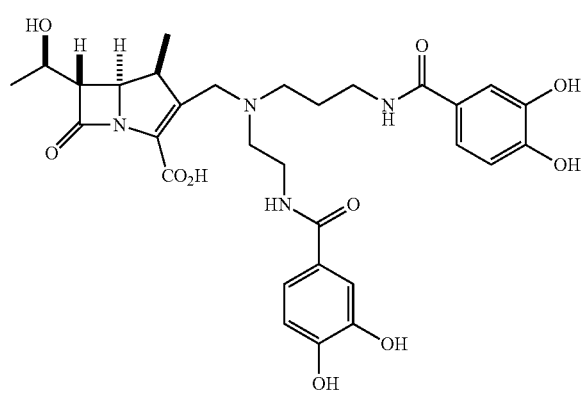

109

¹H NMR (400 MHz, DMSO-d₆): δ 9.40 (br, 1H), 9.10 (br, 1H), 8.20-8.16 (br, 2H), 7.26-7.25 (m, 2H), 7.17-7.13 (m, 2H), 6.73-6.71 (m, 2H), 4.94 (br, 1H), 3.96-3.85 (m, 2H), 3.58 (br, 1H), 3.42-3.20 (m, 5H), 3.08-2.99 (m, 2H), 3.90-3.60 (m, 4H), 1.80-1.70 (m, 2H), 1.07 (d, J=6.4 Hz, 3H), 0.99 (d, J=7.6 Hz, 3H).

Example 46: Synthesis of 110

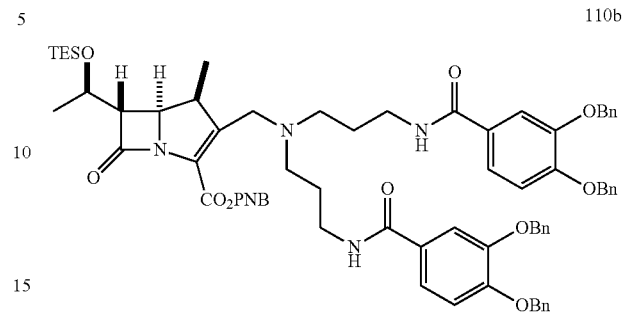

110b

¹H NMR (600 MHz, CDCl₃): δ 8.21 (d, J=8.7 Hz, 2H), 7.65 (d, J=8.4 Hz, 2H), 7.51 (d, J=2.1 Hz, 2H), 7.41-7.24 (m, 22H), 6.88-6.77 (m, 4H), 5.43 (d, J=13.8 Hz, 1H), 5.19 (d, J=14.0 Hz, 1H), 5.08 (s, 4H), 5.07 (s, 4H), 4.32-4.22 (m, 1H), 4.18 (dd, J=10.3, 3.1 Hz, 1H), 3.86 (d, J=14.8 Hz, 1H), 3.59-3.54 (m, 2H), 3.48-3.42 (m, 2H), 3.35-3.28 (m, 1H), 3.22 (dd, J=5.2, 3.1 Hz, 1H), 3.17 (d, J=14.8 Hz, 1H), 2.62-2.58 (m, 2H), 2.33-2.28 (m, 2H), 1.79-1.72 (m, 4H), 1.23 (d, J=6.2 Hz, 3H), 1.11 (d, J=7.3 Hz, 3H), 0.93 (t, J=7.9 Hz, 9H), 0.60 (q, J=7.9 Hz, 6H).

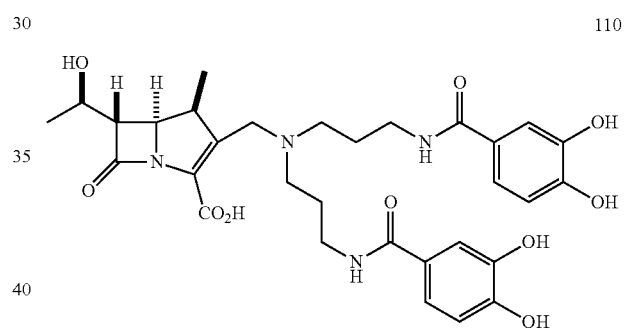

110

¹H NMR (600 MHz, DMSO-d₆): δ 9.41 (br, 1H), 9.14 (br, 1H), 8.18 (br, 2H), 7.25 (d, J=2.1 Hz, 2H), 7.13 (dd, J=8.2, 2.2 Hz, 2H), 6.72 (d, J=8.2 Hz, 2H), 4.93 (br, 1H), 3.95-3.80 (m, 2H), 3.70-2.57 (m, 12H), 1.75 (br, 4H), 1.07 (d, J=6.3 Hz, 3H), 0.96 (d, J=7.3 Hz, 3H).

Example 47: Synthesis of 111

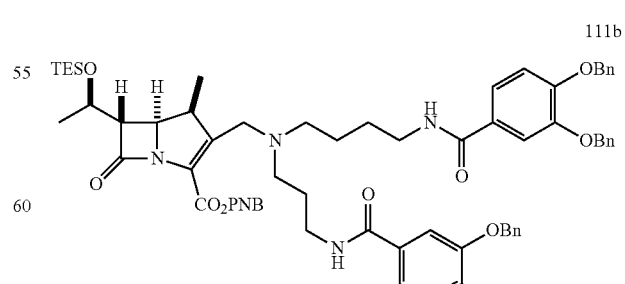

111b

¹H NMR (400 MHz, CDCl₃): δ 8.19 (d, J=8.8 Hz, 2H), 7.64 (d, J=8.9 Hz, 2H), 7.55-7.48 (m, 2H), 7.44-7.22 (m,

22H), 6.88-6.81 (m, 3H), 6.51 (br, 1H), 5.41 (d, J=14.0 Hz, 1H), 5.17 (d, J=14.0 Hz, 1H), 5.13 (s, 4H), 5.08 (s, 2H), 5.07 (s, 2H), 4.29-4.20 (m, 1H), 4.19-4.15 (m, 1H), 3.89 (d, J=15.0 Hz, 1H), 3.52-3.40 (m, 4H), 3.36-3.28 (m, 2H), 3.21-3.19 (m, 1H), 3.14 (d, J=14.8 Hz, 1H), 2.60-2.54 (m, 2H), 2.38-2.25 (m, 2H), 1.78-1.69 (m, 2H), 1.61 (br, 2H), 1.52 (br, 2H), 1.22 (d, J=6.1 Hz, 3H), 1.09 (d, J=7.3 Hz, 3H), 0.92 (t, J=7.9 Hz, 9H), 0.58 (q, J=7.9, 6H).

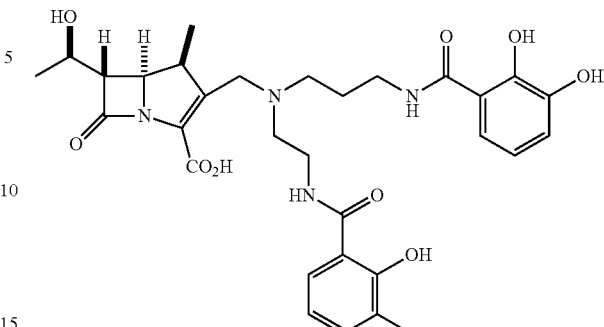

111

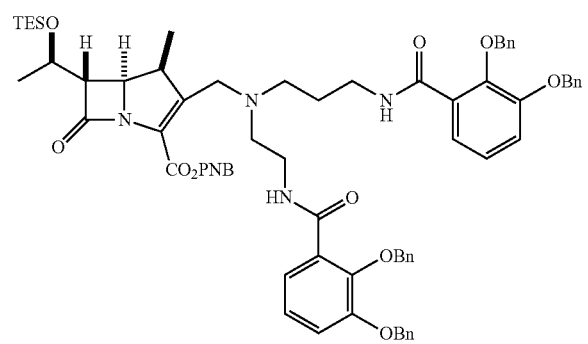

¹H NMR (400 MHz, DMSO-d₆): δ 8.16 (s, 1H), 8.09 (s, 1H), 7.27 (d, J=12.9 Hz, 2H), 7.18-7.11 (m, 2H), 6.73 (d, J=3.5 Hz, 1H), 6.71 (d, J=3.5 Hz, 1H), 3.98-3.83 (m, 2H), 3.71-3.62 (m, 2H), 3.24-2.65 (m, 10H), 1.80-1.72 (m, 2H), 1.60-141 (m, 4H), 1.09 (d, J=6.2 Hz, 3H), 0.99 (d, J=7.3 Hz, 3H).

Example 48: Synthesis of 112

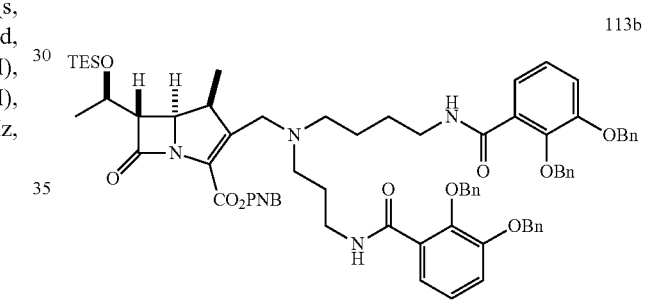

112b

¹H NMR (400 MHz, CDCl₃): δ 8.17 (d, J=8.8 Hz, 2H), 7.96 (t, J=5.5 Hz, 1H), 7.88 (t, J=5.5 Hz, 1H), 7.77-7.67 (m, 2H), 7.62 (d, J=8.9 Hz, 2H), 7.50-7.24 (m, 20H), 7.15-7.14 (m, 4H), 5.38 (d, J=14.0 Hz, 1H), 5.20-5.11 (m, 5H), 5.05 (d, J=4.8 Hz, 4H), 4.24-4.20 (m, 1H), 4.05 (dd, J=10.3, 3.1 Hz, 1H), 3.88 (d, J=15.1 Hz, 1H), 3.42-3.30 (m, 1H), 3.28-3.08 (m, 5H), 2.99 (d, J=15.2 Hz, 1H), 2.42-2.30 (m, 2H), 2.25-2.12 (m, 2H), 1.78 (s, 2H), 1.16 (d, J=6.2 Hz, 3H), 0.97 (d, J=7.4 Hz, 3H), 0.92 (t, J=7.9 Hz, 9H), 0.58 (q, J=7.6 Hz, 6H).

112

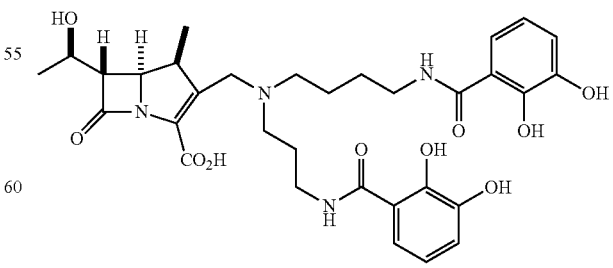

¹H NMR (400 MHz, DMSO-d₆): δ 8.94 (br, 2H), 7.28-7.21 (m, 2H), 6.89 (d, J=7.8 Hz, 2H), 6.67-6.62 (m, 2H), 3.98-3.94 (m, 1H), 3.90-3.87 (m, 1H), 3.68 (d, J=15.5 Hz, 1H), 3.42-3.20 (m, 5H), 3.06-3.00 (m, 2H), 3.86-3.56 (m, 4H), 1.79 (br, 2H), 1.09 (d, J=6.2 Hz, 3H), 0.99 (d, J=7.2 Hz, 3H).

Example 49: Synthesis of 113

113b

¹H NMR (400 MHz, CDCl₃): δ 8.18 (d, J=8.8 Hz, 2H), 7.89 (br, 2H), 7.71 (q, J=4.7 Hz, 2H), 7.63 (d, J=8.5 Hz, 2H), 7.51-7.27 (m, 20H), 7.13 (d, J=4.6 Hz, 4H), 5.40 (d, J=14.0 Hz, 1H), 5.16-5.14 (m, 6H), 5.06 (s, 4H), 4.30-4.19 (m, 1H), 4.17-4.08 (m, 1H), 3.80 (d, J=15.2 Hz, 1H), 3.51-3.14 (m, 6H), 3.01 (d, J=15.2 Hz, 1H), 2.47-2.25 (m, 2H), 2.20-2.10 (m, 2H), 1.48-1.42 (m, 2H), 1.33-1.18 (m, 7H), 1.04 (d, J=7.3 Hz, 3H), 0.93 (t, J=7.9 Hz, 9H), 0.59 (q, J=8.1 Hz, 6H).

113

¹H NMR (600 MHz, DMSO-d₆): δ 8.87 (s, 1H), 8.83 (s, 1H), 7.24 (dd, J=17.0, 8.0 Hz, 2H), 6.88 (dd, J=7.9, 3.2 Hz, 2H), 6.67-6.63 (m, 2H), 3.95 (dd, J=10.1, 3.0 Hz, 1H), 3.87

(p, J=6.2 Hz, 1H), 3.73-3.68 (m, 1H), 3.48 (d, J=15.9 Hz, 1H), 3.41-3.16 (m, 4H), 3.01 (s, 1H), 2.95 (t, J=8.6 Hz, 1H), 2.83 (s, 2H), 2.74 (s, 2H), 1.99-1.71 (m, 2H), 1.68-1.48 (m, 4H), 1.08 (d, J=6.3 Hz, 3H), 0.99 (d, J=7.3 Hz, 3H).

Example 50: Synthesis of 114

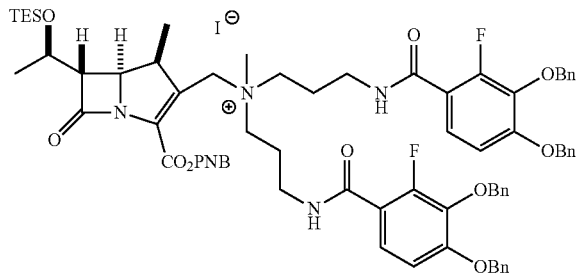

114b $^1$H NMR (400 MHz, CDCl$_3$): δ 8.17 (d, J=9.2 Hz, 2H), 7.62 (d, J=8.4 Hz, 2H), 7.60 (td, J=8.8, 4.4 Hz, 2H), 7.42-7.27 (m, 20H), 6.75 (dd, J=9.2, 4.0 Hz, 2H), 5.36 (d, J=14.0 Hz, 1H), 5.25 (d, J=14.4 Hz, 1H), 5.13 (d, J=13.2 Hz, 1H), 5.08-5.02 (m, 8H), 4.44 (dd, J=10.0, 2.8 Hz, 1H), 4.32-4.24 (m, 2H), 4.10-4.00 (m, 1H), 3.68-3.45 (m, 8H), 3.30 (t, J=3.6 Hz, 1H), 3.22 (s, 3H), 2.30-2.10 (m, 4H), 1.27 (d, J=6.8 Hz, 3H), 1.18 (d, J=6.0 Hz, 3H), 0.92 (t, J=8.0 Hz, 9H), 0.59 (q, J=8.0 Hz, 6H).

114

$^1$H NMR (400 MHz, DMSO-d$_6$): δ 8.10 (br s, 2H), 6.98 (t, J=8.0 Hz, 2H), 6.62 (d, J=7.6 Hz, 2H), 5.24 (d, J=13.6 Hz, 1H), 4.04 (dd, J=10.0, 2.8 Hz, 1H), 3.95-3.87 (m, 1H), 3.69 (d, J=13.2 Hz, 1H), 3.50-3.10 (m, 10H), 2.91 (s, 3H), 2.00-1.86 (m, 4H), 1.10 (d, J=5.6 Hz, 3H), 0.98 (d, J=6.4 Hz, 3H).

Example 51: Synthesis of 115

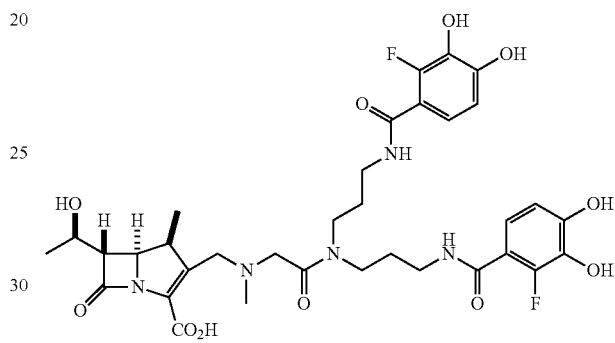

115

$^1$H NMR (600 MHz, DMSO-d$_6$): δ 9.93 (br s, 2H), 9.24 (br s, 2H), 8.05-7.97 (m, 1H), 7.97-7.92 (m, 1H), 6.96 (t, J=8.4 Hz, 1H), 6.95 (t, J=9.0 Hz, 1H), 6.62 (d, J=9.0 Hz, 1H), 6.61 (d, J=8.4 Hz, 1H), 5.00 (br s, 1H), 4.02 (dd, J=10.2, 3.0 Hz, 1H), 3.92 (p, J=6.6 Hz, 1H), 3.70-3.55 (m, 3H), 3.35-3.17 (m, 9H), 3.15 (d, J=6.0, 3.0 Hz, 1H), 3.06-3.00 (m, 1H), 2.40 (s, 3H), 1.82-1.74 (m, 2H), 1.72-1.67 (m, 2H), 1.12 (d, J=6.6 Hz, 3H), 1.03 (d, J=6.6 Hz, 3H).

Example 52: Synthesis of 116

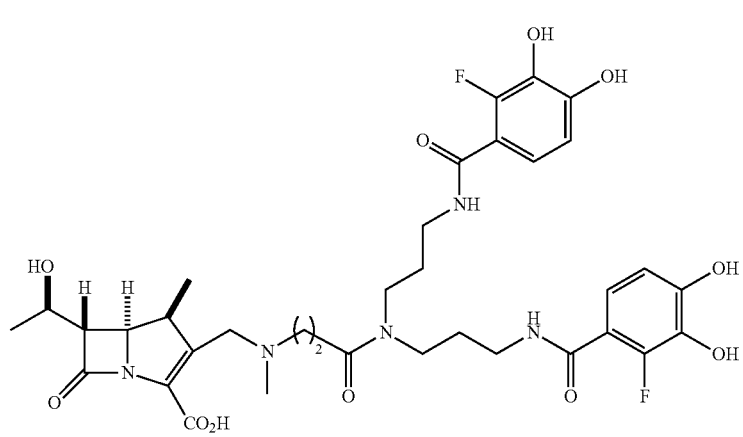

116

¹H NMR (400 MHz, DMSO-d₆): δ 8.09-8.05 (m, 1H), 7.97-7.93 (m, 1H), 6.97 (t, J=8.4 Hz, 1H), 6.93 (t, J=8.4 Hz, 1H), 6.61 (d, J=8.4 Hz, 2H), 3.99 (dd, J=10.2, 2.4 Hz, 1H), 3.91 (p, J=6.0 Hz, 1H), 3.50-3.00 (m, 13H), 2.99-2.92 (m, 1H), 2.73-2.63 (m, 2H), 2.48 (s, 3H), 1.82-1.74 (m, 2H), 1.71-1.63 (m, 2H), 1.12 (d, J=6.6 Hz, 3H), 1.04 (d, J=7.2 Hz, 3H).
Example 53: Synthesis of 117
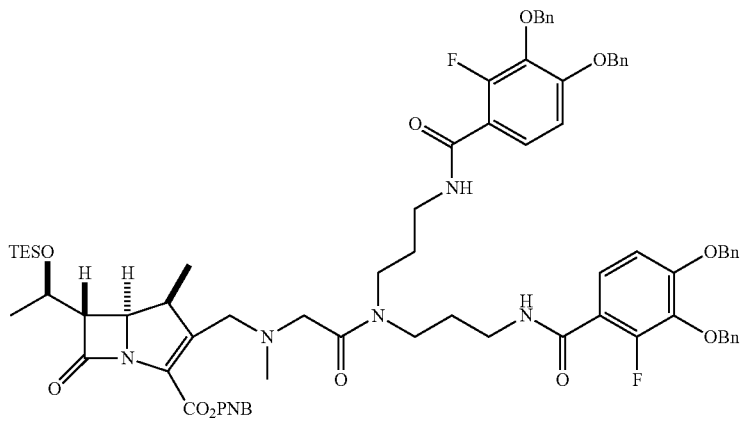
¹H NMR (400 MHz, CDCl₃): δ 8.18 (d, J=8.8 Hz, 2H), 7.70 (t, J=8.8 Hz, 2H), 7.63 (d, J=8.8 Hz, 2H), 7.42-7.27 (m, 20H), 7.16-7.08 (m, 2H), 6.79 (d, J=9.6 Hz, 2H), 5.42 (d, J=14.0 Hz, 1H), 5.17 (d, J=14.0 Hz, 1H), 5.11 (s, 4H), 5.03 (s, 4H), 4.23 (p, J=6.4 Hz, 1H), 4.15 (dd, J=10.4, 3.2 Hz, 1H), 3.77 (d, J=14.8 Hz, 1H), 3.53-3.46 (m, 4H), 3.33-3.25 (m, 1H), 3.21 (dd, J=5.6, 2.8 Hz, 1H), 3.11 (d, J=15.6 Hz, 1H), 2.62-2.38 (m, 8H), 2.13 (s, 3H), 1.78-1.70 (m, 4H), 1.24 (d, J=6.4 Hz, 3H), 1.12 (d, J=7.2 Hz, 3H), 0.93 (t, J=8.0 Hz, 9H), 0.59 (q, J=8.0 Hz, 6H).
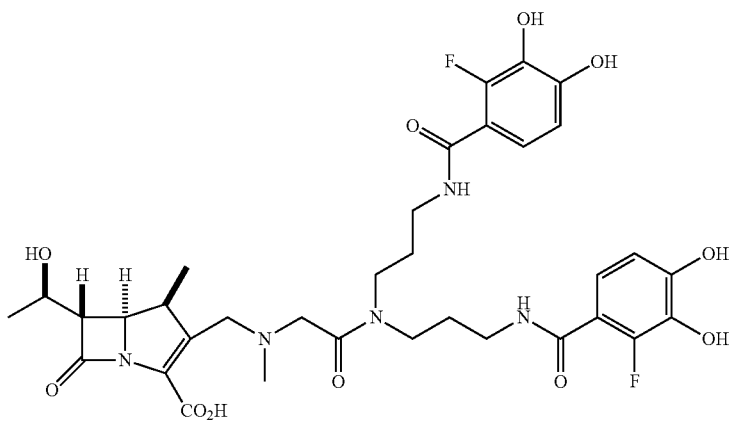
¹H NMR (400 MHz, DMSO-d₆): δ 8.00-7.94 (m, 2H), 6.93 (t, J=8.4 Hz, 2H), 6.60 (d, J=8.4 Hz, 2H), 3.99 (dd, J=10.0, 2.8 Hz, 1H), 3.94-3.81 (m, 2H), 3.46 (d, J=15.6 Hz, 1H), 3.26-3.18 (m, 4H), 3.12 (dd, J=6.8, 3.2 Hz, 1H), 3.01-2.87 (m, 3H), 2.75-2.42 (m, 9H), 1.68-1.58 (m, 4H), 1.12 (d, J=6.4 Hz, 3H), 1.04 (d, J=7.2 Hz, 3H).

Example 54: Synthesis of 118
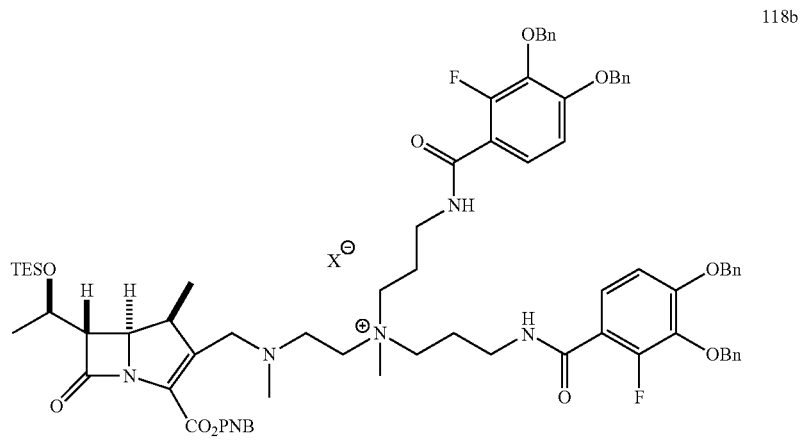
118b
$^1$H NMR (400 MHz, CDCl$_3$): δ 8.17 (d, J=9.2 Hz, 2H), 7.80-7.73 (m, 2H), 7.63 (d, J=8.8 Hz, 2H), 7.57 (t, J=8.8 Hz, 2H), 7.41-7.27 (m, 20H), 6.76 (d, J=9.2 Hz, 2H), 5.39 (d, J=14.0 Hz, 1H), 5.18 (d, J=14.0 Hz, 1H), 5.08 (s, 4H), 5.04 (s, 4H), 4.27-4.18 (m, 2H), 3.92 (d, J=14.4 Hz, 1H), 3.63-3.3.41 (m, 11H), 3.21 (dd, J=5.6, 3.2 Hz, 1H), 3.14 (s, 3H), 3.04 (d, J=13.6 Hz, 1H), 2.90-2.70 (m, 2H), 2.20 (s, 3H), 2.16-2.04 (m, 4H), 1.22 (d, J=6.4 Hz, 3H), 1.09 (d, J=7.6 Hz, 3H), 0.92 (t, J=8.0 Hz, 9H), 0.58 (q, J=8.0 Hz, 6H).
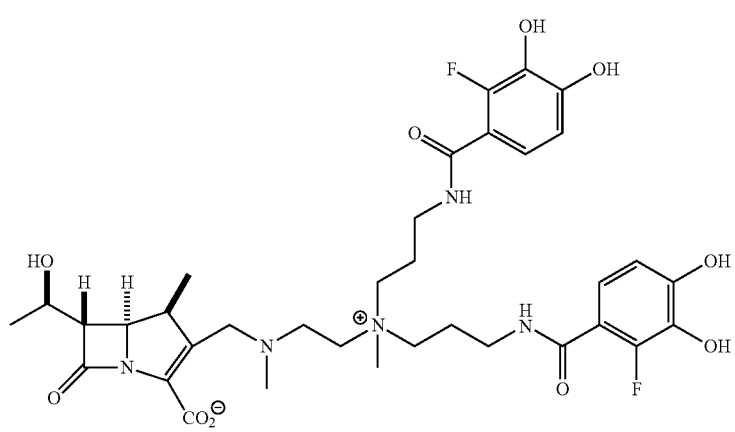
118
$^1$H NMR (400 MHz, DMSO-d$_6$): δ 8.18-8.08 (m, 2H), 6.92 (t, J=8.0 Hz, 2H), 6.61-6.56 (m, 2H), 3.99 (d, J=13.2 Hz, 1H), 3.89 (dd, J=9.6, 2.4 Hz, 1H), 3.79 (p, J=6.4 Hz, 1H), 3.50-2.40 (m, 18H), 2.19 (s, 3H), 1.96-1.82 (m, 4H), 1.11 (d, J=6.0 Hz, 3H), 0.97 (d, J=6.8 Hz, 3H).

Example 55: Synthesis of 119

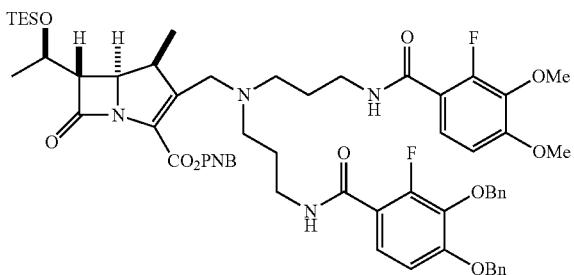

119b

¹H NMR (400 MHz, CDCl₃): δ 8.20 (d, J=8.4 Hz, 2H), 7.75-7.68 (m, 2H), 7.66 (d, J=8.4 Hz, 2H), 7.42-7.27 (m, 10H), 6.97-6.88 (m, 2H), 6.82 (d, J=8.0 Hz, 1H), 6.72 (d, J=9.2 Hz, 1H), 5.44 (d, J=14.0 Hz, 1H), 5.20 (d, J=13.6 Hz, 1H), 5.15 (s, 2H), 5.05 (s, 2H), 4.24 (p, J=6.0 Hz, 1H), 4.18 (dd, J=10.4, 2.8 Hz, 1H), 3.93 (d, J=14.8 Hz, 1H), 3.85 (s, 6H), 3.54-3.45 (m, 4H), 3.36-3.27 (m, 1H), 3.22 (dd, J=5.2, 3.2 Hz, 1H), 3.17 (d, J=15.2 Hz, 1H), 2.67-2.58 (m, 2H), 2.42-2.33 (m, 2H), 1.77 (p, J=6.4 Hz, 4H), 1.23 (d, J=5.6 Hz, 3H), 1.13 (d, J=7.2 Hz, 3H), 0.93 (t, J=8.0 Hz, 9H), 0.59 (q, J=8.0 Hz, 6H).

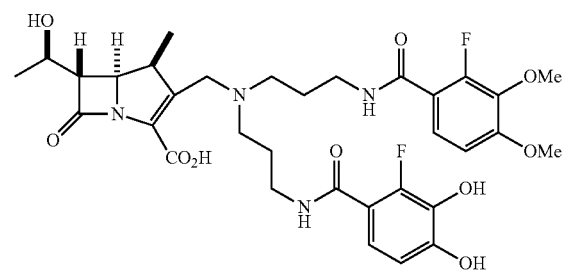

119

¹H NMR (400 MHz, DMSO-d₆): δ 10.03 (br s, 1H), 9.32 (br s, 1H), 8.27-8.20 (m, 1H), 8.07-8.02 (m, 1H), 7.33 (t, J=8.4 Hz, 1H), 6.97-6.89 (m, 2H), 6.61 (d, J=8.4 Hz, 2H), 4.99 (br s, 1), 3.97 (dd, J=10.4, 2.4 Hz, 1H), 3.92-3.68 (m, 8H), 3.50 (d, J=16.4 Hz, 1H), 3.35-3.20 (m, 4H), 3.04 (dd, J=6.4, 2.4 Hz, 1H), 3.01-2.92 (m, 1H), 2.90-2.80 (m, 2H), 2.80-2.70 (m, 2H), 1.88-1.70 (m, 4H), 1.11 (d, J=5.6 Hz, 3H), 1.02 (d, J=6.8 Hz, 3H).

Example 56: Synthesis of 120

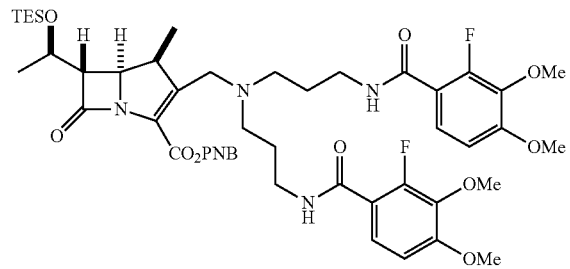

120b

¹H NMR (400 MHz, CDCl₃): δ 8.21 (d, J=8.8 Hz, 2H), 7.72 (t, J=8.8 Hz, 2H), 7.66 (d, J=8.0 Hz, 2H), 6.97-6.88 (m, 2H), 6.75 (d, J=9.2 Hz, 2H), 5.44 (d, J=14.0 Hz, 1H), 5.21 (d, J=14.0 Hz, 1H), 4.25 (p, J=6.0 Hz, 1H), 4.18 (dd, J=10.8, 3.2 Hz, 1H), 3.96-3.85 (m, 13H), 3.56-3.45 (m, 4H), 3.37-3.27 (m, 1H), 3.22 (dd, J=5.2, 3.2 Hz, 1H), 3.17 (d, J=15.2 Hz, 1H), 2.68-2.58 (m, 2H), 2.42-2.34 (m, 2H), 1.78 (p, J=6.8 Hz, 4H), 1.23 (d, J=5.6 Hz, 3H), 1.13 (d, J=7.6 Hz, 3H), 0.93 (t, J=8.0 Hz, 9H), 0.59 (q, J=8.0 Hz, 6H).

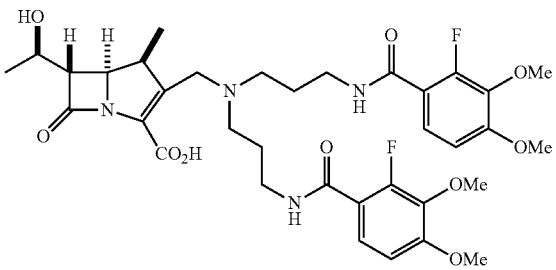

120

¹H NMR (400 MHz, DMSO-d₆): δ 8.26-8.20 (m, 2H), 7.33 (t, J=8.4 Hz, 2H), 6.93 (dd, J=8.8, 1.2 Hz, 2H), 4.99 (br s, 1H), 3.97 (dd, J=10.0, 2.4 Hz, 1H), 3.93-3.66 (m, 14H), 3.51 (d, J=16.0 Hz, 1H), 3.34-3.20 (m, 4H), 3.04 (dd, J=6.4, 2.8 Hz, 1H), 3.02-2.92 (m, 1H), 2.90-2.80 (m, 2H), 2.80-2.70 (m, 2H), 1.87-1.70 (m, 4H), 1.11 (d, J=6.0 Hz, 3H), 1.03 (d, J=7.2 Hz, 3H).

Biological Activity Data

Test Example 1

The MIC (minimum inhibitory concentration) was determined by the CLSI (Clinical and Laboratory Standards Institute) methods. The agar dilution method for determining antimicrobial susceptibility was carried out using Mueller Hinton-II agar and the amount of inoculation was $10^4$ CFU/spot. Broth dilution tests were performed using Mueller Hinton-II broth. All assays were run with the indicated control strains, available from the ATCC (American Type Culture Collection, Rockville, Md.). Results of the antimicrobial susceptibility tests of compounds against Gram-negative organisms are shown in Tables.

TABLE 1

| No. | Species | Code | β-lactamase produced |
|---|---|---|---|
| 1 | A. baumannii | 4010 | OXA-51 |
| 2 | A. baumannii | KABA 01-33 | OXA-2, VIM-2 |
| 3 | E. coli | ATCC10536 | |
| 4 | K. pneumoniae | ATCC10031 | |
| 5 | P. aeruginosa | ATCC27853 | |

TABLE 2

| Compounds | A. baumannii | | E. coil | K. pneumoniae | P. aeruginosa |
|---|---|---|---|---|---|
| | 4010 | KABA 01-33 | ATCC10536 | ATCC10031 | ATCC27853 |
| 1 | 2 | 1 | 0.5 | 0.063 | 4 |
| 5 | 8 | 2 | 1 | 0.13 | 16 |
| 6 | 4 | 1 | 0.5 | 0.063 | 8 |
| 8 | 8 | 4 | 1 | 0.5 | >32 |

TABLE 2-continued

| Com- | A. baumannii | | E. coil | K. pneumoniae | P. aeruginosa |
|---|---|---|---|---|---|
| pounds | 4010 | KABA 01-33 | ATCC10536 | ATCC10031 | ATCC27853 |
| 15 | >32 | >32 | 32 | 1 | >32 |
| 19 | 4 | 1 | 0.5 | 0.063 | 4 |
| 20 | 16 | 4 | 0.5 | 0.25 | 16 |
| 22 | >32 | 32 | 2 | 0.5 | >32 |
| 23 | >32 | 16 | 8 | 2 | >32 |
| 25 | 16 | 8 | 0.5 | 0.25 | 32 |
| 26 | 8 | 2 | 0.5 | 0.13 | 8 |
| 27 | 8 | 16 | 0.063 | 0.063 | 16 |

TABLE 3

| No. | Species | Code | β-lactamase produced |
|---|---|---|---|
| 1 | A. baumannii | FSAb-029 | OXA-2, IMP-1 |
| 2 | A. baumannii | FSAb-065 | OXA-2, VIM-2 |
| 3 | A. baumannii | FSAb-039 | OXA-51 |
| 4 | A. baumannii | FSAb-056 | OXA-23, OXA-51 |
| 5 | E. coli | FSEco-054 | ESBL |
| 6 | K. pneumoniae | ATCC BAA-1904 | KPC-3 |
| 7 | P. aeruginosa | FSPa-121 | OXA-17 |

TABLE 4

| | A. baumannii | | | | E. coil | K. pneumoniae | P. aeruginosa |
|---|---|---|---|---|---|---|---|
| Compounds | FSAb-029 | FSAb-065 | FSAb-039 | FSAb-056 | FSEco-054 | BAA-1904 | FSPa-121 |
| 1 | 1 | 1 | 2 | 2 | 1 | 8 | 2 |
| 2 | 2 | 2 | 4 | 2 | 2 | 16 | 2 |
| 3 | 4 | 2 | 4 | 4 | 4 | 32 | 4 |
| 4 | 8 | 4 | 8 | 8 | 8 | 16 | 8 |
| 5 | 8 | 8 | 8 | 8 | 4 | 32 | 8 |
| 6 | 2 | 2 | 4 | 2 | 1 | 32 | 2 |
| 7 | 2 | 2 | 4 | 2 | 2 | 16 | 2 |
| 10 | 16 | 16 | >32 | 16 | >32 | 8 | >32 |
| 11 | 32 | 32 | >32 | 32 | >32 | 8 | >32 |
| 12 | 32 | 32 | >32 | 32 | >32 | 4 | >32 |
| 13 | 32 | 16 | >32 | 32 | >32 | 8 | >32 |
| 14 | >32 | >32 | >32 | >32 | >32 | 16 | >32 |
| 16 | 4 | 8 | 8 | 8 | 8 | >32 | 8 |
| 17 | 2 | 2 | 8 | 4 | 2 | 32 | 4 |
| 18 | 8 | 1 | 4 | 4 | 2 | 16 | 2 |
| 19 | 8 | 8 | 8 | 8 | 8 | 8 | 4 |
| 21 | 8 | 2 | 8 | 8 | 4 | 8 | 2 |
| 26 | 16 | 4 | 16 | 4 | 4 | 32 | 4 |
| 28 | 0.5 | 0.5 | 8 | 4 | 2 | >32 | 2 |
| 29 | 1 | 1 | 8 | 4 | 2 | >32 | 2 |
| 30 | 2 | 0.5 | 4 | 4 | 2 | 16 | 2 |
| 31 | 2 | 0.5 | 4 | 4 | 2 | 32 | 2 |
| 32 | 2 | 1 | >32 | 16 | 4 | >32 | 1 |
| 33 | 4 | 1 | 32 | 8 | 4 | >32 | 2 |
| 34 | 2 | 8 | 8 | 8 | 2 | >32 | 8 |
| 35 | 4 | 2 | 8 | 4 | 2 | >32 | 4 |
| 36 | 4 | N.A. | 4 | 8 | 4 | 32 | N.A. |
| 37 | 8 | 4 | 32 | 16 | 8 | >32 | 8 |
| 38 | 0.5 | 0.25 | 4 | 4 | 2 | 16 | 4 |
| 39 | 4 | 1 | 8 | 8 | 2 | 8 | 16 |
| 40 | 8 | 4 | 16 | 8 | 4 | 16 | 4 |
| 41 | 8 | N.A. | 16 | 32 | 4 | 8 | N.A. |
| 42 | 4 | N.A. | 8 | 16 | 2 | 16 | N.A. |

Test Example 2

Antimicrobial Susceptibility Test was performed by the CLSI (Clinical and Laboratory Standards Institute) methods. The agar dilution method for determining antimicrobial susceptibility was carried out using Mueller Hinton-II agar and the amount of inoculation was $10^4$ CFU/spot. Broth dilution tests were performed using the Mueller Hinton-II broth. All assays were run with the indicated control strains, available from the ATCC (American Type Culture Collection, Rockville, Md.). Results of the antimicrobial susceptibility tests of compounds against Gram-negative organisms are shown in Tables.

Test Example 3

Antimicrobial Susceptibility Test was performed by the CLSI (Clinical and Laboratory Standards Institute) methods. The agar dilution method for determining antimicrobial susceptibility was carried out using Mueller Hinton-II agar and the amount of inoculation was $10^4$ CFU/spot. Broth dilution tests were performed using the Mueller Hinton-II broth. All assays were run with the indicated control strains, available from the ATCC (American Type Culture Collection, Rockville, Md.). Results of the antimicrobial susceptibility tests of compounds against Gram-negative organisms are shown in Tables.

TABLE 5

| No. | Species | Code | β-lactamase produced |
|---|---|---|---|
| 1 | A. baumannii | FSAb-029 | OXA-2, IMP-1 |
| 2 | A. baumannii | FSAb-039 | OXA-51 |
| 3 | A. baumannii | FSAb-056 | OXA-23, 51 |
| 4 | A. baumannii | FSAb-141 | PER-1, OXA-23, 51, 66 |
| 5 | E. coli | FSEco-054 | ESBL |
| 6 | K. pneumoniae | BAA-1904 | KPC-3 |
| 7 | P. aeruginosa | FSPa-102 | IMP-1 |
| 8 | P. aeruginosa | FSPa-141 | VIM-2 |

TABLE 6

| | Ab | | | | Ec | Kp | Pa | |
|---|---|---|---|---|---|---|---|---|
| Compounds | FSAb-029 | FSAb-039 | FSAb-056 | FSAb-141 | FSEco-054 | BAA-1904 | FSPa-102 | FSPa-141 |
| 101 | 0.25 | 2 | 4 | 0.5 | 2 | >32 | 1 | 1 |
| 102 | 0.25 | 1 | 4 | 0.5 | 1 | >32 | 1 | 2 |
| 103 | 0.25 | 1 | 4 | 1 | 1 | >32 | 2 | 8 |
| 104 | 0.5 | 2 | 4 | 1 | 1 | >32 | 2 | 4 |
| 105 | 0.5 | 2 | 2 | 0.5 | 1 | 16 | 1 | 0.5 |
| 106 | 0.25 | 1 | 2 | 0.5 | 1 | >32 | 1 | 1 |
| 107 | 0.25 | 1 | 2 | 0.5 | 0.5 | >32 | 1 | 1 |
| 108 | 1 | 2 | 4 | 1 | 1 | >32 | 2 | 2 |
| 109 | 1 | 2 | 4 | 2 | 2 | >32 | 4 | 4 |
| 110 | 2 | 8 | 8 | 4 | 4 | >32 | 8 | 16 |
| 111 | 2 | 4 | 8 | 2 | 4 | >32 | 4 | 16 |
| 112 | 4 | 8 | 32 | 4 | 8 | >32 | 16 | >32 |
| 113 | >32 | >32 | >32 | >32 | >32 | >32 | >32 | >32 |
| 114 | 1 | 32 | 8 | 2 | 2 | >32 | 4 | 4 |
| 115 | 2 | 4 | 8 | 2 | 2 | >32 | 2 | 4 |
| 116 | N.A | N.A | N.A | N.A | N.A | N.A | N.A | N.A |
| 117 | 2 | 4 | 4 | 2 | 1 | >32 | 2 | 8 |
| 118 | 2 | 8 | 8 | 4 | 2 | >32 | 4 | 8 |
| 119 | 4 | 8 | 8 | 8 | 16 | >32 | >32 | >32 |
| 120 | >32 | >32 | >32 | >32 | >32 | >32 | >32 | >32 |

Note;
Ab; *A. baumannii*,
Ec; *E. coli*,
Kp; *K. pneumoniae*,
Pa; *P. aeruginosa*

The compositions, methods and/or processes disclosed and claimed herein can be made and executed without undue experimentation in light of the present disclosure. While the compositions and methods of this invention have been described in terms of preferred embodiments, it will be apparent to those of skill in the art that variations may be applied to the compositions, methods and/or processes and in the steps or in the sequence of steps of the methods described herein without departing from the concept and scope of the invention.

More specifically, it will be apparent that certain agents which are both chemically and physiologically related may be substituted for the agents described herein while the same or similar results would be achieved. All such similar substitutes and modifications apparent to those skilled in the art are deemed to be within the scope and concept of the invention.

We claim:
1. A compound of Formula (I):

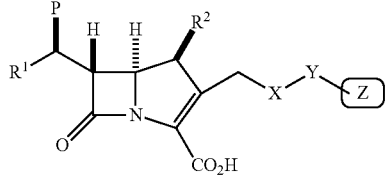

(I)

or a pharmaceutically acceptable salt or prodrug thereof, wherein:
$R^1$ and $R^2$ are each independently selected from H or alkyl;
P is H, OH, halogen, or hydroxyl protected by a hydroxyl protecting group;
X is (1) an acylic or cyclic alkyl amino based linker, optionally substituted by one or more substituents selected from the group consisting of alkyl, haloalkyl, OR, CN, CONRR', SR, or NRR' or (2) a quaternary ammonium cation based linker, optionally substituted by one or more substituents selected from the group consisting of alkyl, haloalkyl, OR, CN, $CONR_2$, SR, or NRR';
Y is a divalent —NR(C=O)—$(CR_2)_n$— or —(C=O)NR—$(CR_2)_n$— group, wherein n is 0, 1, or 2;
R and R' are each independently selected from H or alkyl; and
Z is an aromatic or heteroaromatic ring, substituted by one or more substituents selected from the group consisting of alkyl, haloalkyl, OH, halogen, or hydroxyl protected by a hydroxyl protecting group.

2. The compound of claim 1, wherein the compound has the structure of Formula (Ia):

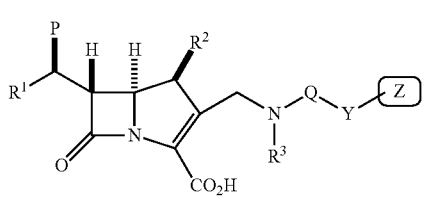

Formula (Ia)

or a pharmaceutically acceptable salt or prodrug thereof, wherein:
$R^1$, $R^2$ and $R^3$ are each independently selected from H or alkyl;
P is H, OH, halogen, or hydroxyl protected by a hydroxyl protecting group;
Q is —$(CR_2)_p$—W—$(CR_2)_q$—, optionally substituted by one or more substituents selected from the group consisting of alkyl, haloalkyl, OR, CN, CONRR', SR, or NRR', p and q are each independently 0, 1, or 2;
W is absent, —CONR—, or —NRCO—;
Y is a divalent —NR(C=O)—$(CR_2)_n$— or —(C=O)NR—$(CR_2)_n$— group, n is 0, 1, or 2;
R and R' are each independently selected from H or alkyl; and
Z is an aromatic or heteroaromatic ring, substituted by one or more substituents selected from the group consisting of alkyl, haloalkyl, OH, halogen, or hydroxyl protected by a hydroxyl protecting group.

3. The compound of claim 1, wherein the compound has the structure of Formula (Ib):

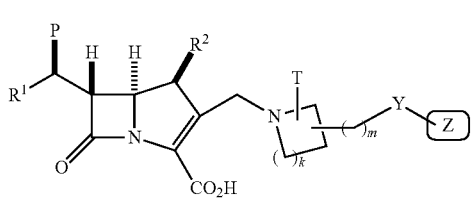

Formula (Ib)

or a pharmaceutically acceptable salt or prodrug thereof, wherein:
$R^1$ and $R^2$ are each independently selected from H or alkyl;
P is H, OH, halogen, or hydroxyl protected by a hydroxyl protecting group;
T is absent, alkyl, haloalkyl, OR, CN, CONRR', SR, or NRR';
Y is a divalent —NR(C=O)—$(CR_2)_n$— or —(C=O)NR—$(CR_2)_n$— group, n is 0, 1, or 2;
k is 1, 2, or 3;
m is 0, 1, or 2;
R and R' are each independently selected from H or alkyl; and
Z is an aromatic or heteroaromatic ring, substituted by one or more substituents selected from the group consisting of alkyl, haloalkyl, OH, halogen, or hydroxyl protected by a hydroxyl protecting group.

4. The compound of claim 1, wherein the compound has the structure of Formula (Ic):

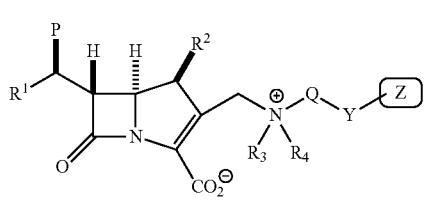

Formula Ic or a pharmaceutically acceptable salt or prodrug thereof, wherein:
$R^1$, $R^2$, $R^3$, and $R^4$ are each independently selected from H or alkyl;
P is H, OH, halogen, or hydroxyl protected by a hydroxyl protecting group;
Q is —$(CR_2)_p$—W—$(CR_2)_q$—, optionally substituted by one or more substituents selected from the group consisting of alkyl, haloalkyl, OR, CN, CONRR', SR, or NRR', p and q are each independently 0, 1, or 2;
W is absent, —CONR—, or —NRCO—;
Y is a divalent —NR(C=O)—$(CR_2)_n$— or —(C=O)NR—$(CR_2)_n$— group, n is 0, 1, or 2;
R and R' are each independently selected from H or alkyl; and
Z is an aromatic or heteroaromatic ring, substituted by one or more substituents selected from the group consisting of alkyl, haloalkyl, OH, halogen, or hydroxyl protected by a hydroxyl protecting group.

5. The compound of claim 1, wherein the compound has the structure of Formula Id:

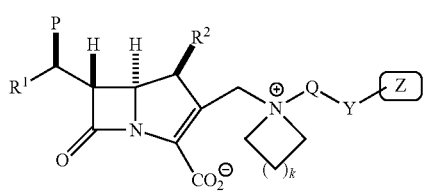

Formula Id or a pharmaceutically acceptable salt or prodrug thereof, wherein:
$R^1$ and $R^2$ are each independently selected from H or alkyl;
P is H, OH, halogen, or hydroxyl protected by a hydroxyl protecting group;
Q is —$(CR_2)_p$—W—$(CR_2)_q$—, optionally substituted by one or more substituents selected from the group consisting of alkyl, haloalkyl, OR, CN, CONRR', SR, or NRR', p and q are each independently 0, 1, or 2;
W is absent, —CONR—, or —NRCO—;
Y is a divalent —NR(C=O)—$(CR_2)_n$— or —(C=O)NR—$(CR_2)_n$— group, n is 0, 1, or 2;
k is 1, 2, or 3;
R and R' are each independently selected from H or alkyl; and
Z is an aromatic or heteroaromatic ring, substituted by one or more substituents selected from the group consisting of alkyl, haloalkyl, OH, halogen, or hydroxyl protected by a hydroxyl protecting group.

6. The compound of claim 1, wherein the compound has the structure of Formula Ie:

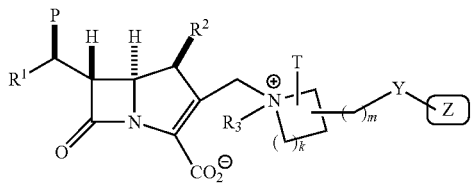

Formula Ie or a pharmaceutically acceptable salt or prodrug thereof, wherein:
$R^1$, $R^2$, and $R^3$ are each independently selected from H or alkyl;
P is H, OH, halogen, or hydroxyl protected by a hydroxyl protecting group;
T is absent, alkyl, haloalkyl, OR, CN, CONRR', SR, or NRR';
Y is a divalent —NR(C=O)—$(CR_2)_n$— or —(C=O)NR—$(CR_2)_n$— group, n is 0, 1, or 2;
k is 1, 2, or 3;
m is 0, 1, or 2;
R and R' are each independently selected from H or alkyl; and
Z is an aromatic or heteroaromatic ring, substituted by one or more substituents selected from the group consisting of alkyl, haloalkyl, OH, halogen, or hydroxyl protected by a hydroxyl protecting group.

7. A compound of Formula (IIa) or Formula (IIb):

Formula (IIa)

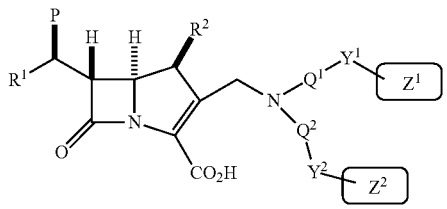

Formula (IIb)

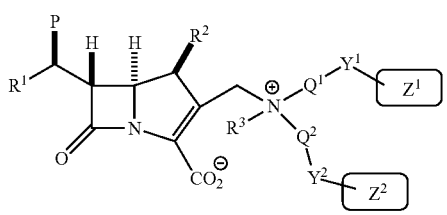

or a pharmaceutically acceptable salt or prodrug thereof, wherein:
$R^1$ and $R^2$ are each independently selected from H or alkyl;
P is H, OH, halogen, or hydroxyl protected by a hydroxyl protecting group;
$Q^1$ and $Q^2$ are each independently selected from a divalent —$(CR_2)_p$—W—$(CR_2)_q$—, optionally substituted by one or more substituents selected from the group consisting of alkyl, haloalkyl, OR, CN, CONRR', SR, or NRR';
p and q are each independently 0, 1, or 2, and at least one of p or q is not 0;
W is absent, —CONR—, or —NRCO—;
$Y^1$ and $Y^2$ are each independently selected from a divalent —NR(C=O)—$(CR_2)_n$— or —(C=O)NR—$(CR_2)_n$— group, wherein n is 0, 1, or 2;
$Z^1$ and $Z^2$ are each independently selected from an aromatic or heteroaromatic ring, substituted by one or more substituents selected from the group consisting of alkyl, haloalkyl, OH, halogen, or hydroxyl protected by a hydroxyl protecting group; and
$R^3$ in Formula (IIb) is H or alkyl.

8. A compound of Formula (IIIa) or Formula (IIIb):

Formula (IIIa)

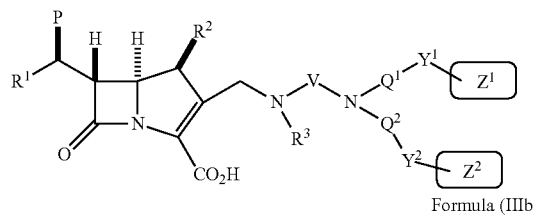

Formula (IIIb)

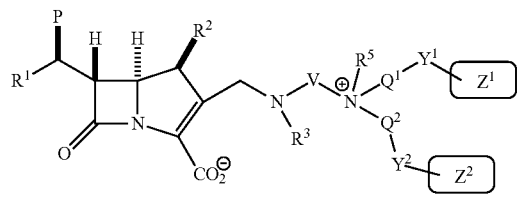

or a pharmaceutically acceptable salt or prodrug thereof, wherein:
$R^1$, $R^2$ and $R^3$ are each independently selected from H or alkyl;
P is H, OH, halogen, or hydroxyl protected by a hydroxyl protecting group;
V is a divalent —$(CR_2)_n$—(C=O)— or —$(CR_2)_n$— group, wherein n is 1, 2 or 3;
$Q^1$ and $Q^2$ are each independently selected from a divalent —$(CR_2)_p$—W—$(CR_2)_q$—, optionally substituted by one or more substituents selected from the group consisting of alkyl, haloalkyl, OR, CN, CONRR', SR, or NRR';
p and q are each independently 0, 1, or 2, and at least one of p or q is not 0;
W is absent, —CONR—, or —NRCO—;
$Y^1$ and $Y^2$ are each independently selected from a divalent —NR(C=O)—$(CR_2)_n$— or —(C=O)NR—$(CR_2)_n$— group, wherein n is 0, 1, or 2;
$Z^1$ and $Z^2$ are each independently selected from an aromatic or heteroaromatic ring, substituted by one or more substituents selected from the group consisting of alkyl, haloalkyl, OH, halogen, or hydroxyl protected by a hydroxyl protecting group; and
$R^5$ in Formula (IIIb) is H or alkyl.

9. A pharmaceutical composition comprising a compound of claim 1 and a pharmaceutically acceptable carrier or diluent.

10. The pharmaceutical composition of claim 9, further comprising at least one additional anti-bacterial agent.

11. A method of treating a bacterial infection in a host comprising administering a therapeutic amount of a compound of claim 1, optionally in a pharmaceutically acceptable carrier or diluent.

12. The method of claim 11, wherein the host is a human.

13. The method of claim 11, wherein the compound is administered orally, parenterally, intravenously, intradermally, subcutaneously or topically.

14. The method of claim 11, wherein the bacterial infection is due to Gram-negative bacteria.

15. The method of claim 14, wherein the bacterial infection is a drug resistant or multiple-drug resistant bacterial infection.

16. The method of claim 11, wherein the compound is administered in combination or alternation with at least one additional anti-bacterial agent.

17. The method of claim 11, wherein the bacterial infection is due to an *Acinetobacter baumannii* bacterium or is from a drug resistant *Acinetobacter baumannii* bacterium, a multi-drug resistant (MDR) *Acinetobacter baumannii* bacterium, an extensive drug resistant (XDR) *Acinetobacter baumannii* bacterium or a pandrug resistant (PDR) *Acinetobacter baumannii* bacterium.

* * * * *